(12) United States Patent
Coburn et al.

(10) Patent No.: US 9,981,969 B2
(45) Date of Patent: May 29, 2018

(54) IMIDAZOLE DERIVATIVES AND METHODS OF USE THEREOF FOR IMPROVING THE PHARMACOKINETICS OF A DRUG

(71) Applicant: MERCK SHARP & DOHME CORP., Rahway, NJ (US)

(72) Inventors: Craig A. Coburn, Novato, CA (US); Milana Maletic, Summit, NJ (US); Yunfu Luo, Shanghai (CN); Zhiqi Qi, Shanghai (CN); Chunsing Li, Shanghai (CN); Tingting Yu, Shanghai (CN); Richard Soll, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 14/895,406

(22) PCT Filed: Jun. 2, 2014

(86) PCT No.: PCT/US2014/040441
§ 371 (c)(1),
(2) Date: Dec. 2, 2015

(87) PCT Pub. No.: WO2014/197345
PCT Pub. Date: Dec. 11, 2014

(65) Prior Publication Data
US 2016/0108048 A1    Apr. 21, 2016

(30) Foreign Application Priority Data

Jun. 7, 2013  (WO) ............... PCT/CN2013/076951

(51) Int. Cl.
| | | |
|---|---|---|
| *C07D 487/04* | (2006.01) | |
| *C07D 401/14* | (2006.01) | |
| *C07D 413/14* | (2006.01) | |
| *A61K 31/4985* | (2006.01) | |
| *A61K 31/5365* | (2006.01) | |
| *C07D 401/06* | (2006.01) | |
| *C07D 471/04* | (2006.01) | |
| *C07D 498/04* | (2006.01) | |
| *A61K 45/06* | (2006.01) | |
| *A61K 31/4375* | (2006.01) | |
| *A61K 31/4545* | (2006.01) | |
| *A61K 31/513* | (2006.01) | |
| *A61K 31/55* | (2006.01) | |
| *C07D 405/14* | (2006.01) | |
| *A61K 31/454* | (2006.01) | |
| *A61K 31/496* | (2006.01) | |
| *A61K 31/5383* | (2006.01) | |
| *A61K 31/551* | (2006.01) | |

(52) U.S. Cl.
CPC ........ *C07D 487/04* (2013.01); *A61K 31/4375* (2013.01); *A61K 31/454* (2013.01); *A61K 31/4545* (2013.01); *A61K 31/496* (2013.01); *A61K 31/4985* (2013.01); *A61K 31/513* (2013.01); *A61K 31/5365* (2013.01); *A61K 31/5383* (2013.01); *A61K 31/55* (2013.01); *A61K 31/551* (2013.01); *A61K 45/06* (2013.01); *C07D 401/06* (2013.01); *C07D 401/14* (2013.01); *C07D 405/14* (2013.01); *C07D 413/14* (2013.01); *C07D 471/04* (2013.01); *C07D 498/04* (2013.01)

(58) Field of Classification Search
CPC .. C07D 401/06; C07D 401/14; C07D 405/14; C07D 413/14; C07D 471/04; C07D 487/04; C07D 498/04
USPC .... 514/218, 230.5, 235.8, 249, 253.09, 269, 514/312, 216, 326; 540/492; 544/105, 544/129, 350, 364; 546/187, 210
See application file for complete search history.

(56) References Cited

U.S. PATENT DOCUMENTS

| | | |
|---|---|---|
| 5,439,928 A | 8/1995 | Karjalainen et al. |
| 5,990,154 A | 11/1999 | Harris |

(Continued)

FOREIGN PATENT DOCUMENTS

| | | | |
|---|---|---|---|
| EP | 277384 | * | 8/1988 |
| WO | 2002081478 A2 | | 10/2002 |

(Continued)

OTHER PUBLICATIONS

CHEMCATS RN 1902710-67-1 (2016).*

(Continued)

*Primary Examiner* — Rita J Desai
(74) *Attorney, Agent, or Firm* — Jeffrey P. Bergman; Catherine D. Fitch

(57) ABSTRACT

The present invention relates to Imidazole Derivatives of Formula (I), and pharmaceutically acceptable salts thereof, wherein A, B, Y, $R^1$ and $R^2$ are as defined herein. The present invention also relates to compositions comprising at least one Imidazole Derivative, and methods of using the Imidazole Derivatives for inhibiting CYP450 3A. Inhibition of CYP450 3A can be used to improve the pharmacokinetics of a drug that is metabolized by CYP450 3A4.

(I)

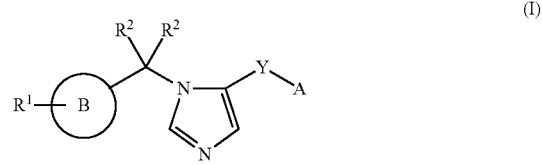

5 Claims, No Drawings

(56) References Cited

U.S. PATENT DOCUMENTS

| | | | |
|---|---|---|---|
| 5,993,887 | A | 11/1999 | Harris |
| 6,124,477 | A | 9/2000 | Harris |
| 6,248,776 | B1 | 6/2001 | Harris |
| 7,919,488 | B2 | 4/2011 | Planken et al. |
| 2007/0105900 | A1 | 5/2007 | Berdini et al. |
| 2008/0090882 | A1 | 4/2008 | Dorsch et al. |
| 2009/0175820 | A1 | 7/2009 | Desai et al. |

FOREIGN PATENT DOCUMENTS

| | | |
|---|---|---|
| WO | 2002092595 A1 | 11/2002 |
| WO | 2005030739 A1 | 4/2005 |
| WO | 2006108879 A2 | 10/2006 |
| WO | 2007034312 A2 | 3/2007 |
| WO | 2008010921 A2 | 1/2008 |
| WO | 2008022345 A1 | 2/2008 |
| WO | 2008101079 A1 | 8/2008 |
| WO | 2008004096 A1 | 10/2008 |
| WO | 2009071650 A2 | 6/2009 |
| WO | 2009152228 A2 | 12/2009 |
| WO | 2012149413 A1 | 11/2012 |
| WO | 2013049565 A1 | 4/2013 |
| WO | 2014194519 A1 | 12/2014 |

OTHER PUBLICATIONS

Van Lommen et al. "preparation of mercap . . . " CA141:207206 (2004).*
Aebi et al."preparation of imidaz . . . " CA150:121647 (2009).*
Anthony et al. "Preparation of N- . . . " CA130:282070 (1999).*
Carini et al. "Preparation of biphenyl . . . " CA112:118817 (1990).*
De Bruyn et al. "Preparation of 1H-imi . . . " CA110:38996).*
Goldfarb "Method using lifespan . . . " CA151:115084 (2009).*
Improper Markush, Fed. Reg. v.76(27) 7163-7175, slide 1, 64-67 (2011).*
Lumma et al. "Preparation of 1-acyl . . . " CA133:238021 (2000).*
Miura et al. "Preparaion of 1-(biphenyl . . . " CA155:152517 (2011).*
Janssens et al. "Preparation of 1,4-di . . . " CA140:357378 (2004).*
Kamata et al. "Preparation of spiro . . . " CA146:206222 (2007).*
Berge et al., Pharmaceutical Salts, J. Pharm Sci., 1977, pp. 1-19, 66(1).
Bingham et al., Over one hundred solvates of sulfathiazole, Chem. Commun., 2001, 603-604.
Caira et al., Preparation and Crystal Characterization of a Polymorph,a Monohydrate, and an Ethyl Acetate Solvate of the Antifungal Fluconazole, J. Pharmaceutical Sci, 2004, 601-611, 93(3).
Gould, Salt selection for basic drugs, International J. of Pharmaceutics, 1986, 201-217, 33.
Green & Wuts, Protective Groups in Organic Synthesis, 2nd Edition, 1991, -,-.
PubChem, Compound Summary for morpholin-4-yl-[3-(1-phenylethyl)imidazol-4-yl]methanone: created Mar. 26, 2005, https://pubchem.ncbi.nlm.nih.gov/compound/299431?from=summary#section=Top>.
PubChem., "Compound Summary for: CID50831974", Feb. 22, 2011, https://pubchem.ncbi.nlm.nih.gov/compound/50831974?from=summary#section=Top>.
T. Higuchi and V. Stella, Pro-drugs as NovelDelivery Systems (1987) 14 of the A.C.S. Symposium Series.
Van Tonder, et al., Preparation and Physicochemical Characterization of 5 Niclosamide Solvates and 1 Hemisolvate, AAPS Pharmscitech, 2004, pp. 1-10, 5(1), US.
Masato Chiba, et al., P450 Interaction With Farnesyl-Protein Transferase Inhibitors Metobolic Stability, Inhibitory Potency, and P450 Binding Spectra in Human Liver Microsomes, Biochemical Pharmacology, 2001, 773-776, vol. 62.
Tang, Cuyue, et al, "Comparison of Imidazole- and 2-Methyl Imidazole-Containing Farnesyl-Protein Transferase Inhibitors: Interaction With and Metabolism by Rat Hepatic Cytochrome P450S", Drug Metabolism and Disposition, 2000, pp. 680-686, vol. 28, No. 6.

\* cited by examiner

IMIDAZOLE DERIVATIVES AND METHODS OF USE THEREOF FOR IMPROVING THE PHARMACOKINETICS OF A DRUG

CROSS-REFERENCE TO RELATED APPLICATIONS

This application is the national stage application under 35 U.S.C. 371 of International Patent Application No. PCT/US2014/040441, filed Jun. 2, 2014, which claims priority to International Patent Application No. PCT/CN2013/076951, filed Jun. 7, 2013. Each of the aforementioned international applications is incorporated by reference in its entirety.

FIELD OF THE INVENTION

The present invention relates to Imidazole Derivatives, compositions comprising at least one Imidazole Derivative, and methods of using the Imidazole Derivatives for inhibiting CYP450 3A Inhibition of CYP450 3A can be used to improve the pharmacokinetics of a drug that is metabolized by CYP450 3A.

BACKGROUND OF THE INVENTION

The cytochrome P450 enzyme system (CYP450) is responsible for the biotransformation of drugs from active substances to inactive metabolites that can be excreted from the body. In addition, the metabolism of certain drugs by CYP450 can alter their PK profile and result in sub-therapeutic plasma levels of those drugs over time. In the area of anti-viral therapy, this can lead to resistance of the virus to the drug.

The virus causing acquired immunodeficiency syndrome (AIDS) is know by various names, including human immunodeficiency virus (HIV), of which two distinct families have been indentified—HIV-1 and HIV-2. Many inhibitors of HIV, including HIV protease inhibitors, HIV integrase inhibitors and non-nucleoside reverse transcriptase inhibitors are metabolized by CYP450. This metabolic activity can lead to unfavorable pharmacokinetics, requiring administering more frequent and/or higher doses than are optimal.

Many drugs, including some HIV protease inhibitors, are now paired with other agents that improve exposure of the drug, with the drug-drug interaction being commonly referred to as "boosting." International Publication Nos. WO 2006/108879, WO 2007/034312 and WO 2008/010921; U.S. Patent Publication No. US 2009/0175820; and U.S. Pat. No. 7,919,488 describe compounds useful as pharmacokinetic enhancers.

Ritonavir, a common boosting agent, is widely used with HIV agents and is an HIV protease inhibitor itself that exerts its boosting effect through inhibition of Cytochrome P450 3A4 (CYP3A4) and p-glycoprotein drug transporters. Ritonavir, however, is associated with certain risks, including hepatotoxicity, hyperlipidemia and unfavorable gastrointestinal effects.

SUMMARY OF THE INVENTION

In one aspect, the present invention provides Compounds of Formula (I):

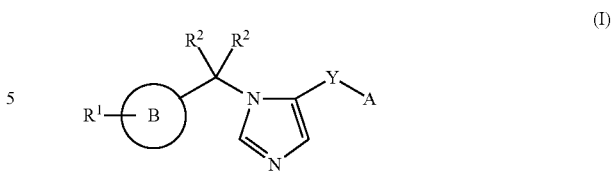

or a pharmaceutically acceptable salt thereof, wherein:

A is:

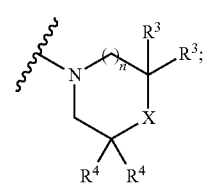

B is phenyl or 5 or 6-membered monocyclic heteroaryl, which is optionally substituted with up to three $R^1$ groups, which can be the same or different;

X is O, —N($R^6$)— or —C($R^5$)$_2$—;

Y is —C(O)—, —S(O)$_2$— or —CH$_2$—;

n is 0, 1 or 2;

$R^1$ is selected from $C_1$-$C_6$ alkyl, $C_6$-$C_{10}$ aryl, 5 or 6-membered heteroaryl, 4 to 7-membered monocyclic heterocycloalkyl and $C_3$-$C_6$ cycloalkyl, wherein said $C_6$-$C_{10}$ aryl group, said 5 or 6-membered heteroaryl group, said 4 to 7-membered monocyclic heterocycloalkyl group or said $C_3$-$C_6$ cycloalkyl group can be optionally substituted with up to four $R^7$ groups, which can be the same or different, and wherein said $C_3$-$C_6$ cycloalkyl group can be fused to a benzene ring and said fused benzene ring can be optionally substituted with up to four $R^7$ groups, which can be the same or different;

each occurrence of $R^2$ is independently selected from H, $C_1$-$C_6$ alkyl and $C_3$-$C_6$ cycloalkyl, or both $R^2$ groups, together with the common carbon atom to which they are each attached, join to form a $C_3$-$C_7$ cycloalkyl group;

each occurrence of $R^3$ is independently selected from H, —OH, halo, $C_1$-$C_6$ alkyl, —O—$C_1$-$C_6$ alkyl, —($C_1$-$C_3$ alkylene)$_n$-($C_3$-$C_6$ cycloalkyl) and —($C_1$-$C_3$ alkylene)$_n$-(5 or 6-membered monocyclic heterocycloalkyl), wherein said $C_3$-$C_6$ cycloalkyl group and said 5 or 6-membered monocyclic heterocycloalkyl group can be optionally substituted on one or more ring carbon atoms with up to 3 groups, each independently selected from H, —OH, halo, $C_1$-$C_6$ alkyl, $C_1$-$C_6$ haloalkyl, —O—$C_1$-$C_6$ alkyl and $C_3$-$C_6$ cycloalkyl; or an $R^3$ group and an $R^5$ group, together with the carbon atoms to which they are attached, can combine to form a $C_3$-$C_6$ cycloalkyl group, a 5 or 6 membered monocyclic heterocycloalkyl group or a 5 or 6 membered heteroaryl group, wherein said $C_3$-$C_6$ cycloalkyl group, said 5 or 6 membered monocyclic heterocycloalkyl group and said 5 or 6 membered heteroaryl group can be optionally substituted on one or more ring carbon atoms with up to 3 groups, each independently selected from H, —OH, halo, $C_1$-$C_6$ alkyl, $C_1$-$C_6$ haloalkyl, —O—$C_1$-$C_6$ alkyl and $C_3$-$C_6$ cycloalkyl; or an $R^3$ group and an $R^6$ group, together with the carbon atoms to which they are attached, can combine to form a 5 or 6 membered monocyclic heterocycloalkyl group or a 5 or 6 membered heteroaryl group, wherein said 5 or 6 membered monocyclic heterocycloalkyl group and said 5 or 6 membered heteroaryl group can be optionally substituted on one or more ring carbon atoms with up to 3 groups, each independently selected from H, —OH, halo, $C_1$-$C_6$ alkyl, $C_1$-$C_6$ haloalkyl, —O—$C_1$-$C_6$ alkyl and $C_3$-$C_6$ cycloalkyl;

each occurrence of $R^4$ is independently selected from H, —OH, halo, $C_1$-$C_6$ alkyl, —O—$C_1$-$C_6$ alkyl, —($C_1$-$C_3$ alkylene)$_n$-($C_3$-$C_6$ cycloalkyl) and —($C_1$-$C_3$ alkylene)$_n$-(5 or 6-membered monocyclic heterocycloalkyl), wherein said $C_3$-$C_6$ cycloalkyl group and said 5 or 6-membered monocyclic heterocycloalkyl group can be optionally substituted on one or more ring carbon atoms with up to 3 groups, each independently selected from H, —OH, halo, $C_1$-$C_6$ alkyl, $C_1$-$C_6$ haloalkyl, —O—$C_1$-$C_6$ alkyl and $C_3$-$C_6$ cycloalkyl; or an $R^4$ group and an $R^5$ group, together with the carbon atoms to which they are attached, can combine to form a $C_3$-$C_6$ cycloalkyl group, a 5 or 6 membered monocyclic heterocycloalkyl group or a 5 or 6 membered heteroaryl group, wherein said $C_3$-$C_6$ cycloalkyl group, said 5 or 6 membered monocyclic heterocycloalkyl group and said 5 or 6 membered heteroaryl group can be optionally substituted on one or more ring carbon atoms with up to 3 groups, each independently selected from H, —OH, halo, $C_1$-$C_6$ alkyl, $C_1$-$C_6$ haloalkyl, —O—$C_1$-$C_6$ alkyl and $C_3$-$C_6$ cycloalkyl; or an $R^4$ group and an $R^6$ group, together with the carbon atoms to which they are attached, can combine to form a 5 or 6 membered monocyclic heterocycloalkyl group or a 5 or 6 membered heteroaryl group, wherein said 5 or 6 membered monocyclic heterocycloalkyl group and said 5 or 6 membered heteroaryl group can be optionally substituted on one or more ring carbon atoms with up to 3 groups, each independently selected from H, —OH, halo, $C_1$-$C_6$ alkyl, $C_1$-$C_6$ haloalkyl, —O—$C_1$-$C_6$ alkyl and $C_3$-$C_6$ cycloalkyl;

each occurrence of $R^5$ is independently H, —NH($R^6$), —OH, halo, $C_1$-$C_6$ alkyl, —O—$C_1$-$C_6$ alkyl, —($C_1$-$C_3$ alkylene)$_n$-($C_3$-$C_6$ cycloalkyl), —($C_1$-$C_3$ alkylene)$_n$-(5 to 7-membered monocyclic heterocycloalkyl) and —($C_1$-$C_3$ alkylene)$_n$-(9 or 10-membered bicyclic heterocycloalkyl) wherein said $C_3$-$C_6$ cycloalkyl group, said 5 to 7-membered monocyclic heterocycloalkyl group and said 9 or 10-membered bicyclic heterocycloalkyl group can be optionally substituted on one or more ring carbon atoms with up to 3 groups, each independently selected from $R^7$, or both $R^5$ groups, and the common carbon atom to which they are each attached, join to form a spirocyclic $C_3$-$C_6$ cycloalkyl group or a spirocyclic 5 to 7-membered monocyclic heterocycloalkyl group, wherein said spirocyclic $C_3$-$C_6$ cycloalkyl group and said spirocyclic 5 or 6-membered monocyclic heterocycloalkyl group can be optionally and independently substituted on up to 3 ring carbon atoms with a group selected from H, —OH, halo, $C_1$-$C_6$ alkyl, $C_1$-$C_6$ haloalkyl, —O—$C_1$-$C_6$ alkyl and $C_3$-$C_6$ cycloalkyl;

each occurrence of $R^6$ is independently selected from H, $C_1$-$C_6$ alkyl, $C_3$-$C_7$ cycloalkyl, —($C_1$-$C_6$ alkyl)-O—($C_1$-$C_6$ alkyl), 4 to 7-membered monocyclic heterocycloalkyl, —C(O)—($C_1$-$C_6$ alkyl) and —S(O)$_2$—($C_1$-$C_6$ alkyl);

each occurrence of $R^7$ is independently selected from $C_1$-$C_6$ alkyl, $C_6$-$C_{10}$ aryl, 5 or 6-membered heterocycloalkyl, 5 or 6-membered heteroaryl, $C_1$-$C_6$ hydroxyalkyl, $C_1$-$C_6$ haloalkyl, halo, —CN, —N($R^6$)$_2$, —CH$_2$N($R^8$)$_2$, —OR$^6$, —C(O)OR$^6$, —SR$^6$, —S(O)$_2$R$^6$ and —C(O)N($R^6$)$_2$, wherein said $C_6$-$C_{10}$ aryl group, said 5 or 6-membered heteroaryl group or said 5 or 6-membered heterocycloalkyl group can be optionally substituted with a group selected from $C_1$-$C_6$ alkyl, halo, $C_1$-$C_6$ hydroxyalkyl, $C_1$-$C_6$ haloalkyl, halo, —CN, —N($R^6$)$_2$, —OR$^6$ and —($C_1$-$C_6$ alkylene)-OR$^6$.

The Compounds of Formula (I) (also referred to herein as the "Imidazole Derivatives") and pharmaceutically acceptable salts thereof can inhibit CYP3A4, and are also believed to be useful, for example, for enhancing or improving the pharmacokinetics of a drug that is metabolized by CYP3A4. Without being bound by any specific theory, it is believed that the Imidazole Derivatives inhibit CYP3A4, and possibly other members of the CYP3A family.

Accordingly, the present invention provides methods for improving the pharmacokinetics of a therapeutic compound that is metabolized by CYP3A4, the methods comprising administering to a subject in need of such treatment an effective amount of a combination of said drug and a compound of Formula (I) or a pharmaceutically acceptable salt thereof.

The present invention also provides methods for inhibiting CYP3A4 in a subject, comprising administering to said subject a compound of Formula (I) or pharmaceutically acceptable salt thereof, in an amount that is effective to inhibit CYP3A4 in said subject.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to Imidazole Derivatives, compositions comprising at least one Imidazole Derivative, and methods of using the Imidazole Derivatives for inhibiting CYP3A4 or for improving the pharmacokinetics of a therapeutic compound that is metabolized by CYP3A4.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In still another embodiment, the subject is a dog, cat, horse, pig, hamster or other companion animal.

The term "effective amount" as used herein, refers to: (i) an amount administered of a Imidazole Derivative, or pharmaceutically acceptable salt thereof, that is effective for inhibiting CYP3A4 in a subject, (ii) the amounts administered of each of a combination of: (A) a Imidazole Derivative, or pharmaceutically acceptable salt thereof, and (B) a therapeutic compound metabolized by CYP3A4 wherein the amounts administered are together effective in producing the desired therapeutic, ameliorative, inhibitory or preventative effect when administered to a subject. In one embodiment the patient is suffering from HIV infection or AIDS and the therapeutic compound is an anti-HIV agent. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected. Examples of substituents include halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected. Examples of substituents include halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butyryl and 3-methylbutynyl. An alkynyl group may be unsubstituted or substituted by one or more substituents which may be the same or different, each substituent being independently selected. Examples of substituents include halo, alkenyl, alkynyl, aryl, cycloalkyl, cyano, hydroxy, —O— alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$— and —$CH_2CH(CH_3)CH_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms. The term "$C_3$-$C_5$ alkylene" refers to an alkylene group having from 3 to 5 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH=CH—, —CH=CHCH$_2$—, —$CH_2$CH=CH—, —$CH_2$CH=CHCH$_2$—, —CH=CHCH$_2$CH$_2$—, —$CH_2CH_2$CH=CH— and —CH(CH$_3$)CH=CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "$C_2$-$C_6$ alkenylene" refers to an alkenylene group having from 2 to 6 carbon atoms. The term "$C_3$-$C_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

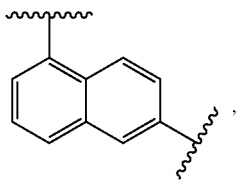 [SMILES: *c1ccc2c(*)cccc2c1]

is understood to represent both:

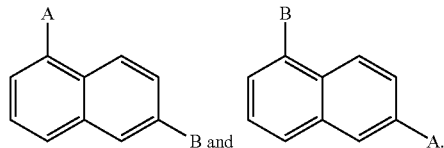

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

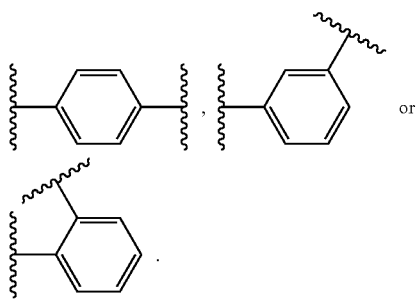

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 6-membered cycloalkyl" refers to a cycloalkyl group having from 3 to 6 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

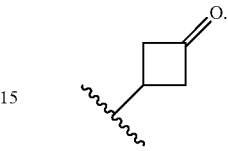

The term "CYP3A," as used herein, refers to the all the known members of the 3A subfamily of the cytochrome P450 superfamily of genes. CYP3A includes, but is not limited to CYP3A4, CYP3A5, CYP3A7 and CYP3A43. In one embodiment, the CYP3A gene is CYP3A4.

The term "halo," as used herein, means —F, —Cl, —Br or —I. In one embodiment, the halo group is F.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms (a "5 or 6-membered monocyclic heteroaryl" group). In another embodiment, a heteroaryl group is bicyclic. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms (a "3 to 7-membered monocyclic heterocycloalkyl" group). In another embodiment, a heterocycloalkyl group is monocyclic has from about 4 to about 7 ring atoms (a "4 to 7-membered monocyclic heterocycloalkyl" group). In another embodiment, the heterocycloalkyl group is bicyclic and has 9 or 10 ring atoms (a "9 or 10-membered bicyclic heterocycloalkyl" group). In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

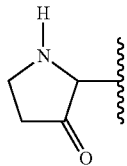

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "heteroarylene," as used herein, refers to a bivalent group derived from a heteroaryl group, as defined above, by removal of a hydrogen atom from a ring carbon of a heteroaryl group. A heteroarylene group can be derived from a monocyclic or multicyclic ring system comprising from about 6 to about 14 carbon atoms. In one embodiment, a heteroarylene group contains from about 6 to about 10 carbon atoms. In another embodiment, a heteroarylene group is a naphthylene group. In another embodiment, a heteroarylene group is a phenylene group. A heteroarylene group can be optionally substituted with one or more "ring system substituents" which may be the same or different, and are as defined herein below. A heteroarylene group is divalent and either available bond on a heteroarylene group can connect to either group flanking the heteroarylene group. For example, the group "A-heteroarylene-B," wherein the arylene group is:

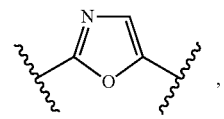 [SMILES: *c1cnc(*)o1]

is understood to represent both:

Non-limiting examples of heteroarylene groups include thiazolyl, pyridyl, pyranyl, tetrahydropyranyl, pyrmidinyl, indolyl, benzoquinolinyl, oxazolyl, benzisoxazolyl and pyrazinyl. In one embodiment, a heteroarylene group is unsubstituted. Unless otherwise indicated, a heteroarylene group is unsubstituted.

The term "HIV," as used herein, refers generically to all known species of the HIV virus, including, but not limited to, HIV-1 and HIV-2.

The term "ring system substituent," as used herein, refers to a substituent group attached to an aromatic or non-aromatic ring system which, for example, replaces an available hydrogen on the ring system. Ring system substituents may be the same or different. Examples of the ring substitutents include alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO₂, —CN, —SF₅, —C(O)OH, —C(O)O-alkyl, —C(O)O-aryl, —C(O)O-alkylene-aryl, —S(O)—alkyl, —S(O)₂-alkyl, —S(O)-aryl, —S(O)₂-aryl, —S(O)-heteroaryl, —S(O)₂-heteroaryl, —S-alkyl, —S-aryl, —S-heteroaryl, —S-alkylene-aryl, —S-alkylene-heteroaryl, —S(O)₂-alkylene-aryl, —S(O)₂-alkylene-heteroaryl, —Si(alkyl)₂, —Si(aryl)₂, —Si(heteroaryl)₂, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

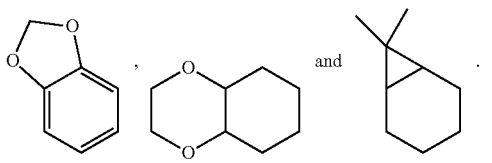

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., C$_1$-C$_6$ alkyl, R$^2$, R$^8$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Imidazole Derivative or a pharmaceutically acceptable salt of the compound. The transformation may occur by various mechanisms (e.g., by metabolic or chemical processes), such as, for example, through hydrolysis in blood.

For example, if a Imidazole Derivative or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di (C$_1$-C$_2$)alkylcarbamoyl-(C$_1$-C$_2$)alkyl and piperidino-, pyrrolidino- or morpholino(C$_2$-C$_3$)alkyl, and the like. Similarly, if a Imidazole Derivative contains an alcohol functional group, a prodrug can be formed by the replacement of one or more of the hydrogen atoms of the alcohol groups with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylaminomethyl, succinoyl, (C$_1$-C$_6$)alkanoyl, α-amino (C$_1$-C$_4$)alkyl, α-amino(C$_1$-C$_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate) or a phosphate of structure PO$_3$M$_2$ where M is either sodium or potassium.

If a Imidazole Derivative incorporates an amine functional group, a prodrug can be formed by the replacement of a hydrogen atom in the amine group with a group such as, for example, R-carbonyl-, RO-carbonyl-, NRR'-carbonyl-wherein R and R' are each independently (C$_1$-C$_{10}$)alkyl, (C$_3$-C$_7$) cycloalkyl, benzyl, a natural α-aminoacyl, —C(OH)C(O)OY$^1$ wherein Y$^1$ is H, (C$_1$-C$_6$)alkyl or benzyl, —C(OY$^2$)Y$^3$ wherein Y$^2$ is (C$_1$-C$_4$) alkyl and Y$^3$ is (C$_1$-C$_6$) alkyl; carboxy (C$_1$-C$_6$)alkyl; amino(C$_1$-C$_4$)alkyl or mono-N— or di-N,N—(C$_1$-C$_6$)alkylaminoalkyl; —C(Y$^4$)Y$^5$ wherein Y$^4$ is H or methyl and Y$^5$ is mono-N— or di-N, N—(C$_1$-C$_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Imidazole Derivatives can form salts which are also within the scope of this invention. Reference to a Imidazole Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Imidazole Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Imidazole Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Imidazole Derivatives may be atropisomers (e.g., substituted biaryls) and are considered as part of this invention. Enantiomers can also be directly separated using chiral chromatographic techniques.

It is also possible that the Imidazole Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Imidazole Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Imidazole Derivatives, and of the salts, solvates, hydrates, esters and prodrugs of the Imidazole Derivatives, are intended to be included in the present invention.

The following abbreviations are used below and have the following meanings: AcOH is acetic acid; Boc is tert-butyloxycarbonyl, (Boc)$_2$O or Boc$_2$O is Boc anhydride; n-BuLi is n-butyl lithium; t-BuNO$_2$ or t-BuONO is tert-butyl nitrite; Cbz is carboxybenzyl; DCM is dichloromethane; DIEA is N,N-diisopropylethylamine; DMF is dimethylformamide; DMSO is dimethylsulfoxide; EtOAc is ethyl acetate; EtOH is ethanol; Et$_a$ or TEA is triethylamine; HMPA is hexamethylphosphoramide; HOAc is acetic acid; HPLC is high-pressure liquid chromatography; KSCN is potassium thiocyanate; LCMS is liquid chromatography-mass spectrometry; LDA is lithium diisopropylamide; MeCN is acetonitrile; MeI is iodomethane; MeOH is methanol; MS is mass spectroscopy; NaBH(OAc)$_3$ is sodium triacetoxy borohydride; NMR is nuclear magnetic resonance spectroscopy; PCy$_3$ is tricyclohexylphosphine; Pd(OAc)$_2$ is palladium(II) acetate; Pd$_2$(dba)$_3$ is tris dibenzylideneacetone dipalladium; PE is petroleum ether; PG is protecting group; Pd/C is palladium on carbon; Prep is preparative; rt is room temperature; TBAF is n-tetrabutylammonium fluoride; TFA is trifluoroacetic acid; TLC is thin-layer chromatography; TMSCN is trimethylsilyl cyanide; Ts is 4-toluenesulfonyl; THF is tetrahydrofuran; wt % is percentage by weight; and X-phos is 2-dicyclohexylphosphino-2',4',6'-triisopropylbiphenyl.

The Compounds of Formula (I)

The present invention provides Imidazole Derivatives of Formula (I):

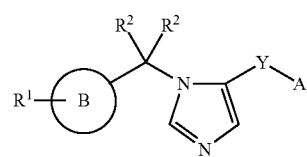

(I)

and pharmaceutically acceptable salts thereof, wherein A, B, Y, $R^1$ and $R^2$ are defined above for the Compounds of Formula (I).

In one embodiment, for the Compounds of Formula (I), B is phenyl.

In another embodiment, for the Compounds of Formula (I), B is 5 or 6-membered heteroaryl.

In another embodiment, for the Compounds of Formula (I), B is pyridyl.

In one embodiment, for the Compounds of Formula (I), Y is —C(O)—.

In another embodiment, for the Compounds of Formula (I), Y is —S(O)$_2$—.

In another embodiment, for the Compounds of Formula (I), Y is —CH$_2$—.

In one embodiment, for the Compounds of Formula (I), one $R^2$ is H and the other is $C_1$-$C_6$ alkyl.

In another embodiment, for the Compounds of Formula (I), one $R^2$ is H and the other is methyl.

In another embodiment, for the Compounds of Formula (I), both $R^2$ groups are H.

In still another embodiment, for the Compounds of Formula (I), both $R^2$ groups are $C_1$-$C_6$ alkyl.

In another embodiment, for the Compounds of Formula (I), both $R^2$ groups are methyl.

In another embodiment, for the Compounds of Formula (I), both $R^2$ groups, together with the common carbon atom to which they are each attached, join to form a $C_3$-$C_7$ cycloalkyl group.

In yet another embodiment, for the Compounds of Formula (I), both $R^2$ groups, together with the common carbon atom to which they are each attached, join to form a cyclopropyl group.

In one embodiment, the compounds of formula (I) have the formula (Ia):

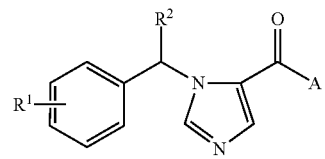

(Ia)

or a pharmaceutically acceptable salt thereof, wherein:
A is:

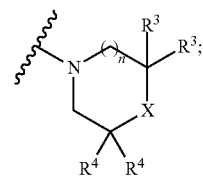

X is O, —N(R$^6$)— or —C(R$^5$)$_2$—;

n is 0, 1 or 2;

R$^1$ is selected from C$_1$-C$_6$ alkyl, C$_6$-C$_{10}$ aryl, 5 or 6-membered heteroaryl, 4 to 7-membered monocyclic heterocycloalkyl and C$_3$-C$_6$ cycloalkyl, wherein said C$_6$-C$_{10}$ aryl group, said 5 or 6-membered heteroaryl group, said 4 to 7-membered monocyclic heterocycloalkyl group or said C$_3$-C$_6$ cycloalkyl group can be optionally substituted with up to four R$^7$ groups, which can be the same or different, and wherein said C$_3$-C$_6$ cycloalkyl group can be fused to a benzene ring and said fused benzene ring can be optionally substituted with up to four R$^7$ groups, which can be the same or different;

each occurrence of R$^2$ is independently selected from H, C$_1$-C$_6$ alkyl and C$_3$-C$_6$ cycloalkyl;

each occurrence of R$^3$ is independently selected from H, —OH, halo, C$_1$-C$_6$ alkyl, —O—C$_1$-C$_6$ alkyl, —(C$_1$-C$_3$ alkylene)$_n$-(C$_3$-C$_6$ cycloalkyl) and —(C$_1$-C$_3$ alkylene)$_n$-(5 or 6-membered monocyclic heterocycloalkyl), wherein said C$_3$-C$_6$ cycloalkyl group and said 5 or 6-membered monocyclic heterocycloalkyl group can be optionally substituted on one or more ring carbon atoms with up to 3 groups, each independently selected from H, —OH, halo, C$_1$-C$_6$ alkyl, C$_1$-C$_6$ haloalkyl, —O—C$_1$-C$_6$ alkyl and C$_3$-C$_6$ cycloalkyl; or an R$^3$ group and an R$^5$ group, together with the carbon atoms to which they are attached, can combine to form a C$_3$-C$_6$ cycloalkyl group, a 5 or 6 membered monocyclic heterocycloalkyl group or a 5 or 6 membered heteroaryl group, wherein said C$_3$-C$_6$ cycloalkyl group, said 5 or 6 membered monocyclic heterocycloalkyl group and said 5 or 6 membered heteroaryl group can be optionally substituted on one or more ring carbon atoms with up to 3 groups, each independently selected from H, —OH, halo, C$_1$-C$_6$ alkyl, C$_1$-C$_6$ haloalkyl, —O—C$_1$-C$_6$ alkyl and C$_3$-C$_6$ cycloalkyl; or an R$^3$ group and an R$^8$ group, together with the carbon atoms to which they are attached, can combine to form a 5 or 6 membered monocyclic heterocycloalkyl group or a 5 or 6 membered heteroaryl group, wherein said 5 or 6 membered monocyclic heterocycloalkyl group and said 5 or 6 membered heteroaryl group can be optionally substituted on one or more ring carbon atoms with up to 3 groups, each independently selected from H, —OH, halo, C$_1$-C$_6$ alkyl, C$_1$-C$_6$ haloalkyl, —O—C$_1$-C$_6$ alkyl and C$_3$-C$_6$ cycloalkyl;

each occurrence of R$^4$ is independently selected from H, —OH, halo, C$_1$-C$_6$ alkyl, —O—C$_1$-C$_6$ alkyl, —(C$_1$-C$_3$ alkylene)$_n$-(C$_3$-C$_6$ cycloalkyl) and —(C$_1$-C$_3$ alkylene)$_n$-(5 or 6-membered monocyclic heterocycloalkyl), wherein said C$_3$-C$_6$ cycloalkyl group and said 5 or 6-membered monocyclic heterocycloalkyl group can be optionally substituted on one or more ring carbon atoms with up to 3 groups, each independently selected from H, —OH, halo, C$_1$-C$_6$ alkyl, C$_1$-C$_6$ haloalkyl, —O—C$_1$-C$_6$ alkyl and C$_3$-C$_6$ cycloalkyl; or an R$^4$ group and an R$^5$ group, together with the carbon atoms to which they are attached, can combine to form a C$_3$-C$_6$ cycloalkyl group, a 5 or 6 membered monocyclic heterocycloalkyl group or a 5 or 6 membered heteroaryl group, wherein said C$_3$-C$_6$ cycloalkyl group, said 5 or 6 membered monocyclic heterocycloalkyl group and said 5 or 6 membered heteroaryl group can be optionally substituted on one or more ring carbon atoms with up to 3 groups, each independently selected from H, —OH, halo, C$_1$-C$_6$ alkyl, C$_1$-C$_6$ haloalkyl, —O—C$_1$-C$_6$ alkyl and C$_3$-C$_6$ cycloalkyl; or an R$^4$ group and an R$^8$ group, together with the carbon atoms to which they are attached, can combine to form a 5 or 6 membered monocyclic heterocycloalkyl group or a 5 or 6 membered heteroaryl group, wherein said 5 or 6 membered monocyclic heterocycloalkyl group and said 5 or 6 membered heteroaryl group can be optionally substituted on one or more ring carbon atoms with up to 3 groups, each independently selected from H, —OH, halo, C$_1$-C$_6$ alkyl, C$_1$-C$_6$ haloalkyl, —O—C$_1$-C$_6$ alkyl and C$_3$-C$_6$ cycloalkyl;

each occurrence of R$^5$ is independently H, —NH(R$^6$), —OH, halo, C$_1$-C$_6$ alkyl, —O—C$_1$-C$_6$ alkyl, —(C$_1$-C$_3$ alkylene)$_n$-(C$_3$-C$_6$ cycloalkyl), —(C$_1$-C$_3$ alkylene)$_n$-(5 to 7-membered monocyclic heterocycloalkyl) and —(C$_1$-C$_3$ alkylene)$_n$-(9 or 10-membered bicyclic heterocycloalkyl) wherein said C$_3$-C$_6$ cycloalkyl group, said 5 to 7-membered monocyclic heterocycloalkyl group and said 9 or 10-membered bicyclic heterocycloalkyl group can be optionally substituted on one or more ring carbon atoms with up to 3 groups, each independently selected from R$^7$, or both R$^5$ groups, and the common carbon atom to which they are each attached, join to form a spirocyclic C$_3$-C$_6$ cycloalkyl group or a spirocyclic 5 to 7-membered monocyclic heterocycloalkyl group, wherein said spirocyclic C$_3$-C$_6$ cycloalkyl group and said spirocyclic 5 or 6-membered monocyclic heterocycloalkyl group can be optionally and independently substituted on up to 3 ring carbon atoms with a group selected from H, —OH, halo, C$_1$-C$_6$ alkyl, C$_1$-C$_6$ haloalkyl, —O—C$_1$-C$_6$ alkyl and C$_3$-C$_6$ cycloalkyl; each occurrence of R$^6$ is independently H or C$_1$-C$_6$ alkyl;

each occurrence of R$^7$ is independently selected from C$_1$-C$_6$ alkyl, C$_6$-C$_{10}$ aryl, 5 or 6-membered heterocycloalkyl, 5 or 6-membered heteroaryl, C$_1$-C$_6$ hydroxyalkyl, C$_1$-C$_6$ haloalkyl, halo, —CN, —N(R$^6$)$_2$, —CH$_2$N(R$^8$)$_2$, —OR$^6$, —C(O)OR$^6$, —SR$^6$, —S(O)$_2$R$^6$ and —C(O)N(R$^6$)$_2$, wherein said C$_6$-C$_{10}$ aryl group, said 5 or 6-membered heteroaryl group or said 5 or 6-membered heterocycloalkyl group can be optionally substituted with a group selected from C$_1$-C$_6$ alkyl, halo, C$_1$-C$_6$ hydroxyalkyl, C$_1$-C$_6$ haloalkyl, halo, —CN, —N(R$^6$)$_2$, —OR$^6$ and —(C$_1$-C$_6$ alkylene)-OR$^6$.

In one embodiment, the compounds of formula (I) have the formula (Ib):

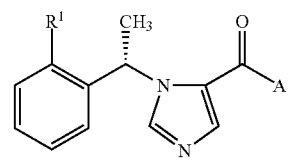

(Ib)

or a pharmaceutically acceptable salt thereof,
wherein:

R$^1$ is selected from C$_1$-C$_6$ alkyl, phenyl, 6-membered heteroaryl, 6-membered monocyclic heterocycloalkyl and C$_5$-C$_6$ cycloalkyl, wherein said phenyl group, said 6-membered heteroaryl group, said 6-membered monocyclic heterocycloalkyl group or said C$_5$-C$_6$ cycloalkyl group can be optionally substituted with up to four R$^7$ groups, which can be the same or different, and wherein said C$_3$-C$_6$ cycloalkyl group can be fused to a benzene ring and said fused benzene ring can be optionally substituted with up to three R$^7$ groups;

R$^5$ is —(C$_1$-C$_3$ alkylene)$_n$-(5 to 7-membered monocyclic heterocycloalkyl) and —(C$_1$-C$_3$ alkylene)$_n$-(9 or 10-membered bicyclic heterocycloalkyl) wherein said 5 to 7-membered monocyclic heterocycloalkyl group and said 9 or 10-membered bicyclic heterocycloalkyl group can be optionally substituted on up to three ring carbon atoms with groups independently selected from R$^7$; and each occurrence of $R^7$ is independently selected from $C_1$-$C_6$ alkyl, —O—($C_1$-$C_6$ alkyl, —($C_1$-$C_6$ alkylene)-O—($C_1$-$C_6$ alkyl) and halo.

In another embodiment, for the Compounds of Formulas (I), (Ia) and (Ib), $R^1$ is $C_1$-$C_6$ alkyl.

In another embodiment, for the Compounds of Formulas (I), (Ia) and (Ib), $R^1$ is phenyl.

In another embodiment, for the Compounds of Formulas (I), (Ia) and (Ib), $R^1$ is 5-membered heteroaryl.

In still another embodiment, for the Compounds of Formulas (I), (Ia) and (Ib), $R^1$ is 6-membered heteroaryl.

In another embodiment, for the Compounds of Formulas (I), (Ia) and (Ib), $R^1$ is 5-membered monocyclic heterocycloalkyl.

In yet another embodiment, for the Compounds of Formulas (I), (Ia) and (Ib), $R^1$ is 6-membered monocyclic heterocycloalkyl.

In another embodiment, for the Compounds of Formulas (I), (Ia) and (Ib), $R^1$ is $C_3$-$C_6$ cycloalkyl.

In a further embodiment, for the Compounds of Formulas (I), (Ia) and (Ib), $R^1$ is $C_5$-$C_6$ cycloalkyl.

In one embodiment, for the Compounds of Formulas (I), (Ia) and (Ib), $R^1$ is optionally substituted phenyl.

In another embodiment, for the Compounds of Formulas (I), (Ia) and (Ib), $R^1$ is para-fluorophenyl.

In one embodiment, for the Compounds of Formulas (I) and (Ia), $R^2$ is $C_1$-$C_6$ alkyl.

In another embodiment, for the Compounds of Formulas (I) and (Ia), $R^2$ is methyl.

In one embodiment, for the Compounds of Formulas (I), (Ia) and (Ib), each occurrence $R^3$ is H.

In another embodiment, for the Compounds of Formulas (I), (Ia) and (Ib), one occurrence of $R^3$ is —OH.

In another embodiment, for the Compounds of Formulas (I), (Ia) and (Ib), one occurrence of $R^3$ is halo.

In still another embodiment, for the Compounds of Formulas (I), (Ia) and (Ib), one occurrence of $R^3$ is $C_1$-$C_6$ alkyl.

In another embodiment, for the Compounds of Formulas (I), (Ia) and (Ib), one occurrence of $R^3$ is methyl.

In yet another embodiment, for the Compounds of Formulas (I), (Ia) and (Ib), one occurrence of $R^3$ is —O—$C_1$-$C_6$ alkyl.

In another embodiment, for the Compounds of Formulas (I), (Ia) and (Ib), one occurrence of $R^3$ is methoxy.

In another embodiment, for the Compounds of Formulas (I), (Ia) and (Ib), one occurrence of $R^3$ is —($C_1$-$C_3$ alkylene)$_n$-($C_3$-$C_6$ cycloalkyl).

In further embodiment, for the Compounds of Formulas (I), (Ia) and (Ib), one occurrence of $R^3$ is —($C_1$-$C_3$ alkylene)$_n$-(5 or 6-membered monocyclic heterocycloalkyl).

In another embodiment, for the Compounds of Formulas (I), (Ia) and (Ib), an $R^3$ group and an $R^5$ group, together with the carbon atoms to which they are attached, can combine to form a $C_3$-$C_6$ cycloalkyl group, a 5 or 6 membered monocyclic heterocycloalkyl group or a 5 or 6 membered heteroaryl group.

In still another embodiment, for the Compounds of Formulas (I), (Ia) and (Ib), an $R^3$ group and an $R^8$ group, together with the carbon atoms to which they are attached, can combine to form a 5 or 6 membered monocyclic heterocycloalkyl group or a 5 or 6 membered heteroaryl group.

In one embodiment, for the Compounds of Formulas (I), (Ia) and (Ib), each occurrence of $R^4$ is H.

In another embodiment, for the Compounds of Formulas (I), (Ia) and (Ib), one occurrence of $R^4$ is —OH.

In another embodiment, for the Compounds of Formulas (I), (Ia) and (Ib), one occurrence of $R^4$ is halo.

In still another embodiment, for the Compounds of Formulas (I), (Ia) and (Ib), one occurrence of $R^4$ is $C_1$-$C_6$ alkyl.

In another embodiment, for the Compounds of Formulas (I), (Ia) and (Ib), one occurrence of $R^4$ is methyl.

In yet another embodiment, for the Compounds of Formulas (I), (Ia) and (Ib), one occurrence of $R^4$ is —O—$C_1$-$C_6$ alkyl.

In another embodiment, for the Compounds of Formulas (I), (Ia) and (Ib), one occurrence of $R^4$ is methoxy.

In another embodiment, for the Compounds of Formulas (I), (Ia) and (Ib), one occurrence of $R^4$ is —($C_1$-$C_3$ alkylene)$_n$-($C_3$-$C_6$ cycloalkyl).

In further embodiment, for the Compounds of Formulas (I), (Ia) and (Ib), one occurrence of $R^4$ is —($C_1$-$C_3$ alkylene)$_n$-(5 or 6-membered monocyclic heterocycloalkyl).

In another embodiment, for the Compounds of Formulas (I), (Ia) and (Ib), an $R^4$ group and an $R^5$ group, together with the carbon atoms to which they are attached, can combine to form a $C_3$-$C_6$ cycloalkyl group, a 5 or 6 membered monocyclic heterocycloalkyl group or a 5 or 6 membered heteroaryl group.

In still another embodiment, for the Compounds of Formulas (I), (Ia) and (Ib), an $R^4$ group and an $R^8$ group, together with the carbon atoms to which they are attached, can combine to form a 5 or 6 membered monocyclic heterocycloalkyl group or a 5 or 6 membered heteroaryl group.

In one embodiment, for the Compounds of Formulas (I), (Ia) and (Ib), one occurrence of $R^5$ is H.

In another embodiment, for the Compounds of Formulas (I), (Ia) and (Ib), one occurrence of $R^5$ is H and the other is 5 to 7-membered monocyclic heterocycloalkyl.

In another embodiment, for the Compounds of Formulas (I), (Ia) and (Ib), one occurrence of $R^5$ is H and the other is 9 or 10-membered bicyclic heterocycloalkyl. In another embodiment, for the Compounds of Formulas (I), (Ia) and (Ib), one occurrence of $R^5$ is H and the other is:

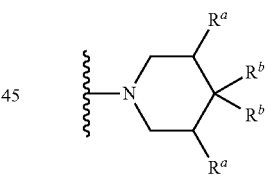

each occurrence of $R^a$ is independently H, hydroxyl, methoxy, halo or methyl.

each occurrence of $R^b$ is independently H, hydroxy, methoxy, halo or methyl, or one $R^a$ group and one $R^b$ group, together with the carbon atoms to which they are attached, join to form a 5 or 6-membered heterocycloalkyl group.

In another embodiment, for the Compounds of Formulas (I), (Ia) and (Ib), A is:

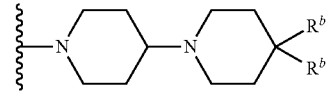

wherein each occurrence of $R^b$ is independently H, hydroxy or methyl.

In another embodiment, for the Compounds of Formulas (I), (Ia) and (Ib), A is:

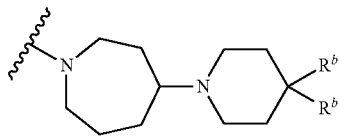

wherein each occurrence of $R^b$ is independently H, hydroxy or methyl.

In another embodiment, for the Compounds of Formulas (I), (Ia) and (Ib), A is:

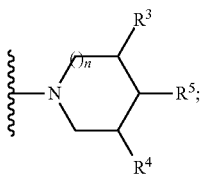

Wherein:

$R^3$ and $R^4$ are each independently selected from H, halo and $C_1$-$C_6$ alkyl; and $R^5$ is selected from —NH($R^6$), —($C_1$-$C_3$ alkylene)$_n$-(5 to 7-membered monocyclic heterocycloalkyl) and —($C_1$-$C_3$ alkylene)$_n$-(9 or 10-membered bicyclic heterocycloalkyl), wherein said 5 to 7-membered monocyclic heterocycloalkyl group and said 9 or 10-membered bicyclic heterocycloalkyl group can be optionally substituted on one or more ring carbon atoms with up to 3 groups, each independently selected from —OH, halo, $C_1$-$C_6$ alkyl, and —O—$C_1$-$C_6$ alkyl.

In one embodiment, for the Compounds of Formulas (I), (Ia) and (Ib), A is:

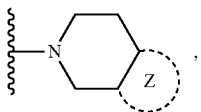

wherein Z is a 4 to 7-membered heterocycloalkyl group.

In another embodiment, for the Compounds of Formulas (I), (Ia) and (Ib), A is:

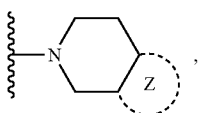

wherein Z is a 6-membered heterocycloalkyl group.

In another embodiment, for the Compounds of Formulas (I), (Ia) and (Ib), A is:

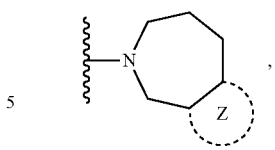

wherein Z is a 4 to 7-membered heterocycloalkyl group.

In still another embodiment, for the Compounds of Formulas (I), (Ia) and (Ib), A is:

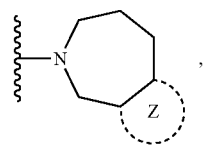

wherein Z is a 6-membered heterocycloalkyl group.

In another embodiment, the compounds of formula (I) have the formula (Ic):

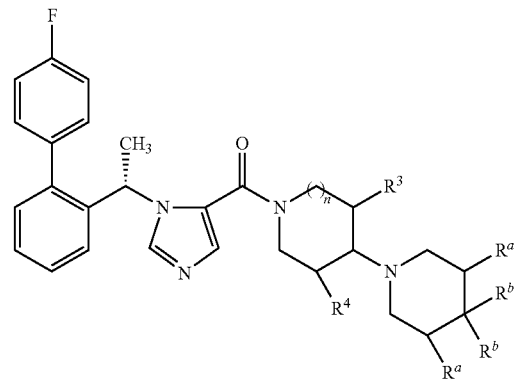

(Ic)

or a pharmaceutically acceptable salt thereof,
wherein:
  n is 1 or 2;
  $R^3$ is selected from H, halo and $C_1$-$C_6$ alkyl;
  $R^4$ is selected from H, halo and $C_1$-$C_6$ alkyl;
  each occurrence of $R^a$ is independently H, methoxy, halo or methyl; and
  each occurrence of $R^b$ is independently H, methoxy, halo or methyl.

In one embodiment, variables A, W, $R^1$, $R^2$, $R^3$, $R^4$ and $R^5$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising one or more therapeutic compounds that are metabolized by CYP3A4.

(c) The pharmaceutical composition of (b), wherein the therapeutic compound is an anti-HIV drug, preferably the anti-HIV drug(s) are selected from the group consisting of HIV protease inhibitors and HIV integrase inhibitors nucleoside reverse transcriptase inhibitors.

(d) A pharmaceutical combination that is (i) a Compound of Formula (I) and ii) a therapeutic compound metabolized by CYP3A4; wherein the Compound of Formula (I) and the therapeutic compound metabolized by CYP3A4 are each employed in an amount that renders the combination effective for inhibiting HIV replication, or for treating HIV infection and/or reducing the likelihood or severity of symptoms of HIV infection.

(e) The combination of (d), wherein the therapeutic compound metabolized by CYP3A4 is selected from the group consisting of HIV protease inhibitors, HIV integrase inhibitors and nucleoside reverse transcriptase inhibitors.

(f) A method of inhibiting HIV replication in a subject in need thereof which comprises administering to the subject: (i) a Compound of Formula (I) and (ii) one or more anti-HIV drugs, wherein the amounts of the Compound of Formula (I) and the anti-HIV drug(s) are together effective to inhibit HIV replication.

(g) A method of treating HIV infection and/or reducing the likelihood or severity of symptoms of HIV infection in a subject in need thereof which comprises administering to the subject (i) a Compound of Formula (I) and (ii) one or more anti-HIV drugs, wherein the amounts of the Compound of Formula (I) and the anti-HIV drug(s) are together effective to treat HIV infection.

(h) The method of (h), wherein the anti-HIV drug(s) are an selected from the group consisting of HIV protease inhibitors, HIV integrase inhibitor and nucleoside reverse transcriptase inhibitors.

(i) A method of inhibiting HIV replication in a subject in need thereof which comprises administering to the subject the pharmaceutical composition of (b) or (c) or the combination of (d) or (e).

(j) A method of treating HIV infection and/or reducing the likelihood or severity of symptoms of HIV infection in a subject in need thereof which comprises administering to the subject the pharmaceutical composition of (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In those uses directed to HIV, the compounds of the present invention are employed in combination with one or more anti-HIV drugs.

Additional embodiments of the invention include the pharmaceutical compositions, combinations and methods set forth in (a)-(j) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (j) above are understood to include all embodiments of the compounds, including such embodiments as result from combinations of embodiments.

Non-limiting examples of the Compounds of Formula (I) include compounds 1-53 as set forth in the Examples below, and pharmaceutically acceptable salts thereof.

Uses of the Imidazole Derivatives

The Imidazole Derivatives are useful in human and veterinary medicine for inhibiting CYP3A4. In addition, the Imidazole Derivatives are useful for improving the pharmacokinetics of a therapeutic compound that is metabolized by CYP3A4. The Imidazole Derivatives also provide a tool for inhibiting CYP3A4 in vitro.

The present invention also provides methods that may be, or are believed to be, useful for inhibiting other members of CYP3A in a subject, said method comprising administering to said subject a Imidazole Derivative, or pharmaceutically acceptable salt thereof, in an amount that is effective to inhibit CYP3A in said subject. In one embodiment, the CYP3A being inhibited is CYP3A5. In another embodiment, the CYP3A being inhibited is CYP3A7. In another embodiment, the CYP3A being inhibited is CYP3A743.

Improving the Pharmacokinetics of a Therapeutic Compound that is Metabolized by CYP3A4

The present invention provides methods for improving the pharmacokinetics of a therapeutic compound that is metabolized by CYP3A4, comprising administering to a subject in need of such treatment an effective amount of a combination of said therapeutic compound and a Imidazole Derivative or pharmaceutically acceptable salt thereof.

The present invention also provides methods that may be, or are believed to be, useful for improving the pharmacokinetics of a therapeutic compound that is metabolized by other members of CYP3A, comprising administering to a subject in need of such treatment an effective amount of a combination of said therapeutic compound and a Imidazole Derivative or pharmaceutically acceptable salt thereof. In one embodiment, the therapeutic compound is metabolized by CYP3A5. In another embodiment, the therapeutic compound is metabolized by CYP3A7. In another embodiment, the therapeutic compound is metabolized by CYP3A743.

In one embodiment, the therapeutic compound whose pharmacokinetics are being improved is an anti-HIV drug.

In another embodiment, the therapeutic compound whose pharmacokinetics are being improved is an HIV protease inhibitor.

In still another embodiment, the therapeutic compound whose pharmacokinetics are being improved is an HIV integrase inhibitor.

In another embodiment, the therapeutic compound whose pharmacokinetics are being improved is a nucleoside reverse transcriptase inhibitor (nRTI).

In yet another embodiment, the therapeutic compound whose pharmacokinetics are being improved is a non-nucleoside reverse transcriptase inhibitor (nnRTI).

Combination Therapy

When administering a combination of a Imidazole Derivative and one or more anti-HIV drugs to a subject, the Imidazole Derivative and anti-HIV drug may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Imidazole Derivative and the anti-HIV drug(s) may be present in fixed amounts (dosage amounts) in a single dosage unit (e.g., a capsule, a tablet, and the like).

In one embodiment, the Imidazole Derivative is administered during a time when the anti-HIV drug(s) exert their prophylactic or therapeutic effect, or vice versa.

In another embodiment, the Imidazole Derivative and the anti-HIV drug(s) are administered in doses commonly employed when such agents are used as monotherapy for treating a viral infection.

In another embodiment, when administered in combination with a Imidazole Derivative, the anti-HIV drug(s) are administered in doses lower than the doses commonly employed when such agents are used as monotherapy for treating HIV infection. A lower dosage or less frequent administration of the anti-HIV drug(s) may reduce the toxicity of therapy without reducing the efficacy of therapy.

In one embodiment, the at least one Imidazole Derivative and the anti-HIV drug(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

In one embodiment, the administration of a Imidazole Derivative and the anti-HIV drug(s) may inhibit the resistance of the HIV infection to one or more of the agents being administered.

Anti-HIV Drugs

An "anti-HIV drug," as defined herein, is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV drug is effective in treating, preventing, or delaying the onset or progression of HIV infection or AIDS and/or diseases or conditions arising therefrom or associated therewith. For example, the Imidazole Derivatives of Formula (I) can be effectively administered, whether at periods of pre-exposure and/or post-exposure, in combination with effective amounts of one or more anti-HIV drugs selected from anti-HIV drugs, immunomodulators, antiinfectives, useful for treating HIV infection or AIDS. Suitable HIV antivirals for use in combination with the compounds of the present invention include, for example, those listed in Table A below.

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Dolutegravir | PI |
| efavirenz, EFV, Sustiva ®, Stocrin ® | nnRTI |

TABLE A-continued

| Name | Type |
|---|---|
| efavirenz + emtricitabine + tenofovir DF, Atripla ® | nnRTI + nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| MK-5172 | PI |
| Narlaprevir | PI |
| nelfinavir, Viracept ® | PI |
| nevirapine, NVP, Viramune ® | nnRTI |
| raltegravir, MK-0518, Isentress ® | InI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |
| TMC647055 | nnRTI |
| MK-7009 (vaniprevir) | PI |
| ABT450 (Verupravir) | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

In one embodiment, the one or more anti-HIV drugs are selected from raltegravir, lamivudine, abacavir, ritonavir, dolutegravir, atazanavir, elvitegravir and lopinavir.

In another embodiment, the compound of formula (I) is used in combination with a single anti-HIV drug which is raltegravir.

In another embodiment, the compound of formula (I) is used in combination with a single anti-HIV drug which is lamivudine.

In still another embodiment, the compound of formula (I) is used in combination with a single anti-HIV drug which is atazanavir.

In another embodiment, the compound of formula (I) is used in combination with a single anti-HIV drug which is darunavir.

In yet another embodiment, the compound of formula (I) is used in combination with a single anti-HIV drug which is dolutegravir.

In another embodiment, the compound of formula (I) is used in combination with a single anti-HIV drug which is elvitegravir.

In one embodiment, the compound of formula (I) is used in combination with two anti-HIV drugs which are lamivudine and abacavir.

In another embodiment, the compound of formula (I) is used in combination with two anti-HIV drugs which are darunavir and raltegravir.

In another embodiment, the compound of formula (I) is used in combination with two anti-HIV drugs which are atazanavir and raltegravir.

In still another embodiment, the compound of formula (I) is used in combination with two anti-HIV drugs which are ritonavir and lopinavir.

In another embodiment, the compound of formula (I) is used in combination with two anti-HIV drugs which are lamivudine and raltegravir.

In one embodiment, the compound of formula (I) is used in combination with three anti-HIV drug which are abacavir, lamivudine and raltegravir.

In another embodiment, the compound of formula (I) is used in combination with three anti-HIV drug which are lopinavir, ritonavir and raltegravir.

In one embodiment, the present invention provides pharmaceutical compositions comprising (i) a compound of formula (I) or a pharmaceutically acceptable salt thereof (ii) a pharmaceutically acceptable carrier; and (iii) one or more additional anti-HIV drugs selected from lamivudine, abacavir, ritonavir and lopinavir, or a pharmaceutically acceptable salt thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt thereof and (ii) one or more additional anti-HIV drugs selected from raltegravir, lamivudine, abacavir, atazanavir, darunavir, ritonavir and lopinavir, or a pharmaceutically acceptable salt thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV drugs is not limited to the HIV antivirals listed in Table A, but includes in principle any combination with any drug or pharmaceutical composition useful for the treatment or prophylaxis of AIDS. The anti-HIV drugs and other agents will typically be employed in these combinations in their conventional dosage ranges and regimens as reported in the art, including, for example, the dosages described in the *Physicians' Desk Reference*, Thomson P D R, Thomson P D R, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Imidazole Derivative(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Compositions and Administration

Due to their activity, the Imidazole Derivatives are useful in veterinary and human medicine. As described above, the Imidazole Derivatives are useful for inhibiting CYP3A4; improving the pharmacokinetics of a therapeutic compound that is metabolized by CYP3A4; and in combination with one or more anti-HIV agents for treating or preventing HIV infection in a subject in need thereof.

When administered to a subject, the Imidazole Derivatives can be administered as a component of a composition that comprises a pharmaceutically acceptable carrier or vehicle. The present invention provides pharmaceutical compositions comprising an effective amount of at least one Imidazole Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Imidazole Derivatives are administered orally.

In another embodiment, the Imidazole Derivatives are administered intravenously.

In one embodiment, the present invention provides compositions comprising a Compound of Formula (I) or a pharmaceutically acceptable salt thereof, and a pharmaceutically acceptable carrier.

In one embodiment, a pharmaceutical preparation comprising at least one Imidazole Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Imidazole Derivative(s) by weight or volume. In various embodiments, the present compositions can contain, in one embodiment, from about 1% to about 70% or from about 5% to about 60% of the Imidazole Derivative(s) by weight or volume.

The Imidazole Derivatives can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Imidazole Derivatives will be regulated according to the judgment of the attending clinician considering such factors as age, condition and size of the subject as well as severity of the symptoms being treated. The compositions of the invention can further comprise one or more additional therapeutic agents, selected from those listed above herein. Accordingly, in one embodiment, the present invention provides compositions comprising: (i) a Compound of Formula (I) or a pharmaceutically acceptable salt thereof; (ii) a therapeutic compound that is metabolized by CYP3A4; and (iii) a pharmaceutically acceptable carrier. In another embodiment, the present invention provides compositions comprising: (i) a Compound of Formula (I) or a pharmaceutically acceptable salt thereof; (ii) one or more anti-HIV drugs; and (iii) a pharmaceutically acceptable carrier, wherein the amounts in the composition are together effective to treat HIV infection.

In another embodiment, the present invention provides compositions comprising a Compound of Formula (I) or a pharmaceutically acceptable salt thereof, a pharmaceutically acceptable carrier, and one or more anti-HIV drugs, wherein said anti-HIV drugs are selected from raltegravir, lamivudine, abacavir, atazanavir, darunavir, lopinavir and ritonavir.

In another embodiment, the present invention provides compositions comprising a Compound of Formula (I) or a pharmaceutically acceptable salt thereof, a pharmaceutically acceptable carrier, and one or more anti-HIV drugs, wherein said anti-HIV drugs are selected from raltegravir, atazanavir, darunavir, lopinavir and ritonavir.

In still embodiment, the present invention provides compositions comprising a Compound of Formula (I) or a pharmaceutically acceptable salt thereof, a pharmaceutically acceptable carrier, and raltegravir.

Kits

In one aspect, the present invention provides a kit comprising a therapeutically effective amount of at least one Imidazole Derivative, or a pharmaceutically acceptable salt, solvate, ester or prodrug of said compound and a pharmaceutically acceptable carrier, vehicle or diluent.

In another aspect the present invention provides a kit comprising an amount of at least one Imidazole Derivative, or a pharmaceutically acceptable salt, solvate, ester or prodrug of said compound and a therapeutic compound that is metabolized by CYP3A4. In one embodiment, the Imidazole Derivatives and the therapeutic compound that is metabolized by CYP3A4 are provided in the same container. In one embodiment, the Imidazole Derivatives and the therapeutic compound that is metabolized by CYP3A4 are provided in separate containers.

In another aspect the present invention provides a kit comprising an amount of at least one Imidazole Derivative, or a pharmaceutically acceptable salt, solvate, ester or prodrug of said compound and an amount of at least one anti-HIV drug listed above, wherein the amounts of the two or more active ingredients result in a desired therapeutic effect. In one embodiment, the Imidazole Derivatives and the one or more anti-HIV drugs are provided in the same container. In one embodiment, the Imidazole Derivatives and the one or more anti-HIV drugs are provided in separate containers.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A-L below. Alternative synthetic pathways and analogous structures will be apparent to those skilled in the art of organic synthesis.

Scheme A shows methods useful for making compounds of formula A6, which are useful intermediates for the synthesis of compounds of Formula (I), wherein Q is carbon.

Scheme A

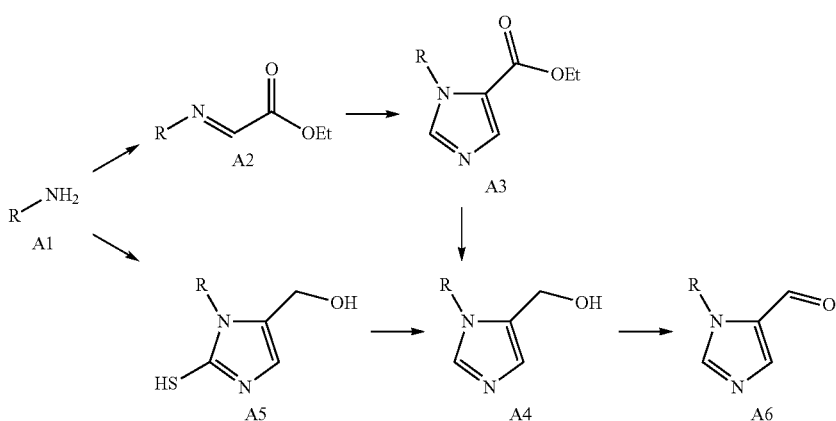

Amines of formula A1 can be condensed with an aldehyde to provide intermediates of formula A2 which can undergo a cyclization reaction with a reagent such as TosMIC to provide compounds f formula A3. Intermediate A3 can subsequently be reduced with a hydride reducing agent such as LiBH$_4$ to provide carbinols of formula A4. Compounds f formula A4 can alternatively be prepared in a two-step procedure involving the condensation of amine A1 with 1,3-dihydroxyacetone dimer and KSCN to provide the thio-imidazole comopounds of formula A5 which can then be oxidized with a reagent such as hydrogen peroxide to provide intermediate A4. Primary alcohols of formula A4 can then be oxidized with reagents such as MnO$_2$ to provide the key intermediates of formula A6.

Scheme B shows methods useful for making the compounds of formula B3, which are useful intermediates for the synthesis of compounds of Formula (I), wherein Q is nitrogen.

Scheme B

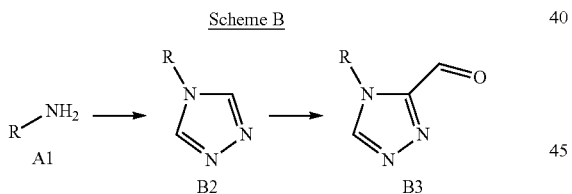

Amines of formula A1 can be cyclocondensed with 1,2-diformylhydrazine to provide 1,2,4-triazoles of formula B2 which can subsequently be converted to the aldehydes of formula B3 using standard formylation reagents, such as DMF and POCl$_3$.

Scheme C shows methods useful for making the compounds of formula C5, which correspond to the compounds of Formula (I), wherein Q is carbon and X is a substituted carbon.

Scheme C

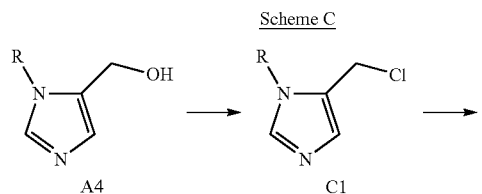

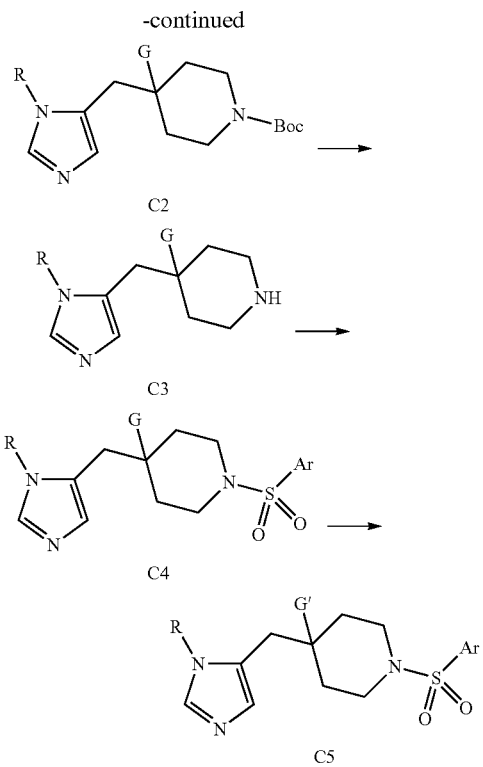

Carbinols of formula A4 can be activated for alkylation of a piperidine derivative by conversion to the chloride C1 which can then be added to the anion of a 4-substituted piperidine in which the G group is an anion stabilizing group such as nitrile or ester. Deprotection of the piperidine nitrogen can afford compounds of formula C3 which can be sulfonylated to provide compounds of formula C4. The G group may undergo further modification using standard functional group transforming reactions to provide analogs of formula C5.

Scheme D shows methods useful for making compounds of formulas D3, D6 and D9, which correspond to the compounds of Formula (I), wherein Q is carbon; X is hydroxy or ether; and Y is H, alkyl or trifluoromethyl.

Scheme D

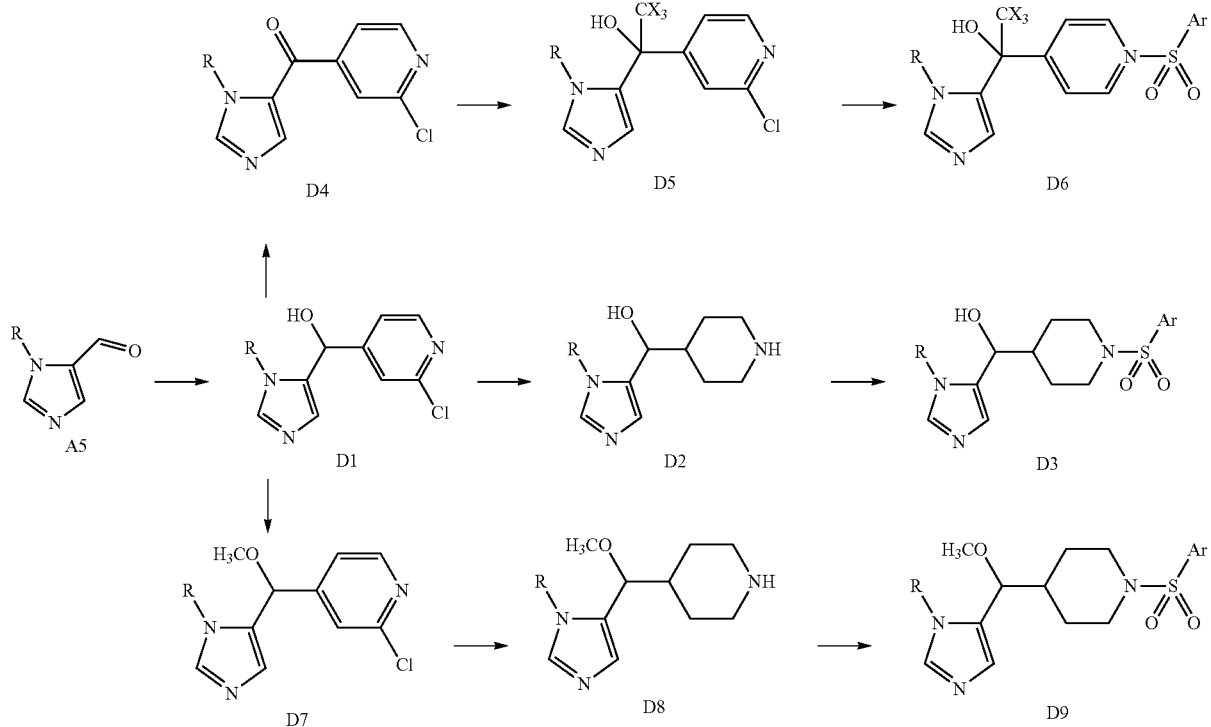

Aldehydes of formula A5 can be reacted with the anion of 2-chloro-4-methylpyridine to provide carbinol D1 which can be reduced using hydrogenating conditions and a catalyst such as $PtO_2$ to provide piperidine compounds of formula D2. A compound of formula D2 can then be sulfonylated with an appropriately substituted arylsulfonyl chloride and a base such as triethylamine to provide the compounds of formula D3. Additionally, carbinols of formula D1 can be oxidized with a reagent such as $MnO_2$ to the ketones of formula D4 which can then be treated with methyl (X=H) or trifluoromethyl (X=F) nucleophiles to provide D5 which can be hydrogenated and sulfonylated to provide compounds of formula D6. Alternatively, carbinols of formula D1 can be alkylated using a metal hydride base and electrophile, such as $CH_3I$ to provide ethers D7 which can be converted to compounds of formula D9 using chemistry described for the synthesis of the compounds of formulas D3 and D6.

Scheme E shows methods useful for making compounds of formulas E3 and E6, which correspond to the compounds of Formula (I), wherein Q is carbon and X is carbon which can be linked to Z through a —$CH_2$— bridge.

Scheme E

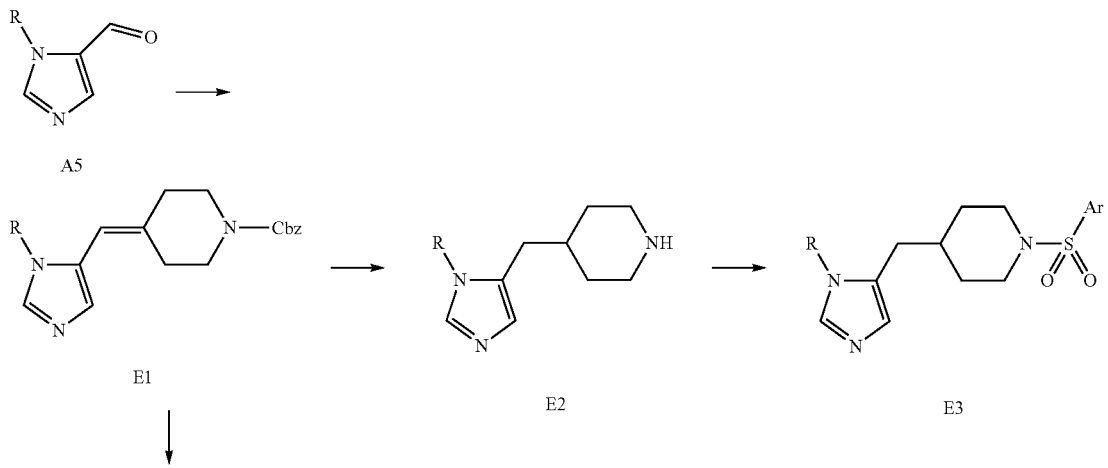

Aldehydes of formula A5 can undergo a McMurray coupling reaction with an appropriately substituted 4-piperidinone derivative using reagents such as zinc dust and titanium(IV)chloride to provide olefins of formula E1 which can be reduced and deprotected using hydrogenation conditions with a catalyst such as Pd(OH)$_2$ to provide piperidines of formula E2. Standard conditions for the sulfonylation of secondary amines (ArSO$_2$Cl, Et$_3$N) can be used to provide targets of formula E3. Alternatively, olefins of formula E1 can be cyclopropanated using well-known chemistry (such as (CH$_3$)$_3$S$^+$I$^-$ and NaH) to provide the spirocycles of formula E4 which can then be converted to the desired compounds of formula E6 using conditions similar to those described for the preparation of compounds of formula E3.

Scheme F shows methods useful for making compounds of formula F3 and F7, which correspond to the compounds of Formula (I), wherein Q is carbon or nitrogen; X is nitrogen; and Z is H or methyl.

Aldehydes of formula A5 can be reductively aminated with a piperazine derivative using standard conditions using a dehydrating agent such as Ti(OiPr)$_4$ and a reducing agent such as NaBH(OAc)$_3$ to provide intermediates of formula E1 which can subsequently be deprotected and sulfonylated to provide targets of formula E3 using conditions described in the schemes above. Aldehyde A5 can also be converted to the secondary alcohols of formula E4 by reaction with a methyl nucleophile such as CH$_3$MgBr. Ketone E5 can be formed from oxidizing E4 with an oxidizing agent such as MnO$_2$ which can then undergo reductive amination, deprotection, and sulfonylation following chemistry described above to provide analogs of formula E7.

Scheme G shows methods useful for making compounds of formula G2, which correspond to the compounds of Formula (I), wherein B is carbon and Z is CN.

Aldehydes of formula A5 can be converted to the alpha-aminonitriles of formula G1 using a suitably protected piperazine and a cyanide source such as KCN. Compounds of formula G2 can be obtained after deprotection of the Boc group and sulfonylation of the resulting amine using standard conditions (such as ArSO$_2$Cl and Et$_3$N) to provide targets of formula G2.

Scheme H shows methods useful for making compounds of formula H2 and H4, which correspond to the compounds of Formula (I), wherein B is carbon; X is nitrogen; and Z is $(CH_2)_nOR^a$ wherein n is 1 or 2.

Scheme I shows methods useful for making compounds of formula I5, which correspond to the compounds of Formula (I), wherein Q is carbon; X is nitrogen; and $R^1$ and Z are joined to form a —$CH_2OCH_2$— bridge.

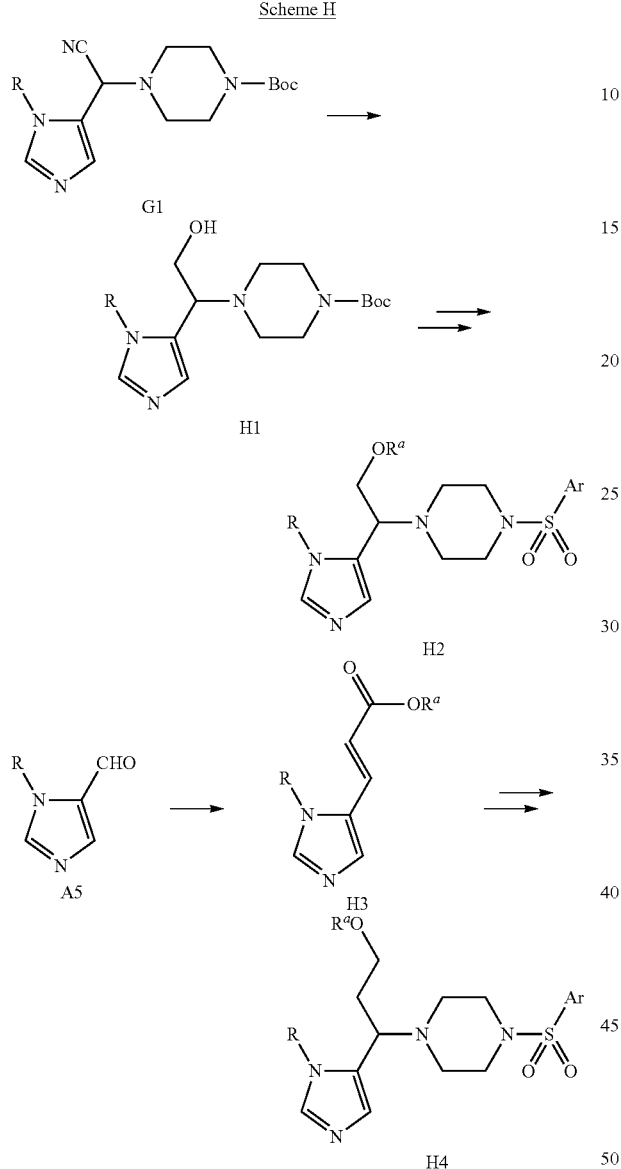

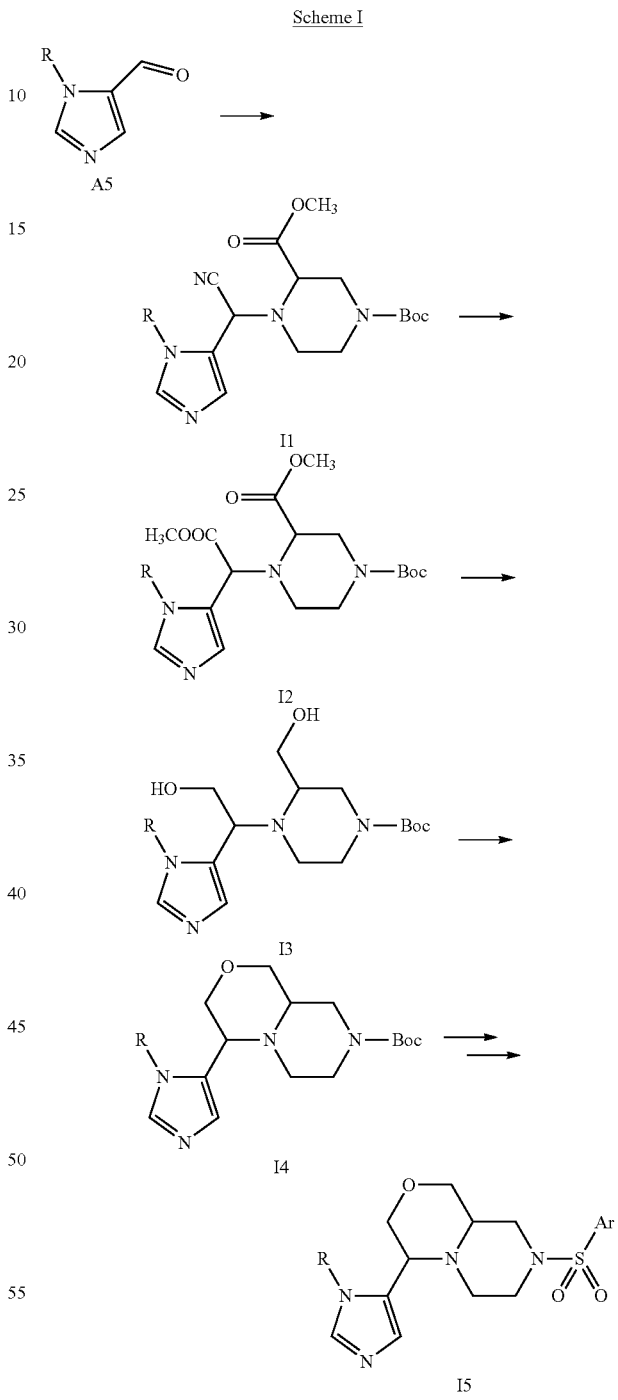

Nitriles of formula G1 can be converted to its carboxylic ester then reduced using standard conditions. The resulting alcohol can be alkylated to intermediates of formula H2 ($R^a$=alkyl) using standard conditions or converted to the compounds of formula H2 after deprotection of the Boc group and sulfonylation of the resulting amine using standard conditions such as $ArSO_2Cl$ and a tertiary amine base. Alternatively, aldehydes of formula A5 can be olefinated using standard Horner-Emmons chemistry to provide the unsaturated esters of formula H3 which can then undergo a Michael addition with a suitably protected piperazine analog to provide a β-substituted ester which can subsequently be reduced using known conditions for the reduction of esters to primary alcohols such as $LiBH_4$. The resulting alcohol can be further functionalized to the compounds of formula H4 using methods described above.

Aldehyde A5 can be converted to the nitrile ester I1 using chemistry described for the preparation of G1. Nitrile I1 can be transformed to the diester analog I2 under acidic conditions which can then be converted to diol I3 using a hydride reducing agent such as $LiBH_4$. Ring closure to provide compounds of formula I4 can be affected by activating one of the alcohol functional groups with a reagent such as toluene sulfonyl chloride followed by deprotonating the second alcohol with a metal hydride base such as NaH. Final targets of formula I5 can be obtained after deprotection of the Boc group and sulfonylation of the resulting piperazine amine using standard conditions such as ArSO₂Cl and a tertiary amine base.

Scheme J shows methods useful for making compounds of formula J5, which correspond to the compounds of Formula (I), wherein Q is carbon; X is nitrogen; and $R^1$ and Z are joined to form a —CH₂CH₂CH₂— bridge.

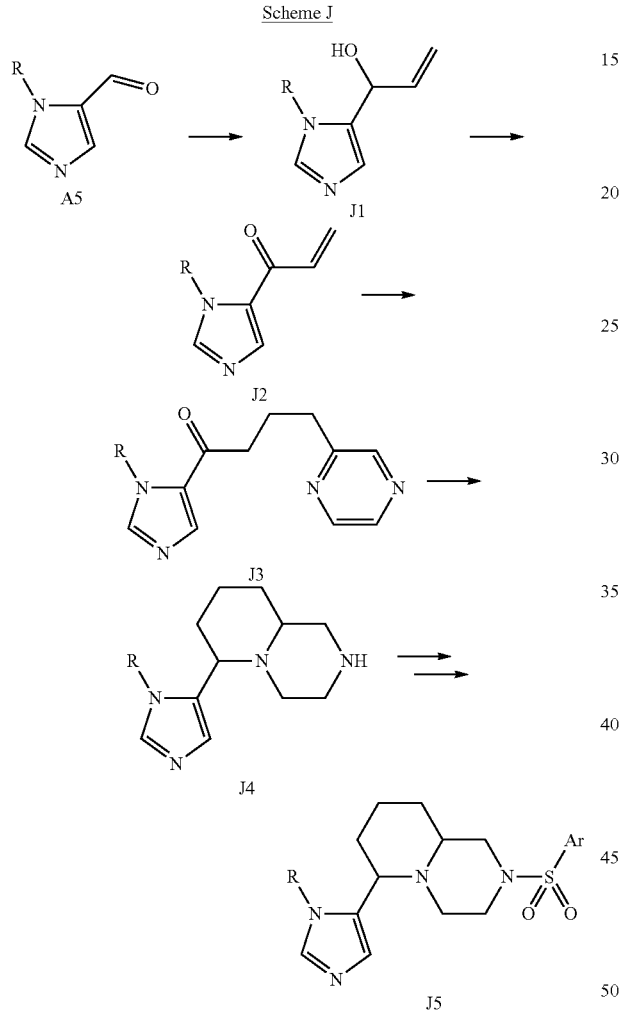

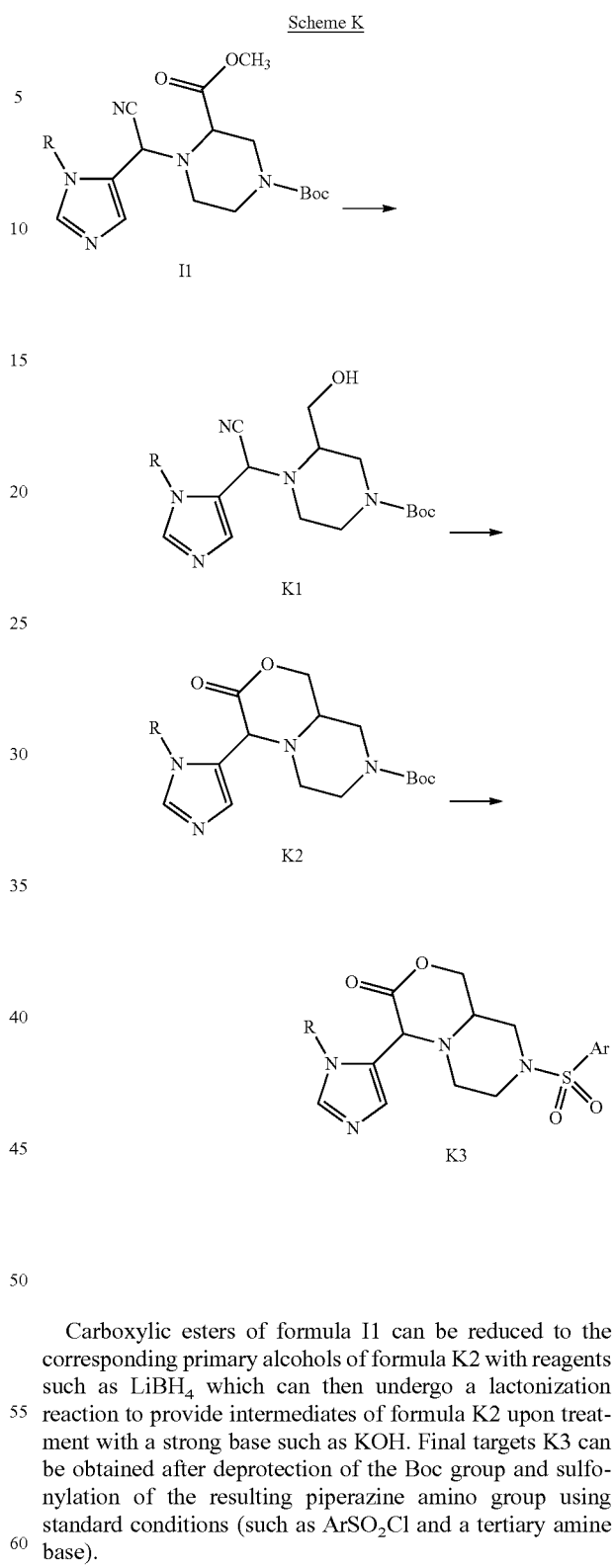

Aldehydes of formula A5 can be converted to the α,β-unsaturated ketones of formula J2 by a standard two-step procedure involving the addition of a vinyl Grignard reagent and oxidation of the resulting carbinol with a reagent such as MnO₂. Intermediates of formula J2 can undergo a Michael addition with the anion derived from metallating 2-methyl-1,4-pyrazine to form ketones of formula J3 which can then undergo reductive cyclization after treatment with a metal catalyst under a hydrogen atmosphere. Standard methodology for sulfonylating secondary amines can give targets of formula J5.

Scheme K shows methods useful for making compounds of formula K3, which correspond to the compounds of Formula (I), wherein Q is carbon; X is nitrogen; and $R^1$ and Z are joined to form a —CH₂OC(=O)— bridge.

Carboxylic esters of formula I1 can be reduced to the corresponding primary alcohols of formula K2 with reagents such as LiBH₄ which can then undergo a lactonization reaction to provide intermediates of formula K2 upon treatment with a strong base such as KOH. Final targets K3 can be obtained after deprotection of the Boc group and sulfonylation of the resulting piperazine amino group using standard conditions (such as ArSO₂Cl and a tertiary amine base).

Scheme L shows methods useful for making the intermediates of formula L2 and L4, which correspond to the compounds of Formula (I), wherein Q is carbon; X is nitrogen; and $R^1$ and Z are joined to form a —C(=O)NR$^a$CH₂— lactam bridge or a —CH₂N(CH₃)CH₂— amine bridge.

Scheme L

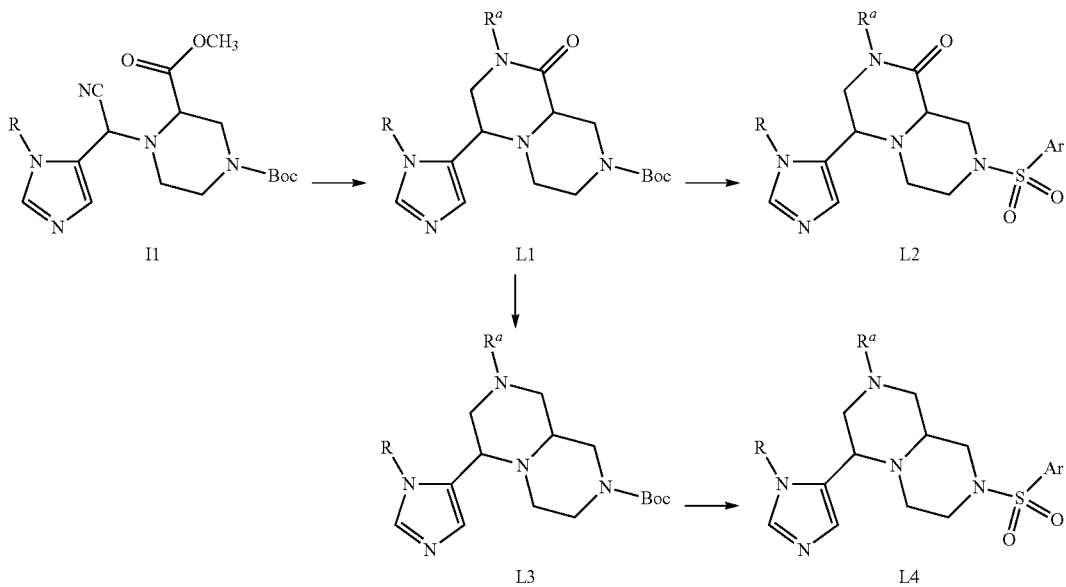

Nitriles of formula I1 can undergo reductive lactamization using known conditions for the conversion of a nitrile to a primary amine such as catalytic hydrogenation using a metal such as nickel as the catalyst. The resulting lactam NH can be alkylated to intermediates of formula L1 ($R^a$=alkyl) using standard conditions or converted to the final targets of formula L2 ($R^a$=H) using methods described above. Alternatively, intermediate lactams of formula L1 can be reduced to triamines of formula L3 using a metal hydride reagent such as LiAlH$_4$. Final targets of formula L4 can be obtained after deprotection of the Boc group and sulfonylation of the resulting amine using standard conditions (such as ArSO$_2$Cl and a tertiary amine base).

One skilled in the art of organic synthesis will recognize that the synthesis of the Compounds of Formula (I) may require protection of certain functional groups (i.e., derivatization for the purpose of chemical compatibility with a particular reaction condition). Suitable protecting groups for the various functional groups of these compounds and methods for their installation and removal are well known in the art of organic chemistry. A summary of many of these methods can be found in Greene et al., *Protective Groups in Organic Synthesis*, Wiley-Interscience, New York, (1999).

One skilled in the art of organic synthesis will also recognize that one route for the synthesis of the Compounds of Formula (I) may be more desirable depending on the choice of appendage substituents. Additionally, one skilled in the art will recognize that in some cases the order of reactions may differ from that presented herein to avoid functional group incompatibilities and thus adjust the synthetic route accordingly.

The preparation of some intermediates useful for making the Compounds of Formula (I) have been described in the literature and in compendia such as "Comprehensive Heterocyclic Chemistry" editions I, II and III, published by Elsevier and edited by A. R. Katritzky & R. J K Taylor. Manipulation of the required substitution patterns have also been described in the available chemical literature as summarized in compendia such as "Comprehensive Organic Chemistry" published by Elsevier and edited by DH R. Barton and W. D. Ollis; "Comprehensive Organic Functional Group Transformations" edited by edited by A. R. Katritzky & R. J K Taylor and "Comprehensive Organic Transformation" published by Wily-CVH and edited by R. C. Larock.

The Compounds Formula (I) may contain one or more silicon atoms. The compounds contemplated in this invention in general can be prepared using the carba-analog methodology unless otherwise noted. A recent review of the synthesis of silicon containing compounds can be found in "Silicon Chemistry: from Atom to Extended Systems", Ed P. Jutzi & U. Schubet; ISBN 978-3-527-30647-3. Preparation of silyl containing amino acids has been described. See Bolm et al., *Angew. Chem. Int Ed.*, 39:2289 (2000). Descriptions of improved cellular update (Giralt, J. Am. Chem. Soc., 128:8479 (2006)) and reduced metabolic processing of silyl containing compounds have been described (Johansson et al., *Drug Metabolism & Disposition*, 38:73 (2009)).

The starting materials used and the intermediates prepared using the methods set forth in Schemes A-L may be isolated and purified if desired using conventional techniques, including but not limited to filtration, distillation, crystallization, chromatography and alike. Such materials can be characterized using conventional means, including physical constants and spectral data.

EXAMPLES

General Methods

Solvents, reagents, and intermediates that are commercially available were used as received. Reagents and intermediates that are not commercially available were prepared in the manner as described below. $^1$H NMR spectra were obtained on a Varian VNMR System 400 (400 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer and Shimadzu SCL-10A LC column: Altech platinum C18, 3 micron, 33 mm×7 mm ID; gradient flow: 0 minutes—10% CH₃CN, 5 minutes—95% CH₃CN, 5-7 minutes—95% CH₃CN, 7 minutes—stop. The retention time and observed parent ion are given. Flash column chromatography was performed using pre-packed normal phase silica from Biotage, Inc. or bulk silica from Fisher Scientific. Unless otherwise indicated, column chromatography was performed using a gradient elution of hexanes/ethyl acetate, from 100% hexanes to 100% ethyl acetate.

Example 1

Preparation of Compound 1

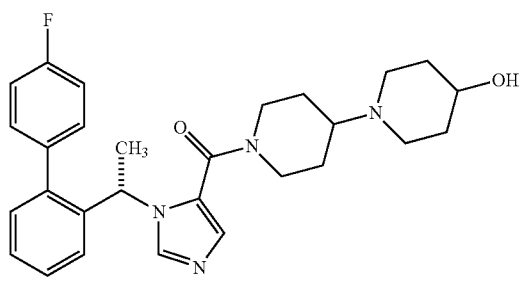

Step A—Preparation of Int 1-1

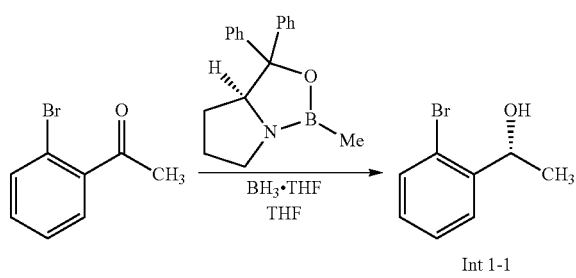

Into a 500-mL 4-necked round-bottom flask purged and maintained with an inert atmosphere of nitrogen was placed (3aS)-1-methyl-3,3-diphenyl-hexahydropyrrolo[1,2-c][1,3,2]oxazaborole (1M, 6.25 mL, 0.05 equiv) and THF (125 mL). This was followed by the addition of borane-THF (1M, 150 mL, 1.20 equiv) dropwise with stirring at −30° C. The resulting solution was stirred for 30 min at −30° C. To this was added a solution of 1-(2-bromophenyl)ethan-1-one (25 g, 0.13 mol, 1.0 equiv) in THF (625 mL) dropwise with stirring at −30° C. The resulting solution was stirred for 30 min at −30° C., then quenched by the addition of 60 mL of methanol at 0° C. The resulting mixture was concentrated and the residue was applied onto a silica gel column and eluted with ethyl acetate/petroleum ether (1:10). This resulted in (1R)-1-(2-bromophenyl)ethan-1-ol as colorless oil. MS-ESI (m/z): 309.1 (M+1). ¹H NMR (CDCl₃): δ 7.58 (dd, J=1.5, 7.8 Hz, 1H), 7.50 (dd, J=1.5, 7.8 Hz, 1H), 7.33 (dt, J=1.1, 7.5 Hz, 1H), 7.11 (dt, J=1.7, 7.5 Hz, 1H), 5.21 (m, 1H), 2.05 (s, 1H), 1.47 (d, J=6.4 Hz, 3H).

Step B—Preparation of Int 1-2

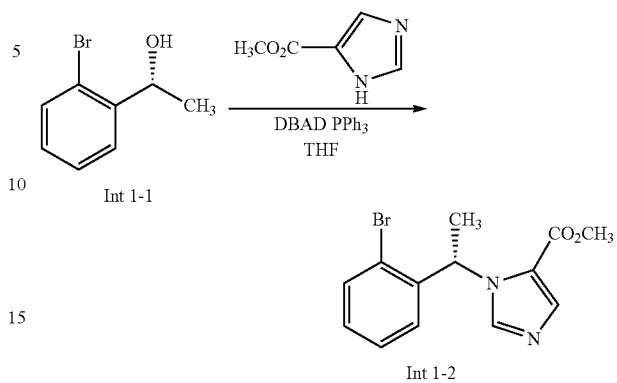

Into a 300-mL 4-necked round-bottom flask purged and maintained with an inert atmosphere of nitrogen was placed (1R)-1-(2-bromophenyl)ethan-1-ol (Int 1-1; 8.6 g, 42.8 mmol, 1.0 equiv), methyl 1H-imidazole-5-carboxylate (4.85 g, 38.5 mmol, 0.90 equiv), PPh₃ (15.5 g, 59 mmol, 1.4 equiv) and THF (100 mL). This was followed by the addition of a solution of DBAD (13.7 g, 1.4 equiv) in THF (35 mL) dropwise with stirring at −70° C. The resulting solution was stirred for 2 h at −70° C. and an additional 2 h at 0° C. The reaction was then quenched by the addition of 100 mL of water at 0° C. The resulting solution was extracted with 3×100 mL of ethyl acetate. The organic layers were combined, washed with 1×100 mL of brine, dried over anhydrous sodium sulfate and concentrated under vacuum. The residue was applied onto a silica gel column and eluted with ethyl acetate/petroleum ether (1:10-1:5). This resulted in Int 1-2 as yellow oil. ¹H NMR (CDCl₃): δ 7.81 (s, 1H), 7.69 (s, 1H), 7.58 (dd, J=1.4, 7.8 Hz, 1H), 7.27 (dt, J=1.5, 7.8 Hz, 1H), 7.17 (dt, J=1.1, 7.5 Hz, 1H), 6.81 (dt, J=1.7, 7.5 Hz, 1H), 6.49 (q, J=7.1 Hz, 1H), 3.75 (s, 3H), 1.83 (d, J=6.4 Hz, 3H).

Step C—Preparation of Int 1-3

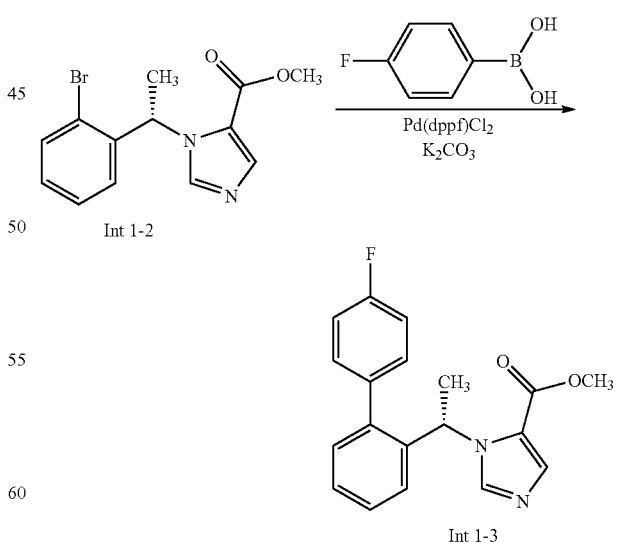

A round bottom flask was charged with Int 1-2 (12 g, 39 mmol), (4-fluorophenyl)boronic acid (6.5 g, 47 mmol), Pd(dppf)Cl₂ (1.43 g, 2 mmol) and K₂CO₃ (13.5 g, 98 mmol) in toluene/ethanol/H₂O (24 mL/12 mL/12 mL), and the mixture was then allowed to stir at 90° C. overnight. When TLC (petroleum ether:ethyl acetate=2:1) showed the reaction was complete, the mixture was cooled to room temperature and then concentrated in vacuo. The residue was extracted with ethyl acetate (10 mL×5) and the combined organic layer was dried over anhydrous sodium sulfate and filtered. The filtrate was concentrated in vacuo to provide the residue which was purified using silica gel column chromatography (petroleum ether:ethyl acetate=20:1 to 10:1) to provide the pure ester Int 1-3 as white solid. MS (APCI): M/Z (M+1) 325.1. $^1$H NMR (CDCl$_3$): δ 7.60 (s, 1H), 7.43 (s, 1H), 7.34-7.39 (m, 2H), 7.17-7.24 (m, 2H), 6.95-7.06 (m, 4H), 6.67-6.32 (m, 1H), 3.70 (s, 3H), 1.39 (d, J=6.4 Hz, 3H).

Step D—Preparation of Int 1-4

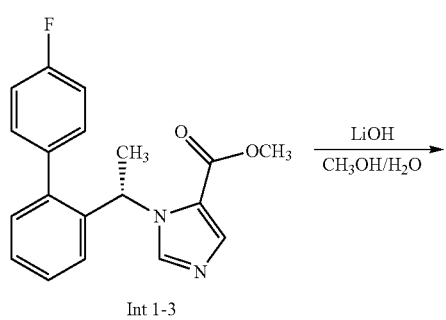

Int 1-3

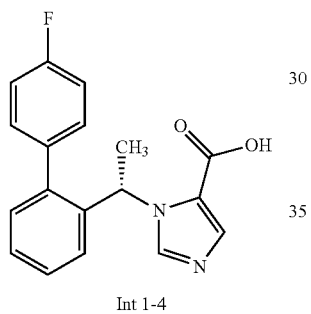

Int 1-4

To a solution of Int 1-3 (11 g, 35 mmol) in methanol (40 mL) was added 7.3 g (178 mmol) of LiOH in H$_2$O (10 mL). The resulting mixture was allowed to stir at room temperature overnight before the mixture was concentrated in vacuo. The residue was treated with 3N HCl to pH~6.5. The aqueous layer was extracted with ethyl acetate (10 mL×6) and the combined organic layer was dried over anhydrous sodium sulfate and filtered. The filtrate was concentrated in vacuo to provide the pure carboxylic acid Int 1-4. MS (APCI): M/Z (M+1) 311.2 $^1$H NMR (CDCl$_3$): δ 7.66 (s, 1H), 7.49 (s, 1H), 7.41 (s, 1H), 7.32-7.40 (m, 1H), 7.17 (m, 1H), 7.10 (m, 1H), 6.81 (dt, J=1.7, 7.5 Hz, 1H), 6.99 (t, J=8.4 Hz, 1H), 6.35 (q, J=7.9 Hz, 1H), 1.63 (d, J=6.4 Hz, 3H).

Step E—Preparation of Compound 1

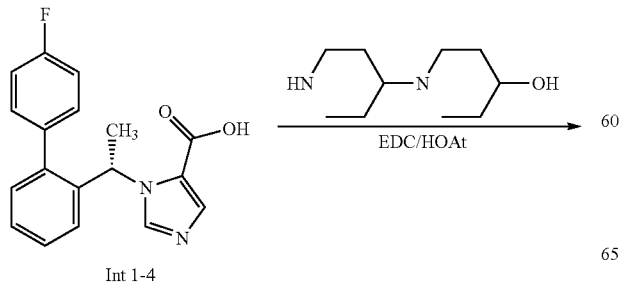

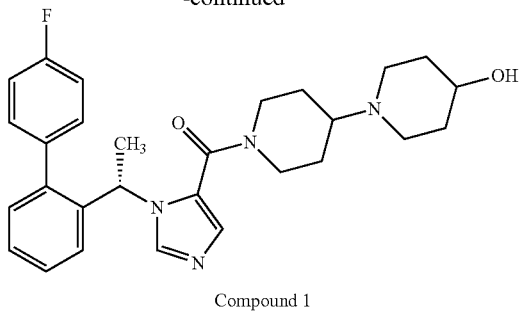

Compound 1

To a solution of Int 1-4 (2.5 g, 8.1 mmol) in 20 mL of DCM was added 1.5 g (8.1 mmol) of 1,4'-bipiperidin-4-ol (ChemBridge), 2.3 g (12.1 mmol) of EDC, 0.36 g (2.7 mmol) of HOAt and 4.2 mL (24 mmol) of DIPEA. The mixture was stirred over 18 h then diluted with 20 mL of DCM. The reaction mixture was then washed with water (3×) and brine (1×), dried over MgSO$_4$ and filtered. Column chromatography (9:1 DCM/CH$_3$OH) afforded 2.3 g of Compound 1 as a white solid. MS-ESI (m/z): 477.5 (M+1)$^+$. $^1$H NMR (CDCl$_3$) δ 7.68 (s, 1H), 7.27-7.32 (m, 4H), 7.10-7.16 (m, 4H), 6.77 (bs, 1H), 5.99 (d, J=6.6 Hz, 1H), 4.09-4.14 (m, 2H), 3.58-3.65 (m, 2H), 2.65-2.78 (m, 2H), 2.51-2.64 (m, 4H), 2.20-2.34 (m, 2H), 1.71-1.93 (m, 5H), 1.65 (d, J=6.2 Hz, 3H), 1.18-1.25 (m, 2H).

Example 2

Preparation of Compound 2

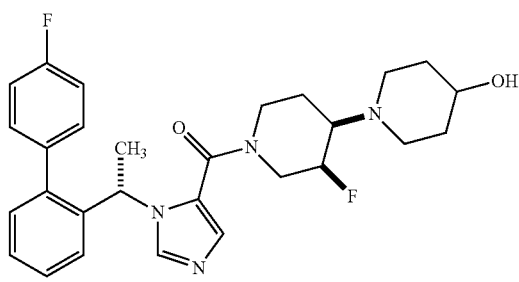

2

Step A—Preparation of Int 2-1

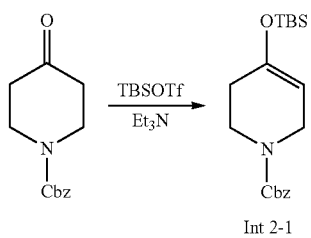 [SMILES: "Et3N" ; "TBSOTf" ; O=C1CCN(C(=O)OCc2ccccc2)CC1 ; CC(C)(C)[Si](C)(C)OC1=CCN(C(=O)OCc2ccccc2)CC1]

Int 2-1

A round bottom flask was charged with N-Cbz-piperidone (4.6 g, 19.7 mmol), Et$_3$N (8.5 mL), TBSOTf (7.8 g, 29.5 mmol) and dichloromethane (50 mL), the mixture was allowed to stir at room temperature for an hour. The reaction mixture was then concentrated in vacuo and dissolved in water, the aqueous layer was extracted with petroleum ether. The combined organic layer was dried over anhydrous sodium sulfate and concentrated in vacuo to provide the crude product Int 2-1 which was be used in next step without further purification. MS-ESI (m/z): 348.2 (M+1)+.

Step B—Preparation of Int 2-2

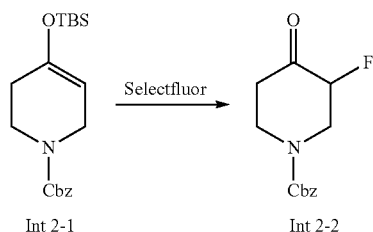 [SMILES: CC(C)(C)[Si](C)(C)OC1=CCN(C(=O)OCc2ccccc2)CC1 ; "Selectfluor" ; O=C1CCN(C(=O)OCc2ccccc2)CC1F]

Int 2-1        Int 2-2

To a mixture of Int 2-1 (3.6 g, 11.7 mmol) in 30 mL of acetonitrile was added Selectfluor (6.2 g, 17.6 mmol) in acetonitrile (20 mL) dropwise and the resulting mixture was allowed to stir at room temperature for 2 hours. The reaction mixture was then poured into water and the aqueous layer was extracted with ethyl acetate. The combined organic layers were dried over anhydrous sodium sulfate and concentrated in vacuo to provide the crude product Int 2-2 which was used in next step without further purification. MS-ESI (m/z): 252.2 (M+1)+.

Step C—Preparation of Int 2-3

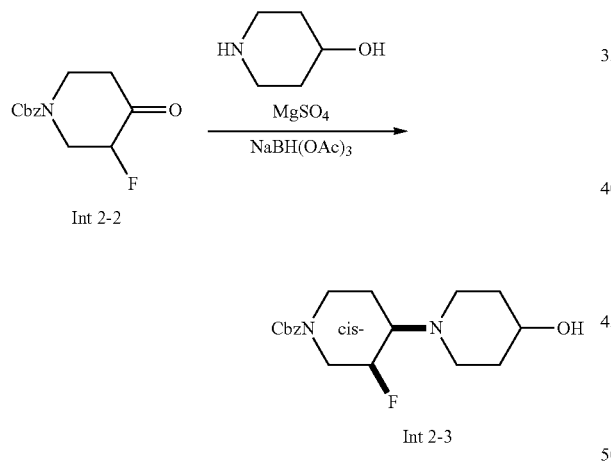

Int 2-3

To a solution of Int 2-2 (2.7 g, 11 mmol) in anhydrous dichloromethane (20 mL) was added piperidin-4-ol (1 g, 10 mmol) and MgSO$_4$ (1.8 g, 15 mmol). The mixture was allowed to stir at room temperature for 2 hours, and then sodium triacetoxyborohydride (2.5 g, 12 mmol) was added. The resulted mixture was allowed to stir at room for additional 2 hours. When LCMS showed the reaction was complete, the mixture was quenched by the addition of water and filtered. The filtrate was extracted with dichloromethane and the combined organic layers were dried over anhydrous sodium sulfate then filtered. The filtrate was concentrated in vacuo to provide the crude product which was column chromatography (ethyl acetate: methanol=9:1) to provide compound Int 2-3 as a mixture of cis diastereomers. MS-ESI (m/z): 337.1 (M+H)+.

Step D—Preparation of Int 2-4

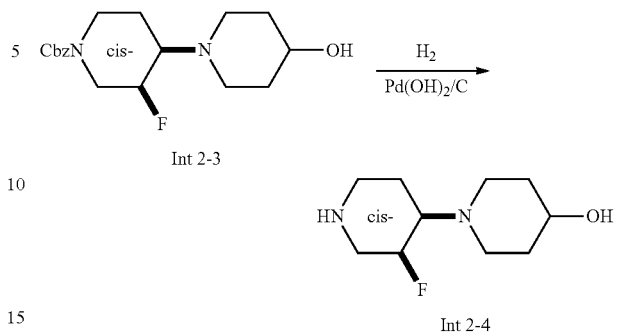

Int 2-3

Int 2-4

A mixture of Int 2-3 (1.6 g, 4.75 mmol) and Pd(OH)$_2$/C (100 mg) in ethanol (10 mL) was allowed to stir at 50° C. under a hydrogen atmosphere (50 psi) overnight. The mixture was then cooled to room temperature and filtered. The filtrate was concentrated in vacuo to provide the crude product Int 2-4 which was used in next step without further purification.

Step E—Preparation of Compound 2

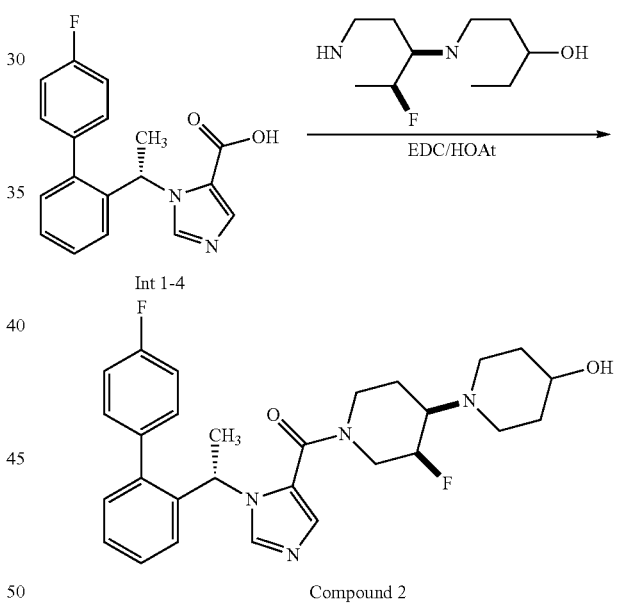

Int 1-4

Compound 2

To a solution of Int 1-4 (600 mg, 1.9 mmol) and triethylamine (390 mg, 3.8 mmol) in DMF (20 mL) was added HATU (1100 mg, 2.9 mmol). The reaction mixture was stirred for 30 mins before compound Int 2-4 (390 mg, 1.9 mmol) was added. The mixture was allowed to stir at room temperature for 2 hours and filtered. The filtrate was purified using preparative-HPLC to provide (500 mg, yield: 52%) of Compound 2 as a white solid. $^1$H NMR (CD$_3$OD) δ: 7.91 (s, 1H), 7.36-7.24 (m, 4H), 7.22-7.11 (m, 4H), 7.03 (d, J=6.8 Hz, 1H), 5.93 (s, 1H), 3.97 (br, 3H), 3.59 (br, 1H), 3.05-2.80 (m, 3H), 2.66 (t, J=13.6 Hz, 1H), 2.61-2.56 (m, 1H), 2.52-2.47 (m, 1H), 2.40 (d, J=7.6 Hz, 2H), 1.84 (br, 3H), 1.74 (d, J=6.4 Hz, 3H), 1.60-1.48 (m, 2H).

MS-ESI (m/z): 495.2 (M+1)+.

Example 3

Preparation of Compounds 3a and 3b

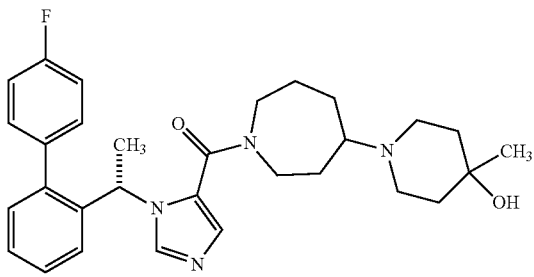

Step A—Preparation of Int 3-1

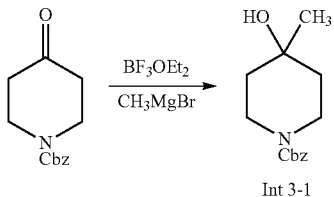

To a solution of Cbz piperidinone (10 g, 43 mmol) and boron trifluoride diethyl etherate (6.7 g, 47 mmol) in dry tetrahydrofuran (100 mL) was added MeMgBr (43 mL, 130 mmol) dropwise under nitrogen atmosphere at 0° C. After the addition was completed, the solution was warmed to room temperature and stirred for another 3 hours. The solution was quenched with water (40 mL) and the aqueous was extracted with ethyl acetate (3×40 mL). The combined organic layer was dried over sodium sulfate then filtered. The filtrate was concentrated in vacuo to provide crude product, which was purified using column chromatography (petroleum ether: ethyl acetate=50:1, 30:1, 10:1) to provide compound Int 3-1 as white solid. MS-ESI (m/z): 250.3 (M+H)$^+$.

Step B—Preparation of Int 3-2

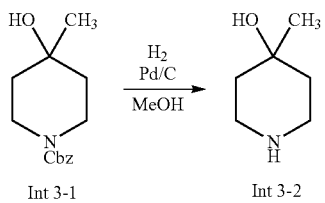

A mixture of the Cbz protected piperidine Int 3-1 (1.5 g, 6.02 mmol) and Pd/C (0.3 g) in methanol (30 mL) was degassed under reduce pressure and purged with hydrogen 3 times. The reaction mixture was stirred under hydrogen (50 psi) at room temperature overnight. The reaction mixture was filtered through a pad of Celite and the filtrate was concentrated under reduce pressure to provide compound Int 3-2 (500 mg, 72%), which was used for next step without further purification. MS-ESI (m/z): 116.3 (M+H)$^+$.

Step C—Preparation of Int 3-3

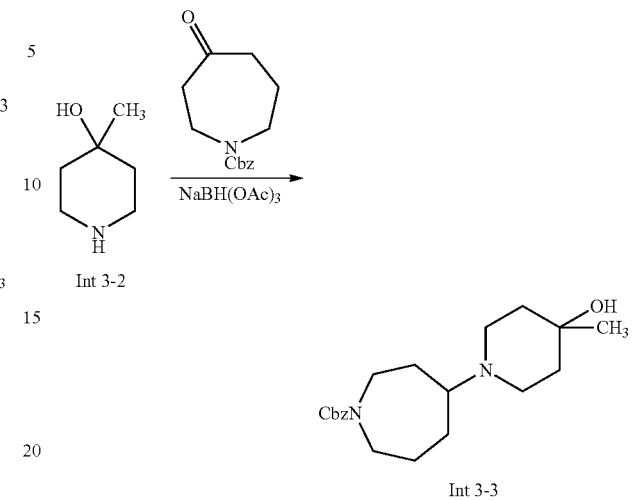

To a solution of compound Int 3-2 (150 mg, 1.30 mmol) in 1,2-dichloroethane (3 mL) was added N-Cbz-4-azepinone (321 mg, 1.30 mmol) and tetraethyl titanate (1.48 g, 6.50 mmol), and the mixture was allowed to stir at 90° C. for 3 hours. The resulted mixture was cooled to room temperature before NaBH(OAc)$_3$ (827 mg, 3.90 mmol) was added. The mixture was allowed to stir at room temperature for 2 hours. The reaction was quenched with water (20 mL) and diluted with dichloromethane (10 mL) and filtered. The filtrate was concentrated in vacuo and the residue was purified using preparative-TLC to provide compound Int 3-3 (80 mg). $^1$H NMR (CD$_3$OD) δ: 7.39-7.32 (m, 5H), 5.15-5.13 (m, 2H), 3.70-3.40 (m, 5H), 3.22-3.17 (m, 4H), 2.16-1.98 (m, 4H), 1.87-1.65 (m, 7H), 1.65-1.27 (m, 2H). MS-ESI (m/z): 347.1 (M+H)$^+$.

Step D—Preparation of Int 3-4

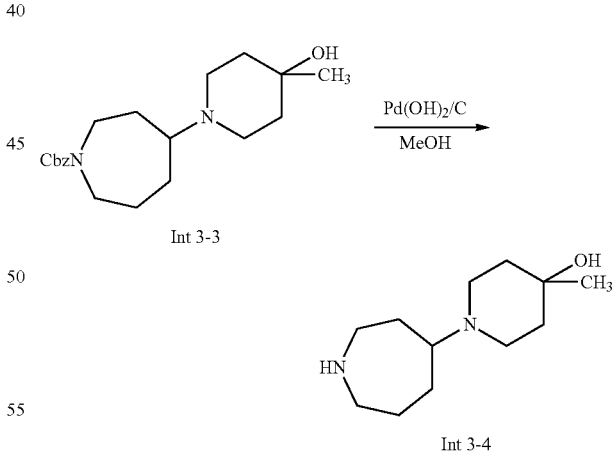

A mixture of compound Int 3-3 (80 mg, 0.23 mmol) and Pd(OH)$_2$/C (10 mg) in methanol (30 mL) was degassed under reduce pressure and purged with hydrogen 3 times. The reaction mixture was stirred under hydrogen (50 psi) at room temperature overnight. The reaction mixture was filtered through a pad of Celite and the filtrate was concentrated under reduce pressure to provide crude compound Int 3-4 which was used in next step without further purification. (40 mg, 82%). MS-ESI (m/z): 213.2 (M+H)$^+$.

Step E—Preparation of Compound 3

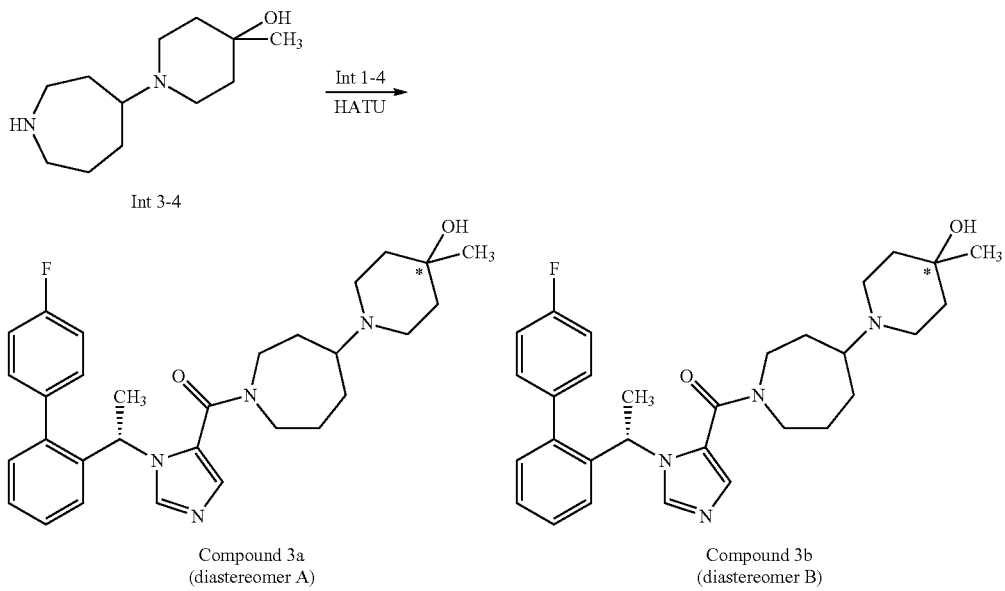

Compound 3a
(diastereomer A)

Compound 3b
(diastereomer B)

A mixture of compound Int 1-4 (60 mg, 0.194 mmol), HATU (111 mg, 0.291 mmol) and diisopropylethylamine (75 mg, 0.584 mmol) in dichloromethane (3 mL) was allowed to stir at room temperature for 15 mins before compound Int 3-4 (45.2 mg, 0.213 mmol) was added. The mixture was allowed to stir at room temperature for 2 hrs and the reaction mixture was filtered. The filtrate was concentrated in vacuo and the residue was purified using preparative-HPLC. The resulting mixture of diastereomers were then separated by SFC to provide the single diastereomers Compound 3a (25 mg) and Compound 3b (25 mg). Compound 3a: $^1$H NMR (CD$_3$OD) δ: 8.04 (d, J=16.0 Hz, 1H), 7.51 (s, 1H), 7.41-7.16 (m, 6H), 6.77 (d, J=4.8 Hz, 1H), 6.52 (s, 1H), 6.21 (d, J=6.8 Hz, 1H), 6.05 (d, J=5.2 Hz, 1H), 3.85 (d, J=13.6 Hz, 1H), 3.63-3.55 (m, 2H), 3.44 (d, J=6.4 Hz, 1H), 3.22-3.11 (m, 2H), 2.76-2.62 (m, 3H), 2.42 (s, 1H), 1.97-1.85 (m, 3H), 1.67-1.56 (m, 8H), 1.21-1.16 (m, 3H), 0.58 (t, J=11.2 Hz, 1H). MS-ESI (m/z): 505.3 (M+H)$^+$. Compound 3b: $^1$H NMR (CD$_3$OD) δ: 7.95 (s, 1H), 7.35-7.18 (m, 8H), 6.86 (s, 1H), 6.00 (s, 1H), 3.59 (s, 3H), 3.24 (s, 1H), 2.54 (s, 2H), 2.43-2.36 (m, 3H), 2.18 (s, 1H), 1.99-1.88 (m, 2H), 1.69 (s, 4H), 1.56 (s, 4H), 1.17-1.12 (m, 5H). MS-ESI (m/z): 505.3 (M+H)$^+$.

Example 4

Preparation of Compound 4

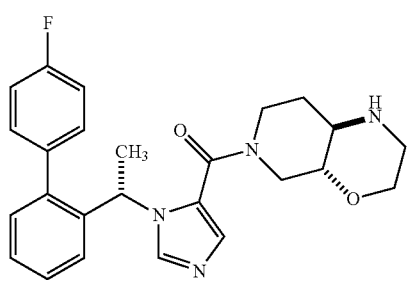

4

Step A—Preparation of Int 4-1

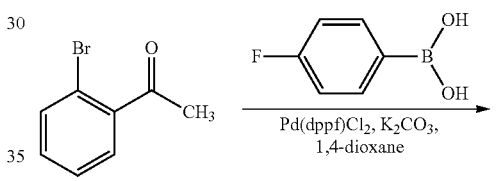

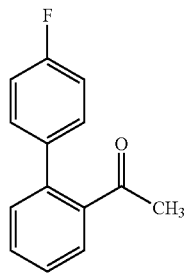

Int 4-1

A degassed mixture of 2-bromoacetophenone (11.0 g, 54.9 mmol), 4-fluoro-phenylboronic (9.2 g, 65.9 mmol), Pd(dppf)Cl$_2$ (4.0 g, 5.49 mmol) and sodium carbonate (11.6 g, 110 mmol) in 1,4-dioxane (100 mL) and water (20 mL) was heated to 90° C. and then stirred at that temperature overnight. The resulting mixture was then cooled to room temperature and filtered. The filtrate was concentrated and the residue was purified using silica gel chromatography (petroleum ether: ethyl acetate=100:1 to 50:1) to provide Int 4-1 (8.8 g, 75%). $^1$H NMR (CDCl$_3$): δ 7.47-7.54 (m, 2H), 7.38-7.42 (m, 1H), 7.24-7.34 (m, 3H), 7.08-7.12 (m, 2H), 2.03 (s, 3H). MS (APCI): M/Z (M+1) 215.1.

Step B—Preparation of Int 4-2

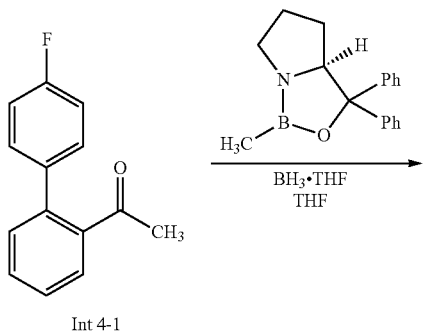

Int 4-1

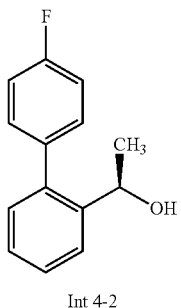

Int 4-2

To a dried round bottom flask was charged with commercial available (S)-2-methyl-CBS-oxazaborolidine (1.0 mL, 1M in THF, 1.0 mmol) and 5.0 mL of dry THF under N₂ atmosphere. After cooling to −30° C., 1M BH₃.THF (12.0 mL, 12.0 mmol) in THF was added and the mixture stirred at the same temperature for 30 minutes. A solution of Int 4-1 (2.1 g, 1.0 mmol) in dry THF (20.0 mL) was added into the mixture over an hour at −30° C. The reaction was followed by TLC (PE:EA=15:1) until completion. The resulting mixture was allowed to warm up to 0° C. and quenched by the addition of 5 mL of methanol. The mixture was then concentrated and the residue was purified via silica gel chromatography (PE: EA=20:1) to provide the desired alcohol Int 4-2 (1.8 g, 86%, e.e.: 85%).

Step C—Preparation of Int 4-3

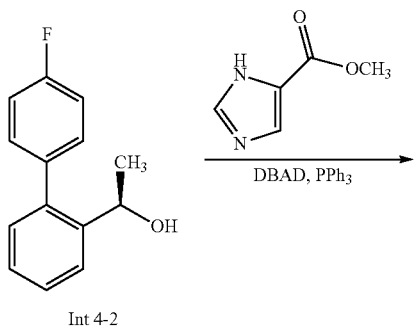

Int 4-2

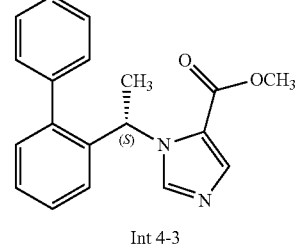

Int 4-3

To a −10° C. stirred mixture of alcohol Int 4-2 (6.5 g, 30.09 mmol), methyl 1H-imidazole-5-carboxylate (3.8 g, 30.09 mmol) and PPh₃ (9.46 g, 36.11 mmol) in THF (60 mL) was added a solution of di-tert-butyl-azodicarboxylate (8.3 g, 36.11 mmol) in 20 mL of THF dropwise. The mixture was stirred for 2 hrs at −10° C., then raised to room temperature and stirred overnight. The reaction mixture was poured into water and the aqueous was separated and extracted with ethyl acetate (5×30 mL). The combined organic layers were dried over Na₂SO₄ then filtered. The filtrate was concentrated in vacuo to provide the crude product, which was purified using silica gel chromatography (petroleum ether: ethyl acetate=10:1 to 6:1) to provide ester Int 4-3 (6.0 g, 60%; 85% e.e.). The desired S entiomer was further purified using SFC chromatography to provide pure (S)-ester Int 4-3 (>98% e.e.). SFC conditions: Instrument: Thar 350; Column: AY 250 mm*50 mm, 20 um; Mobile phase: A: Supercritical CO₂, B:EtOH (0.05% NH₄OH) A:B=85:15 at 220 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm. ¹H NMR (CDCl₃): δ 7.60 (s, 1H), 7.43 (s, 1H), 7.34-7.39 (m, 2H), 7.17-7.24 (m, 2H), 6.95-7.06 (m, 4H), 6.67-6.32 (m, 1H), 3.70 (s, 3H), 1.39 (d, J=6.4 Hz, 3H). MS (APCI): M/Z (M+1) 325.1.

Step D—Preparation of Int 4-4

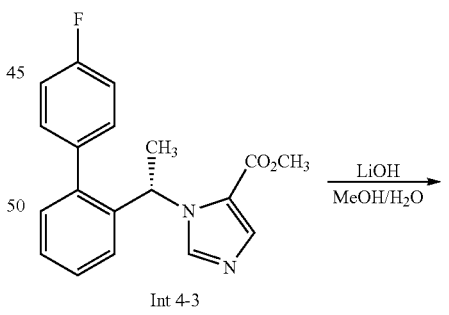

Int 4-3

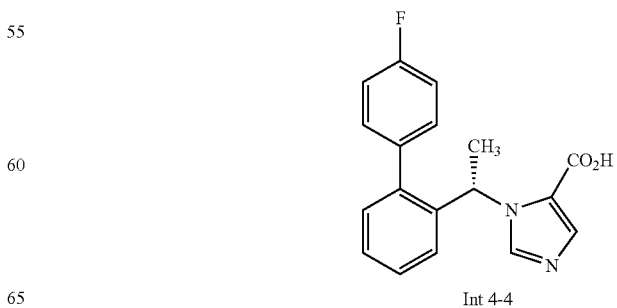

Int 4-4

To a stirred solution of (5)-ester Int 4-3 (3.25 g, 10.0 mmol) in 50 mL of MeOH and 20 mL of H₂O was added LiOH (1.2 g, 5.0 mmol) and the mixture was allowed to stir at room temperature for 5 hours. When the reaction was complete, aq. HCl (1.0 M) was added to adjust pH=5-6 and the mixture was concentrated in vacuo. The residue was extracted with ethyl acetate (3×100 mL) and the combined organic layers were washed with brine, dried over Na₂SO₄ and filtered. The filtrate was concentrated in vacuo to provide Int 4-4 (2.5 g, 81%). ¹H NMR (CD₃OD) δ: 7.76 (s, 1H), 7.57 (s, 1H), 7.41-7.26 (m, 2H), 7.19 (d, J=6.8 Hz, 1H), 7.13 (d, J=6.8 Hz, 1H), 7.07-7.05 (m, 4H), 6.48 (q, J=6.8 Hz, 1H), 1.70 (d, J=6.8 Hz, 3H). MS (APCI): M/Z (M+1) 311.2.

Step E—Preparation of Int 4-5

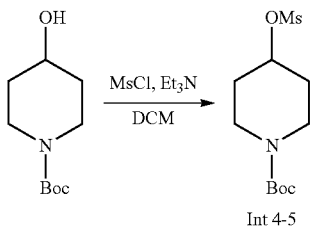 [SMILES: CC(C)(C)OC(=O)N1CCC(O)CC1 ; CC(C)(C)OC(=O)N1CCC(OS(C)(=O)=O)CC1]

A mixture of N-Boc-4-hydroxypiperidine (2200 g, 10.95 mol) in anhydrous DCM (8 L) was added triethylamine (2284 mL, 16.42 mol) in one portion at 0° C., then MsCl (1316 g, 11.49 mol) was added drop wise into the mixture at 0° C., then the mixture was allowed to stir at room temperature for 2 hours. TLC (petroleum ether: EtOAc=1:1, Rf=0.6) showed the reaction was complete. Water (2 L) was added into the mixture and the organic phase was separated, and then the organic phase was washed with 1 M hydrochloride solution (4 L), saturated NaHCO₃ solution (4 L), brine (1 L), and dried over anhydrous Na₂SO₄, then the mixture was concentrated in vacuo to provide compound Int 4-5 (3120 g, 100%) which was used for the next step without further purification.

Step F—Preparation of Int 4-6

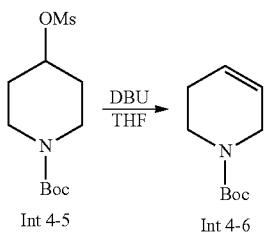

A solution of compound Int 4-5 (312 g, 1.12 mol) and DBU (400 g, 2.24 mol) in THF (4.5 L) was heated to reflux overnight. TLC (petroleum ether: EtOAc=3:1, Rf=0.8) showed the reaction was complete. The mixture was poured into ice-water (2 L) and then extracted with EtOAc (2 L), the combined organic phase was washed with 1 M HCl solution (4 L×2), aq. NaHCO₃ (4 L), and dried over anhydrous Na2SO4, then the mixture was concentrated in vacuo to provide compound Int 4-6 (185 g, 90%) which was used in the next step without further purification. ¹H NMR: (CDCl₃) δ 5.8 (m, 1H), 5.65 (m, 1H), 3.85 (t, J=7 Hz, 2H), 3.46 (t, J=14 Hz, 2H), 2.1 (bs, 2H), 1.45 (s, 9H).

Step G—Preparation of Int 4-7

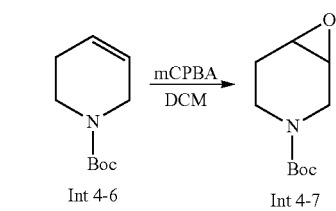

To a solution of Int 4-6 (617 g, 3.37 mol) in anhydrous DCM (10 L) was added m-CPBA (989 g, 5.73 mol) in portions at 0° C., then the mixture was allowed to stir at room temperature for 1 hours. TLC (petroleum ether:EtOAc=5:1) showed the reaction was complete. Saturated Na₂S₂O₃ (1 L) was added and separated, then the organic layer was washed with 5% aqueous K₂CO₃ (5 L×2), brine (4 L), dried over Na2SO4, concentrated in vacuo to get crude compound Int 4-7 which was purified using column chromatography (PE:EA=100:1-20:1) to obtain pure compound Int 4-7 (460 g, 72.6%). ¹H NMR: (CDCl₃) δ 3.85 (m, 1H), 3.65 (m, 1H), 3.39 (m, 1H), 3.26 (s, 1H), 3.18 (bs, 1H), 3.11 (m, 1H), 2.00 (m, 1H), 1.85 (m, 1H), 1.45 (s, 9H).

Step H—Preparation of Int 4-8a and Int 4-8b

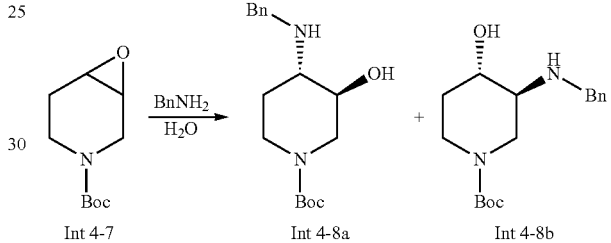

To a solution of compound Int 4-7 (500 g, 2.5 mol) in H₂O (5 L) was added BnNH₂ (294 g, 2.75 mol) at room temperature. Then the mixture was heated to reflux overnight. TLC (DCM: MeOH=10:1, Rf=0.3) showed the reaction complete. The mixture was extracted with DCM (1 L), dried over Na₂SO₄, concentrated in vacuo to provide compound Int 4-8a and Int 4-8b (765 g, 100%) which was used in the next step without further purification.

Step I—Preparation of Int 4-9

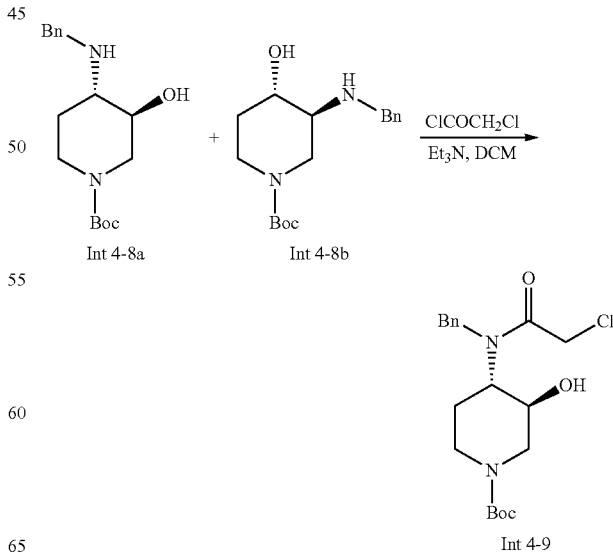

To a solution of trans-Int 4-8a and trans-Int 4-8b (153 g, 0.42 mol, crude) and triethylamine (126 g, 1.25 mol) in DCM (800 mL) was added drop wise chloroacetic chloride (33 g, 0.45 mol) at room temperature. The mixture was allowed to stir at room temperature overnight. TLC (DCM: MeOH=10:1, Rf=0.1) showed the reaction was complete. The mixture was quenched with water (300 mL) at 0° C., extracted with DCM (500 mL×3), the organic layer was washed with brine (1 L), dried over Na$_2$SO$_4$, concentrated in vacuo to get a crude product, which was purified using silica gel chromatography to provide Int 4-9 (40 g, 24.7%) as a mixture of trans diastereomers which was used directly in the next step.

Step J—Preparation of Int 4-10

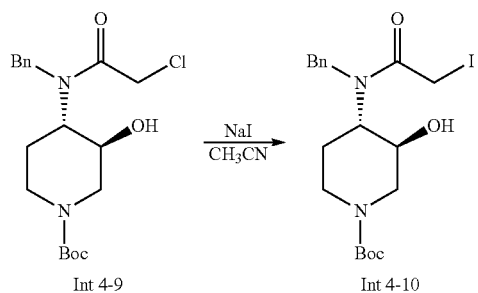

To a solution of trans-Int 4-9 (144 g, 376 mmol) in CH$_3$CN (2 L) was added NaI (56.4 g, 376 mmol) in one portion. The mixture was allowed to stir at reflux for 1 h then concentrated to provide a residue, which was dissolved in DCM (1 L), then filtered. The filtrate was concentrated in vacuo to provide compound Int 4-10 (172 g, 100%) which was used directly in the next step without further purification.

Step K—Preparation of Int 4-11

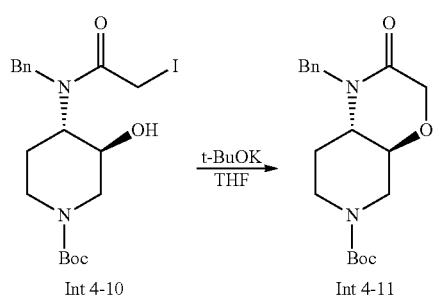 [SMILES: "t-BuOK" ; CC(C)(C)OC(=O)N1CC[C@H](N(Cc2ccccc2)C(=O)CI)[C@@H](O)C1 ; CC(C)(C)OC(=O)N1CC[C@H]2[C@H](C1)OCC(=O)N2Cc1ccccc1 ; "THF"]

To a solution of trans-Int 4-10 (172 g, 363 mmol) in THF (1500 mL) was added t-BuOK (48.72 g, 435 mmol) in portions at 0° C. After the addition, the mixture was allowed to stir at room temperature for 2 h when TLC (petroleum ether: EtOAc=1:1, Rf=0.3) showed the reaction was complete. The mixture was poured into ice-water (400 mL), extracted with EtOAc (200 mL×2), the organic layer was washed with brine (200 mL), dried over Na$_2$SO$_4$, concentrated in vacuo to provide compound Int 4-11 (126 g, 100%) which was used in the next step without further purification.

Step L—Preparation of Int 4-12

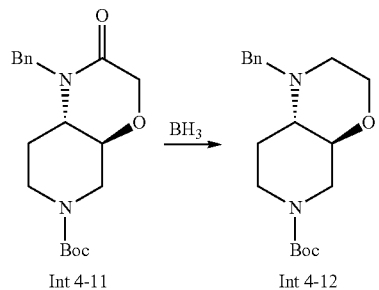

To a solution of trans-Int 4-11 (126 g, 346 mmol) in anhydrous THF (2 L) was added borane methylsulfide complex (109 mL, 1.038 mol) drop wise at 0° C. After addition, the mixture was allowed to stir at room temperature overnight. TLC (petroleum ether: EtOAc=1:1, Rf=0.1) indicated that the starting material was consumed completely. The mixture was added MeOH (300 mL) at room temperature and heated to reflux for 1 hour. TLC (petroleum ether: EtOAc=3:1, Rf=0.6) showed the reaction was complete. The mixture was washed with saturated NaHCO$_3$, brine and dried over Na$_2$SO$_4$, to get crude product, which was purified using silica gel chromatography to get pure compound Int 4-12 (86 g, 71%). $^1$H NMR: (CDCl$_3$) δ 7.21 (m, 5H), 4.11 (m 3H), 3.70 (dd, J=3.0, 7.2 Hz, 2H), 3.66 (dt, J=3.0, 6.0 Hz, 2H), 3.17 (m, 1H), 2.96 (d, J=13 Hz, 1H), 2.65 (m, 1H), 2.55 (d, J=), 2.15 (dt, J=3.6, 13.2 Hz, 1H), 2.11 (m, 2H), 1.38 (s, 9H)

Step M—Preparation of Int 4-13

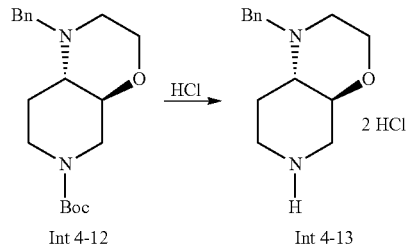 [SMILES: CC(C)(C)OC(=O)N1CC[C@H]2[C@H](C1)OCCN2Cc1ccccc1 ; Cl ; c1ccc(CN2CCO[C@H]3CNCC[C@@H]32)cc1]

To a mixture of trans-Int 4-12 (82 g, 246 mmol) in EtOAc (500 mL), was added drop wise a mixture of HCl (g) in EtOAc (1500 mL, 4 M) under ice-water bath. The reaction mixture was allowed to be stirred at room temperature for 2 hours. TLC (petroleum ether: EtOAc=1:3, Rf=0.1) indicated that the starting material was consumed completely. The mixture was concentrated in vacuo to provide compound Int 4-13 (80 g, 100%) as a white solid. $^1$H NMR: (DMSO-d$^6$) δ 7.44-7.54 (m, 5H), 4.7 (d, J=12.8 Hz, 1H), 3.45 (t, J=12 Hz, 1H), 3.30-3.50 (m, 3H), 2.80-3.20 (m, 4H), 2.65 (bd, 1H), 2.0 (m, 1H).

Step N—Preparation of Int 4-14

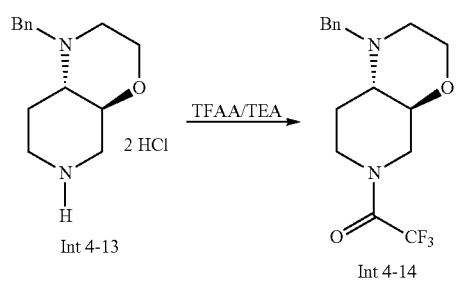 [SMILES: c1ccc(CN2CCO[C@H]3CNCC[C@@H]32)cc1 ; "TFAA/TEA" ; O=C(N1CC[C@H]2[C@H](C1)OCCN2Cc1ccccc1)C(F)(F)F]

To the solution of trans-Int 4-13 (79 g, 0.34 mol) and TEA (72.1 g, 0.714 mol) in DCM (1 L) was added drop wise TFAA (78.5 g, 0.37 mol) at 0° C. The mixture was allowed to stir at room temperature overnight when TLC (petroleum ether: EtOAc=1:1, Rf=0.6) showed the reaction was complete. The mixture was poured into water and extracted with DCM (500 mL×3). The combined organic layers were combined and concentrated to provide Int 4-14 (87 g, 74.3%) as an oil, which was used in next step without any furthermore purification.

Step O—Preparation of Int 4-15

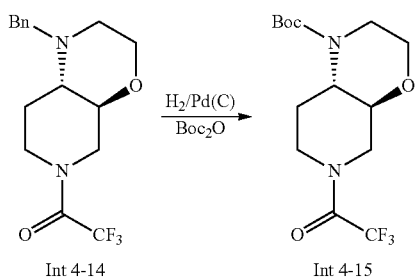

To a mixture of trans-Int 4-14 (51.6 g, 0.15 mol), Pd/C (20 g) and (Boc)$_2$O (38.4 g, 0.176 mol) in MeOH (100 mL) was allowed to stir at room temperature under H$_2$ (20 psi) for 6 hours. The mixture was filtered and the filtrate was concentrated in vacuo to provide compound Int 4-15 (44 g, 88.0%). $^1$H NMR: (CDCl$_3$) δ4.5-4.7 (m, 1H), 4.05 (m, 1H), 3.8-4.0 (m, 2H), 3.7 (m, 1H), 3.35 (m, 1H), 3.3-3.5 (m, 2H), 3.08 (m, 1H), 2.96 (m, 1H), 2.6-2.8 (m, 2H), 1.7-1.9 (m, 1H), 1.46 (s, 9H).

Step P—Preparation of Int 4-16

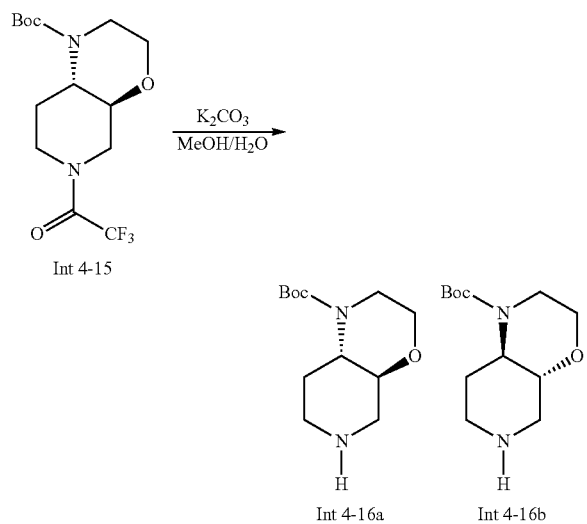

To a solution of trans-Int 4-15 (70 g, 0.20 mol) in MeOH (160 mL) and water (600 mL) was added K$_2$CO$_3$ (34.2 g, 0.24 mol) in one portion at room temperature. After stirring for 2 h the mixture extracted with DCM (200 mL×5) and the combined organic washings were concentrated to provide the desired compound Int 4-16 (40 g, 83.0%) as a mixture of trans diastereomers. SFC purification afforded the pure S,S diastereomer Int 4-16a (peak 1: 41.3%) $^1$H NMR: (CDCl$_3$) δ 3.88-3.80 (m, 2H), 3.77-3.67 (m, 1H), 3.35-3.34 (m, 2H), 3.29-3.27 (m, 2H), 3.10-3.11 (d, 1H), 2.54-2.42 (m, 3H), 1.76 (s, 1H), 1.70-1.60 (m, 1H), 1.45 (s, 9H) LCMS (M+H)=242.9 and R,R diastereomer Int 4-16b (peak 2: 41.9%)$^1$H NMR: (CDCl$_3$) δ 3.89-3.80 (m, 2H), 3.77-3.67 (m, 1H), 3.35-3.34 (m, 2H), 3.29-3.27 (m, 2H), 3.10-3.11 (d, 1H), 2.54-2.42 (m, 3H), 1.76 (s, 1H), 1.70-1.60 (m, 1H), 1.44 (s, 9H) LCMS (M+H)=242.9 each as white solids.

Step Q—Preparation of Int 4-17

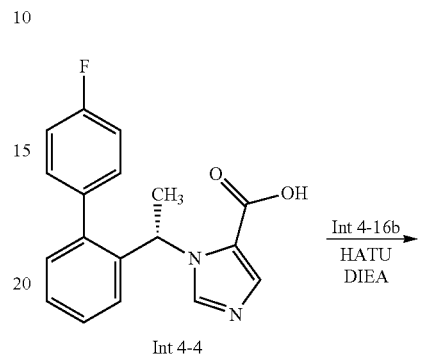

To a stirred solution of Int 4-4 (3.84 g, 12.4 mmol), Int 4-16b (3.0 g, 12.4 mmol), N,N-diisopropylethylamine (2.4 g, 18.5 mmol) in 25 mL of DMF was added HATU (7.06 g, 18.5 mmol) at 25° C. The reaction was stirred for 2.5 hour then poured into water. The aqueous phase was extracted with dichlomethane (3×15 mL) and the combined organic layers were dried over sodium sulfate then filtered. The filtrate was concentrated in vacuo to provide a residue which was purified using silica gel chromatography (petroleum ether: ethyl acetate=1:1) to provide compound Int 4-17 (5.5 g, 83.3%). MS-ESI (m/z): 535.5 (M+H)$^+$.

Step R—Preparation of Compound 4

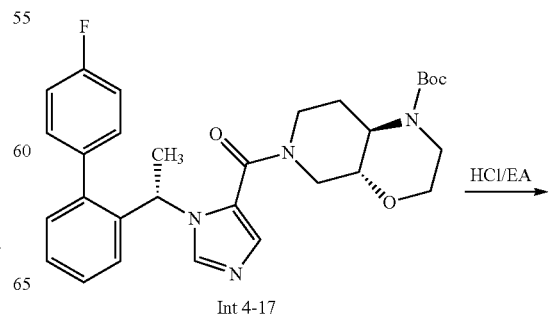

-continued

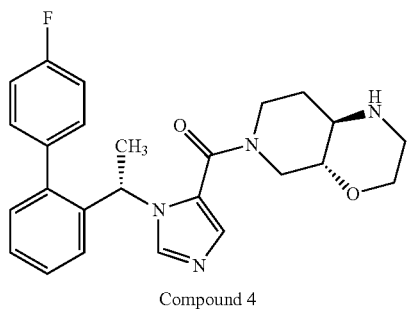

Compound 4

To a stirred solution of compound Int 4-17 (5.5 g, 10.3 mmol) in ethyl acetate (5 mL) was added HCl/EtOAc (10 mL). The solution was allowed to stir at room temperature for 20 min then concentrated to provide the crude product which was recrystallized in petroleum ether: ether acetate=1:1 to provide Compound 4 (3.1 g, 69.3%) as white solid. $^1$H NMR (CD$_3$OD) δ: 7.63 (s, 1H), 7.37-7.22 (m, 4H), 7.21-7.03 (m, 4H), 6.80 (br, 1H), 5.95 (q, J=6.3 Hz, 1H), 4.25 (br, 2H), 4.15-3.98 (m, 2H), 3.73 (br, 1H), 3.14 (br, 2H), 2.85-2.65 (m, 2H), 2.05-1.85 (m, 2H), 1.66 (d, J=6.3 Hz, 3H), 1.45 (br, 1H). MS-ESI (m/z): 435.5 (M+H)$^+$.

Example 5

Preparation of Compound 5

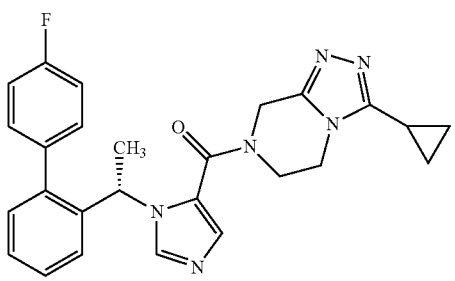

Step A—Preparation of Compound 5

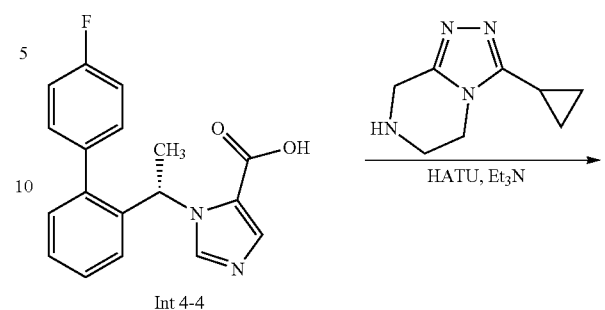

Int 4-4

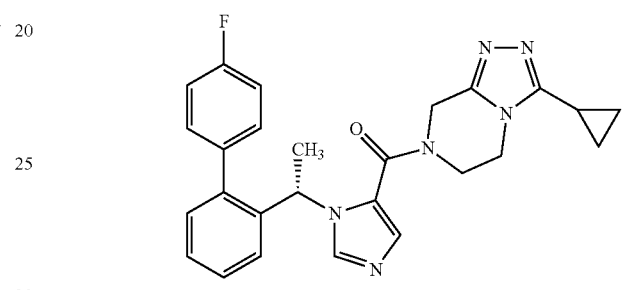

Compound 5

To a stirred solution of compound Int 1-4 (60 mg, 0.19 mmol) and triethylamine (39 mg, 0.38 mmol) in 2 mL of DMF was added 110 mg (0.29 mmol) of HATU. After stirring for 30 min, 44 mg (0.23 mmol) of 3-cyclopropyl-5,6,7,8-tetrahydro-1,2,4-triazolo[4,3-a]pyrazine [CAS No 945262-32-8] was added and the mixture was allowed to stir at room temperature for one hour. The reaction mixture was filtered and the filtrate was purified using preparative-HPLC to provide the desired compound 5 (30 mg, 23%). $^1$H NMR (CD$_3$OD) δ: 8.02 (s, 1H), 7.55-7.22 (m, 3H), 7.20-6.54 (m, 6H), 5.88 (d, J=6.3 Hz, 1H), 4.32 (s, 3H), 3.85-3.43 (m, 3H), 2.00-1.60 (m, 4H), 1.28-0.80 (m, 4H). MS-ESI (m/z): 457.5 (M+1)$^+$.

The following compounds 6 and 7, of the present invention, were prepared starting from Int 1-4 and an appropriately substituted amine intermediate using a reductive amination protocol similar to that described in Example 5 above.

| Cmd | Structure | IUPAC name | M + 1 | $^1$H NMR |
|---|---|---|---|---|
| 6 | ![structure] | (1-((S)-1-(4'-fluoro-[1,1'-biphenyl]-2-yl)ethyl)-1H-imidazol-5-yl)((7R,8aS)-7-hydroxyhexahydro-pyrrolo[1,2-a]pyrazin-2(1H)-yl)methanone | 435.2 | (CD$_3$OD) δ: 8.08-7.91 (m, 1 H), 7.64-7.27 (m, 4 H), 7.22-7.12 (m, 4 H), 6.90-6.73 (m, 1 H), 5.90 (q, J = 6.6 Hz, 1 H), 4.81-3.50 (m, 3 H), 3.47-3.33 (m, 1 H), 3.21-2.47 (m, 3 H), 2.27-1.97 (m, 2H), 1.89-1.48 (m, 5 H), 1.39-1.23 (m, 1 H). |

| Cmd | Structure | IUPAC name | M + 1 | ¹H NMR |
|---|---|---|---|---|
| 7 | 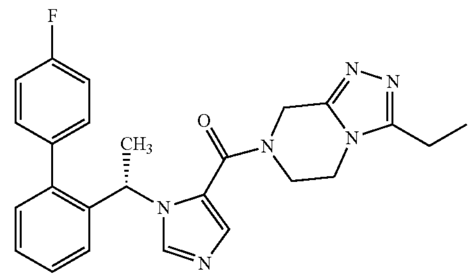 [SMILES: CCc1nnc2n1CCN(C(=O)c1cncn1[C@@H](C)c1ccccc1-c1ccc(F)cc1)C2] | (S)-(3-ethyl-5,6-dihydro-[1,2,4]triazolo[4,3-a]pyrazin-7(8H)-yl)(1-(1-(4'-fluoro-[1,1'-biphenyl]-2-yl)ethyl)-1H-imidazol-5-yl)methanone | 445.2 | (CD₃OD) δ: 8.01 (s, 1H), 7.64-7.23 (m, 3H), 7.21-6.66 (m, 6H), 5.88 (q, J = 6.7 Hz, 1H), 4.84-4.57 (m, 2H), 4.30 (br, 1H), 3.82-3.52 (m, 3H), 2.71 (q, J = 7.0 Hz, 2H), 1.75 (d, J = 6.7 Hz, 3H), 1.36 (t, J = 7.4 Hz, 3H). |

Example 6

Preparation of Compound 8

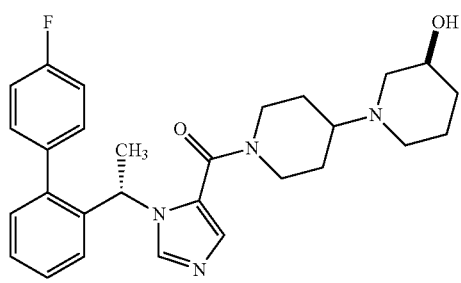

Step A—Preparation of Int 6-1

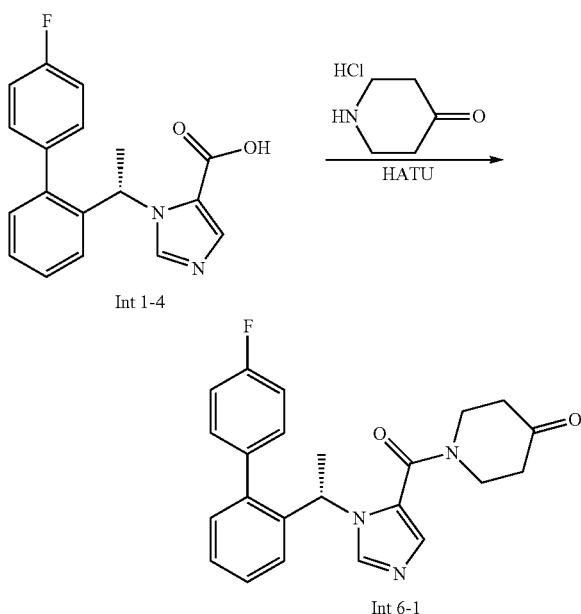

A mixture of compound Int 1-4 (1.0 g, 3.2 mmol), N,N-diisopropylethylamine (1.24 g, 9.60 mmol) and HATU (1.8 g, 4.8 mmol) in dichloromethane (15 mL) was allowed to stir at room temperature for 30 min before adding 515.3 mg (3.8 mmol) of 4-piperidone HCl salt. The reaction mixture was stirred for 3 h then poured into water and extracted with DCM (3×50 mL). The combined organic layer was dried over anhydrous sodium sulfate then filtered. The filtrate was concentrated in vacuo and purified using column chromatography (DCM: methanol=100:1~50:1) to provide the product compound Int 6-1 as yellow oil. MS-ESI (m/z): 392.3 (M+H)⁺.

Step B—Preparation of Compound 8

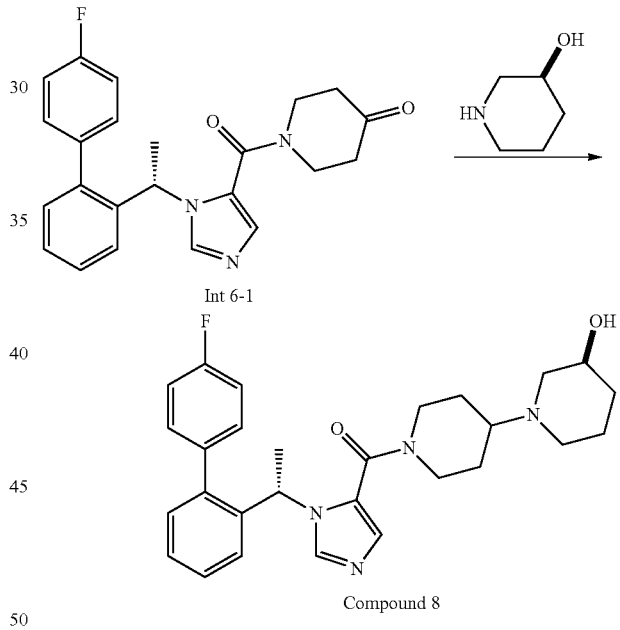

To a solution of compound Int 6-1 (100 mg, 0.26 mmol) in 1,2-dichloroethane (3 mL) was added 3-hydroxypiperidine (0.26 mmol) and tetraethyltitanate (218 mg, 0.77 mmol) and the mixture was allowed to stir at 90° C. for 3 hours. The resulted mixture was cooled to room temperature then treated with NaBH(OAc)₃ (163 mg, 0.77 mmol). The mixture was allowed to stir at room temperature for 3 h then quenched with water (20 mL) diluted with dichloromethane (10 mL), then filtered. The filtrate was concentrated in vacuo to provide the crude product which was purified using preparative-HPLC to provide 160 mg of compound 8 as white solid. ¹H NMR (CD₃OD) δ: 7.54-7.25 (m, 5H), 7.20-7.16 (m, 5H), 5.90 (br, 1H), 4.60 (br, 4H), 3.59 (br, 1H), 2.76-2.41 (m, 3H), 2.23-1.82 (m, 4H), 1.81-1.58 (m, 5H), 1.46 (d, J=10.6 Hz, 3H), 1.18 (d, J=8.2 Hz, 1H). MS-ESI (m/z): 477.3 (M+H)⁺.

The following compounds 9-33 were prepared starting from Int 6-1 and an appropriately substituted amine intermediate using a reductive amination protocol similar to that described in Example 6 above.

| Cmd | Structure | M + 1 | ¹H NMR |
|---|---|---|---|
| 9 | 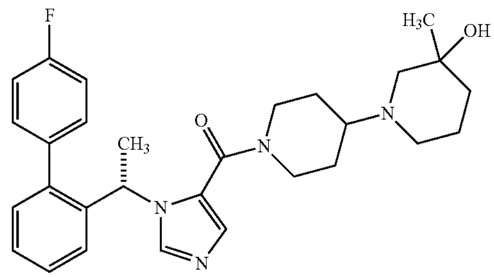 [SMILES: C[C@@H](c1ccccc1-c1ccc(F)cc1)n1cncc1C(=O)N1CCC(N2CCCC(C)(O)C2)CC1] | 491.3 | (CD$_3$OD) δ: 8.03 (br, 2H), 7.33-7.32 (m, 4H), 7.17 (s, 3H), 6.62 (br, 1H), 5.91 (br, 1H), 3.95-3.65 (m, 3H), 3.29-3.07 (m, 2H), 2.74-2.68 (m, 3H), 2.47-2.07 (m, 2H), 1.89-1.87 (m, 2H), 1.68 (br, 2H), 1.53 (br, 3H), 1.50-1.47 (m, 3H), 1.33 (s, 1H), 1.16-1.14 (m, 2H). |
| 10 | 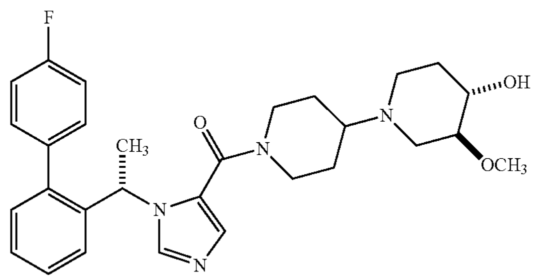 [SMILES: CO[C@H]1CN(C2CCN(C(=O)c3cncn3[C@@H](C)c3ccccc3-c3ccc(F)cc3)CC2)CC[C@@H]1O] | 507.2 | (CD$_3$OD) δ: 8.01 (s, 1H), 7.52-6.95 (m, 7H), 6.63 (br, 1H), 5.91 (br, 1H), 4.87-3.76 (m, 4H), 3.43 (s, 3H), 3.17-2.35 (m, 6H), 2.32-1.56 (m, 7H), 1.53-0.59 (m, 4H). |
| 11 | 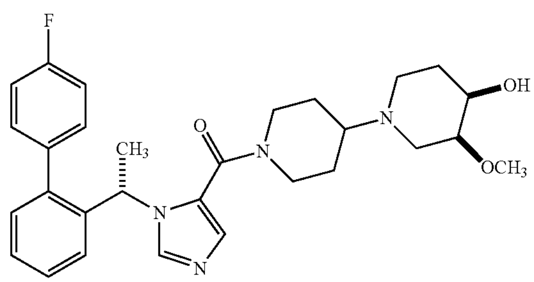 [SMILES: CO[C@H]1CN(C2CCN(C(=O)c3cncn3[C@@H](C)c3ccccc3-c3ccc(F)cc3)CC2)CC[C@H]1O] | 507.2 | (CD$_3$OD) δ: 8.01 (s, 1H), 7.56-7.07 (m, 7H), 6.64 (br, 1H), 5.91 (br, 1H), 4.66-3.78 (m, 4H), 3.43 (s, 3H), 3.23-2.04 (m, 8H), 1.98-1.01 (m, 9H). |
| 12 | 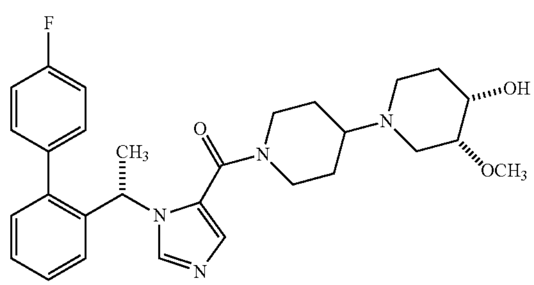 [SMILES: CO[C@@H]1CN(C2CCN(C(=O)c3cncn3[C@@H](C)c3ccccc3-c3ccc(F)cc3)CC2)CC[C@@H]1O] | 507.2 | (CD$_3$OD) δ: 8.01 (s, 1H), 7.53-7.05 (m, 7H), 6.63 (br, 1H), 5.91 (br, 1H), 4.64-3.76 (m, 4H), 3.43 (s, 3H), 3.25-2.89 (m, 3H), 2.78-2.14 (m, 6H), 1.95-1.01 (m, 8H). |
| 13 | 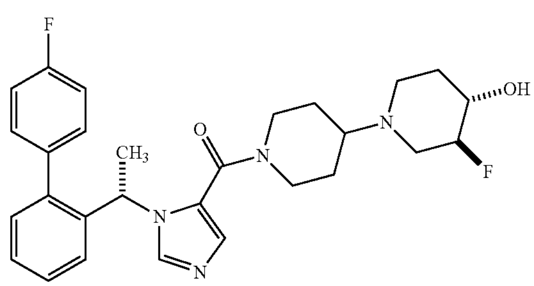 [SMILES: C[C@@H](c1ccccc1-c1ccc(F)cc1)n1cncc1C(=O)N1CCC(N2CC[C@H](O)[C@@H](F)C2)CC1] | 495.2 | (CD$_3$OD) δ: 8.02 (s, 1H), 7.59-7.24 (m, 4H), 7.24-7.10 (m, 3H), 6.71 (br, 2H), 5.93 (br, 1H), 4.37-3.57 (m, 4H), 3.08-2.29 (m, 7H), 2.11-1.47 (m, 7H), 1.29 (br, 2H). |

-continued

| Cmd | Structure | M + 1 | ¹H NMR |
|---|---|---|---|
| 14 | 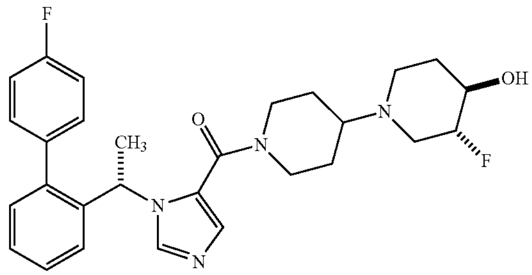 [SMILES: C[C@@H](c1ccccc1-c1ccc(F)cc1)n1cncc1C(=O)N1CCC(N2CC[C@@H](O)[C@H](F)C2)CC1] | 495.2 | (CD₃OD) δ: 8.01 (s, 1H), 7.59-7.26 (m, 4H), 7.24-6.93 (m, 4H), 6.65 (br, 1H), 5.91 (br, 1H), 4.49 (br, 1H), 4.35-4.01 (m, 2H), 3.93 (br, 1H), 3.49 (br, 1H), 3.08-2.76 (m, 2H), 2.64-2.50 (m, 2H), 2.20 (br, 2H), 1.88 (br, 1H), 1.70 (br, 4H), 1.55-1.33 (m, 2H), 1.33-1.18 (m, 1H), 1.00 (br, 1H). |
| 15 | 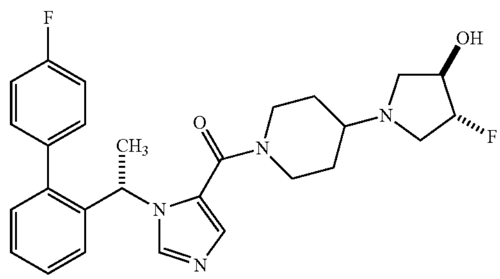 [SMILES: C[C@@H](c1ccccc1-c1ccc(F)cc1)n1cncc1C(=O)N1CCC(N2C[C@@H](O)[C@H](F)C2)CC1] | 481.2 | (CD₃OD) δ: 7.94 (s, 1H), 7.33-7.31 (m, 4H), 7.17-7.14 (m, 4H), 6.83 (s, 1H), 5.90 (d, J = 5.6 Hz, 1H), 4.30-4.21 (m, 1H), 3.81 (br, 3H), 3.10 (s, 1H), 2.90-2.73 (m, 4H), 2.29 (s, 2H), 1.72 (d, J = 6 Hz, 5H), 1.32 (br, 2H). |
| 16 | 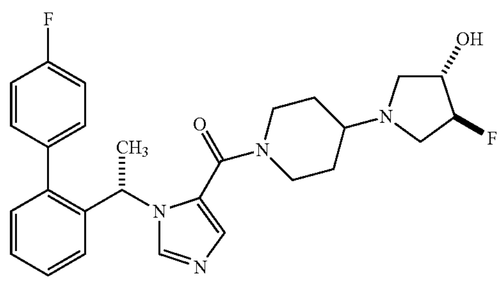 [SMILES: C[C@@H](c1ccccc1-c1ccc(F)cc1)n1cncc1C(=O)N1CCC(N2C[C@H](O)[C@@H](F)C2)CC1] | 481.2 | (CDCl₃) δ: 7.98 (s, 1H), 7.35-7.32 (m, 4H), 7.12-7.15 (m, 4H), 6.84 (br, 1H), 5.90 (q, J = 7.0 Hz, 1H), 4.29-4.21 (m, 1H), 3.81-3.52 (m, 3H), 3.15 (br, 1H), 2.93-2.71 (m, 4H), 2.35 (s, 2H), 1.74 (d, J = 5.6H z, 3H), 1.75-1.32 (m, 4H). |
| 17 | 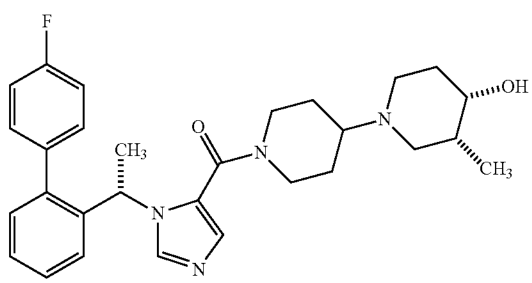 [SMILES: C[C@@H]1CN(C2CCN(C(=O)c3cncn3[C@@H](C)c3ccccc3-c3ccc(F)cc3)CC2)CC[C@@H]1O] | 491.2 | (CD₃OD) δ: 7.99 (s, 1H), 7.50-7.25 (m, 4H), 7.25-7.05 (m, 3H), 7.02-6.53 (m, 2H), 5.90 (br, 1H), 4.52 (br, 2H), 3.92 (br, 2H), 3.10-2.37 (m, 6H), 2.20 (br, 1H), 1.93-1.40 (m, 8H), 1.27 (br, 1H), 0.94 (br, 3H). |
| 18 | 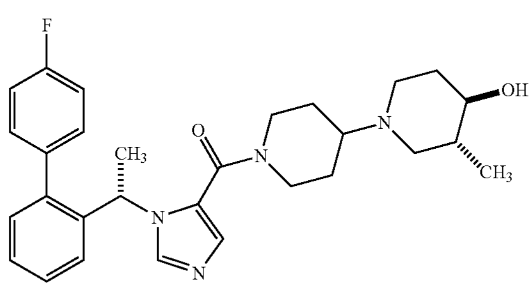 [SMILES: C[C@@H]1CN(C2CCN(C(=O)c3cncn3[C@@H](C)c3ccccc3-c3ccc(F)cc3)CC2)CC[C@H]1O] | 491.2 | (CD₃OD) δ: 7.99 (s, 1H), 7.49-7.26 (m, 4H), 7.23-6.89 (m, 4H), 6.69 (s, 1H), 5.91 (br, 1H), 4.51 (br, 2H), 3.97 (br, 2H), 3.10-2.53 (m, 6H), 2.29 (br, 1H), 2.03-1.41 (m, 9H), 0.97 (d, J = 6.3 Hz, 3H). |

-continued

| Cmd | Structure | M + 1 | ¹H NMR |
|---|---|---|---|
| 19 | 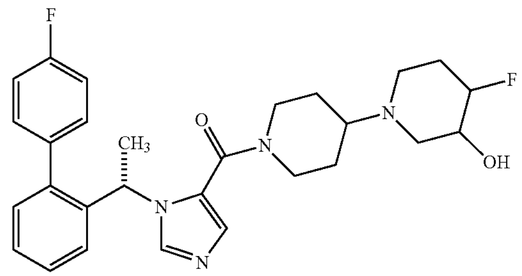 [SMILES: C[C@@H](c1ccccc1-c1ccc(F)cc1)n1cncc1C(=O)N1CCC(N2CCC(F)C(O)C2)CC1] | 495.2 | (CD₃OD) 7.54-7.12 (m, 7H), 6.67 (br, 2H), 5.92 (br, 1H), 4.70-3.82 (m, 4H), 3.65 (br, 1H), 3.12-2.54 (m, 5H), 2.07 (br, 3H), 1.93-1.57 (m, 5H), 1.31 (br, 2H). |
| 20 | 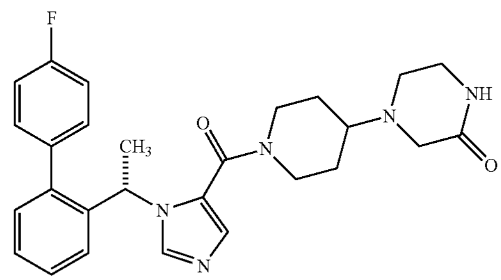 [SMILES: C[C@@H](c1ccccc1-c1ccc(F)cc1)n1cncc1C(=O)N1CCC(N2CCNC(=O)C2)CC1] | 476.2 | (CD₃OD) δ: 7.99 (s, 1H), 7.36-7.34 (m, 4H), 7.21-7.16 (m, 4H), 6.69 (br, 1H), 5.91 (q, J = 6.4 Hz, 1H), 4.54 (br, 1H), 3.94 (br, 1H), 3.25 (s, 2H), 3.08 (br, 3H), 2.68-2.50 (m, 4H), 1.72-1.51 (m, 6H), 1.10 (br, 1H). |
| 21 | 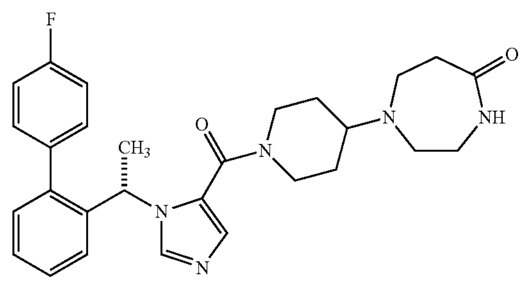 [SMILES: C[C@@H](c1ccccc1-c1ccc(F)cc1)n1cncc1C(=O)N1CCC(N2CCNC(=O)CC2)CC1] | 490.3 | (CD₃OD) δ: 8.02 (s, 1H), 7.38-7.31 (m, 4H), 7.25-18 (m, 4H), 6.65 (br, 1H), 5.94 (s, 1H), 4.57-4.52 (m, 1H), 4.03-3.92 (m, 1H), 3.25 (br, 2H), 3.06-2.97 (m, 1H), 2.76-2.52 (m, 9H), 1.72 (d, J = 12.8 Hz, 4H), 1.51-1.02 (m, 2H). |
| 22 | 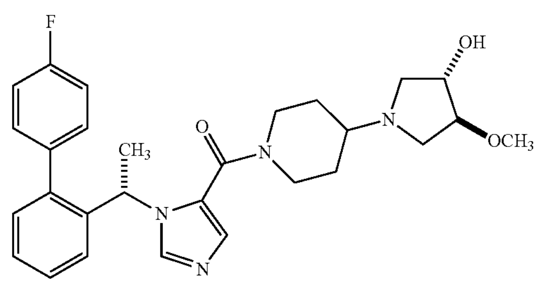 [SMILES: CO[C@H]1CN(C2CCN(C(=O)c3cncn3[C@@H](C)c3ccccc3-c3ccc(F)cc3)CC2)C[C@@H]1O] | 493.3 | (CD₃OD) δ: 7.96 (s, 1H), 7.46-6.61 (m, 8H), 5.88 (q, J = 5.9 Hz, 1H), 4.52-3.54 (m, 4H), 3.31-3.21 (m, 5H), 2.98-2.27 (m, 6H), 2.16-1.00 (m, 7H). |
| 23 | 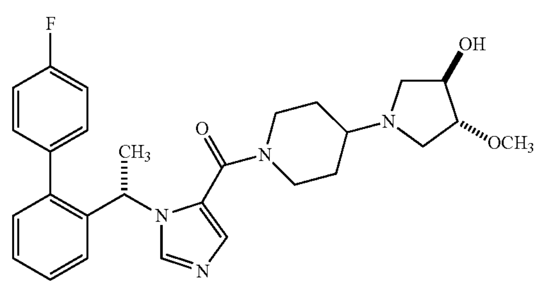 [SMILES: CO[C@@H]1CN(C2CCN(C(=O)c3cncn3[C@@H](C)c3ccccc3-c3ccc(F)cc3)CC2)C[C@H]1O] | 493.3 | (CD₃OD) δ: 7.96 (s, 1H), 7.62-6.33 (m, 8H), 5.87 (br, 1H), 4.62-3.52 (m, 4H), 3.29-3.20 (m, 5H), 3.13-2.24 (m, 6H), 2.10-0.74 (m, 7H). |

-continued

| Cmd | Structure | M + 1 | ¹H NMR |
|---|---|---|---|
| 24 | 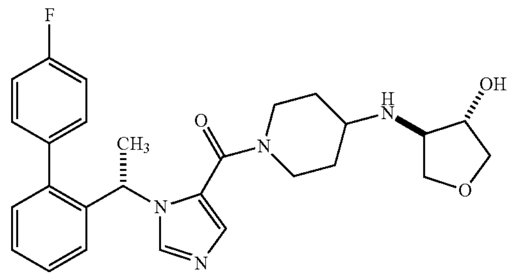 | 479.2 | (CD₃OD) δ: 7.95 (s, 1H), 7.38-7.26 (m, 4H), 7.22-7.09 (m, 4H), 6.90 (br, 1H), 5.88 (q, J = 6.3 Hz, 1H), 4.38-4.16 (m, 1H), 4.08-3.97 (m, 2H), 3.95-3.71 (m, 2H), 3.63-3.56 (m, 1H), 3.46 (m, 1H), 3.21 (s, 1H), 2.97-2.64 (m, 3H), 1.93-1.63 (m, 5H), 1.28-0.93 (m, 2H). |
| 25 | 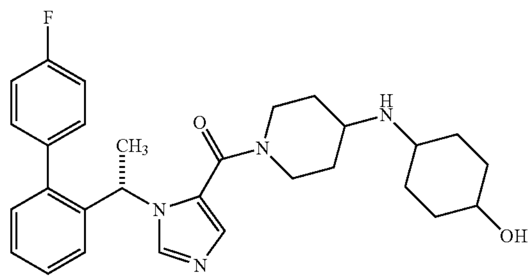 [SMILES: C[C@@H](c1ccccc1-c1ccc(F)cc1)n1cncc1C(=O)N1CCC(NC2CCC(O)CC2)CC1] | 491.3 | (CD₃OD) δ: 7.94 (s, 1H), 7.78-6.99 (m, 8H), 6.89 (br, 1H), 5.88 (q, J = 5.5 Hz, 1H), 4.59-3.38 (m, 5H), 2.99-2.44 (m, 4H), 2.10-1.59 (m, 8H), 1.38-0.91 (m, 5H) |
| 26 | 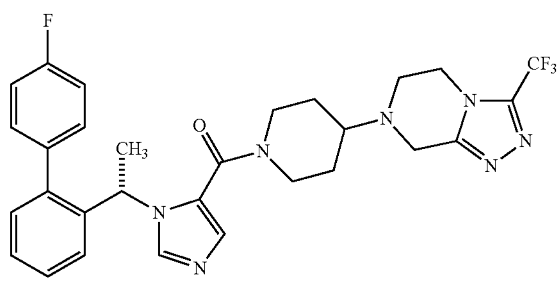 [SMILES: C[C@@H](c1ccccc1-c1ccc(F)cc1)n1cncc1C(=O)N1CCC(N2CCn3c(nnc3C(F)(F)F)C2)CC1] | 568.2 | (CD₃OD) δ: 8.01 (s, 1H), 7.66-6.92 (m, 8H), 6.69 (br, 1H), 5.93 (br, 1H), 4.54 (br, 1H), 4.14 (s, 2H), 3.84 (br, 3H), 2.93 (br, 2H), 2.89-2.54 (m, 3H), 2.08-1.76 (m, 2H), 1.70 (br, 3H), 1.47-0.95 (m, 2H) |
| 27 | 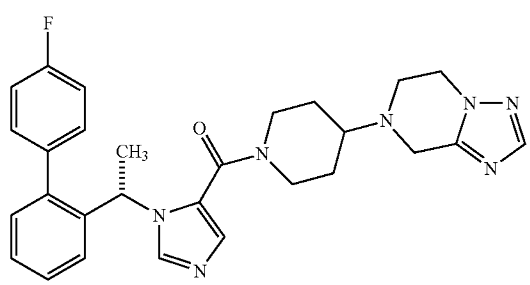 [SMILES: C[C@@H](c1ccccc1-c1ccc(F)cc1)n1cncc1C(=O)N1CCC(N2CCn3ncnc3C2)CC1] | 500.2 | (CD₃OD) δ: 8.15-7.90 (m, 2H), 7.60-7.07 (m, 8H), 6.86 (br, 1H), 5.98-5.86 (m, 1H), 4.44-3.44 (m, 6H), 3.27-2.37 (m, 5H), 1.87-1.08 (m, 7H) |
| 28 | 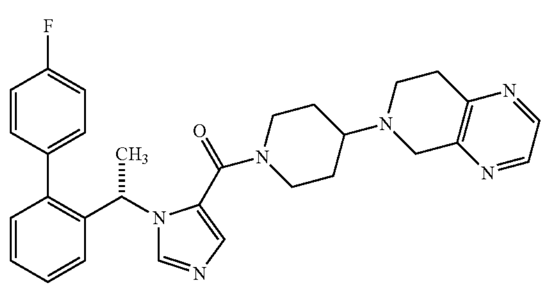 [SMILES: C[C@@H](c1ccccc1-c1ccc(F)cc1)n1cncc1C(=O)N1CCC(N2CCc3nccnc3C2)CC1] | 511.2 | (CD₃OD) δ: 8.37 (s, 2H), 8.02 (s, 1H), 7.50-7.25 (m, 4H), 7.25-7.08 (m, 4H), 6.68 (br, 1H), 5.93 (br, 1H), 4.59 (br, 1H), 3.96 (br, 1H), 3.73 (br, 2H), 3.17-2.93 (m, 3H), 2.91-2.63 (m, 4H), 1.86 (d, J = 11.6 Hz, 2H), 1.71 (br, 3H), 1.61-1.45 (m, 1H), 1.27 (br, 1H). |

-continued
| Cmd | Structure | M + 1 | ¹H NMR |
|---|---|---|---|
| 29 | 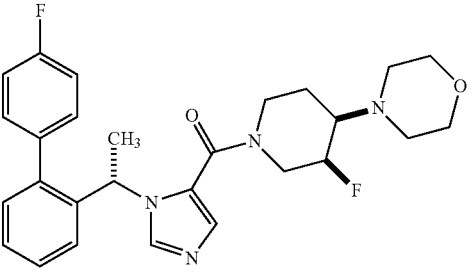 [SMILES: C[C@@H](c1ccccc1-c1ccc(F)cc1)n1cncc1C(=O)N1CC[C@@H](N2CCOCC2)[C@@H](F)C1] | 481.2 | (CDCl₃) δ: 8.00 (s, 1H), 7.32-7.20 (m, 4H), 7.18-7.03 (m, 4H), 6.59 (br, 1H), 5.88 (br, 1H), 5.05-4.95 (m, 1H), 4.53 (s, 1H), 4.13 (s, 1H), 3.66 (m, 4H), 3.10-2.43 (m, 7H), 1.71-1.28 (m, 5H). |
| 30 | 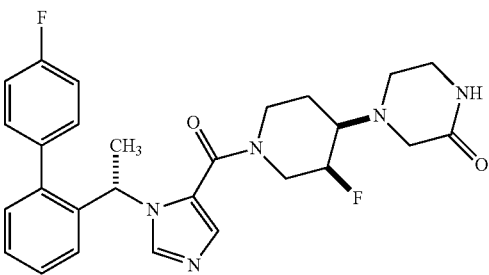 [SMILES: C[C@@H](c1ccccc1-c1ccc(F)cc1)n1cncc1C(=O)N1CC[C@@H](N2CCNC(=O)C2)[C@@H](F)C1] | 494.2 | (CD₃OD) δ: 8.03 (s, 1H), 7.52-6.94 (m, 8H), 6.56 (br, 1H), 5.88 (br, 1H), 5.03-4.90 (m, 1H), 4.69-3.86 (m, 3H), 3.33-3.12 (m, 4H), 2.93-2.57 (m, 4H), 1.88-1.22 (m, 5H) |
| 31 | 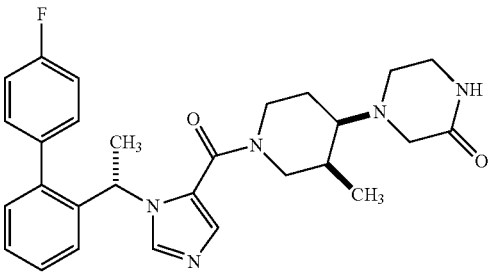 [SMILES: C[C@H]1CN(C(=O)c2cncn2[C@@H](C)c2ccccc2-c2ccc(F)cc2)CC[C@H]1N1CCNC(=O)C1] | 490.2 | (CD₃OD) δ: 8.07 (s, 1H), 7.70-6.85 (m, 9H), 5.99 (br, 1H), 4.90-3.55 (m, 4H), 3.43-3.25 (m, 2H), 3.24-2.91 (m, 2H), 2.88-2.46 (m, 3H), 2.44-2.02 (m, 2H), 1.68 (d, J = 6.4 Hz 3H), 1.68-1.48 (m, 2H), 1.15-0.89 (m, 2H). |
| 32 | 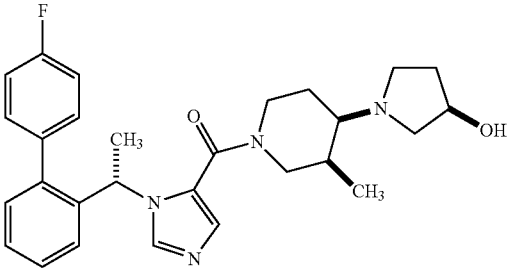 [SMILES: C[C@H]1CN(C(=O)c2cncn2[C@@H](C)c2ccccc2-c2ccc(F)cc2)CC[C@H]1N1CC[C@@H](O)C1] | 477.2 | (CD₃OD) δ: 7.93 (s, 1H), 7.37 (br, 2H), 7.28-7.00 (m, 6H), 6.43 (br, 1H), 5.97 (br, 1H), 4.50-4.39 (m, 4H), 3.15-2.20 (m, 7H), 2.15-1.85 (m, 3H), 1.69-1.42 (m, 5H), 1.15-0.74 (m, 2H). |
| 33 | 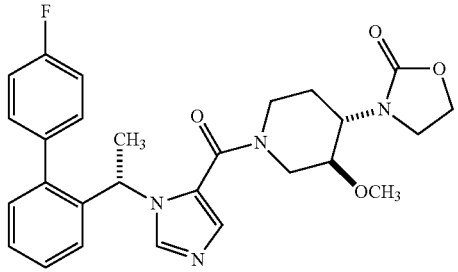 [SMILES: CO[C@H]1CN(C(=O)c2cncn2[C@@H](C)c2ccccc2-c2ccc(F)cc2)CC[C@@H]1N1CCOC1=O] | 493.2 | (CD₃OD) δ: 8.05 (s, 1H), 7.56-6.54 (m, 9H), 5.95 (br, 1H), 4.60-3.90 (m, 4H), 3.72-3.34 (m, 5H), 3.16-2.36 (m, 4H), 1.91-0.98 (m, 5H). |

Example 7

Preparation of Compound 34

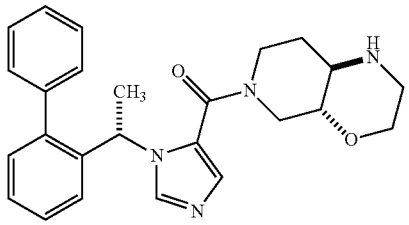

Step A—Preparation of Int 7-1

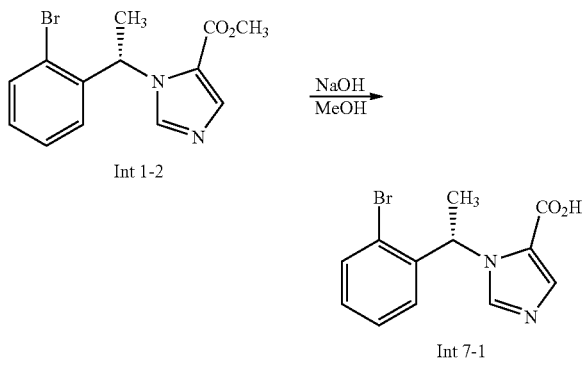

Into a 3000-mL 4-necked round-bottom flask purged and maintained with an inert atmosphere of nitrogen was placed a solution of Int 1-2 (75 g, 242 mmol, 1.00 equiv) in methanol (937.5 mL). To this was slowly added aq. NaOH (937.5 mL, 40%). The resulting solution was stirred for 2 h at 40° C., cooled then concentrated under vacuum. The residual solution was adjusted to pH 6 with HCl (1 M), then extracted with 6×1000 mL of ethyl acetate. The organic layers were combined, washed with 1×1000 mL of brine, dried over anhydrous sodium sulfate and concentrated under vacuum. This reaction was repeated once to provide total 80 g of crude product. The crude product was purified using Prep-SFC with the following conditions: Column, ChiralPak IC, 5×25 cm, 5um; mobile phase, $CO_2$ (70%), methanol (30%); Detector, UV 220 nm which resulted in 53 g (74%) of Int 7-1 as a white solid. $^1$H-NMR (CD$_3$OD) δ 7.74-7.98 (s, 1H), 7.65-7.74 (s, 1H), 7.62-7.63 (dd, 1H), 7.35-7.41 (m, 1H), 7.21-7.27 (m, 1H), 7.01-7.04 (m, 1H), 6.61-6.68 (m, 1H), 3.31-3.33 (d, 3H). LCMS (ES, m/z): 295 [M+H]$^+$.

Step B—Preparation of Int 7-2

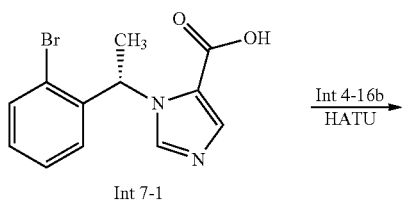

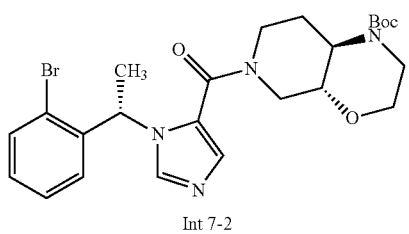

To a stirred solution of Int 7-1 (1.8 g, 6.2 mmol), Int 4-16b (1.5 g, 6.2 mmol) and Et$_3$N (1.25 g, 12.4 mmol) in 30 mL of DMF was added 3.5 g (9.3 mmol) of HATU. The reaction was allowed to stir at room temperature for 3 hour then diluted with water (20 mL) and extracted with ethyl acetate (30 mL×3). The combined organic extracts were dried over anhydrous sodium sulfate, filtered and concentrated in vacuo to provide crude product which was purified using column chromatography (ethyl acetate) to provide compound Int 7-2 (2.8 g, 87.5%). $^1$H NMR (CDCl$_3$) δ 7.80 (s, 1H), 7.54 (d, J=7.8 Hz, 1H), 7.28-7.22 (m, 1H), 7.17-7.09 (m, 2H), 6.84 (s, 1H), 6.19 (s, 1H), 4.71-4.26 (m, 2H), 3.93-3.43 (m, 5H), 3.33-3.13 (m, 2H), 3.10-2.88 (m, 3H), 2.55-2.43 (m, 2H), 1.85 (d, J=6.7 Hz, 3H), 1.44 (s, 11H). MS-ESI (m/z): 519.2 (M+H)$^+$.

Step C—Preparation of Compound 34

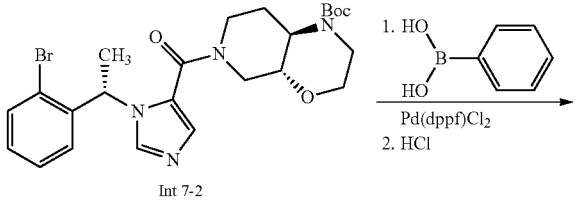

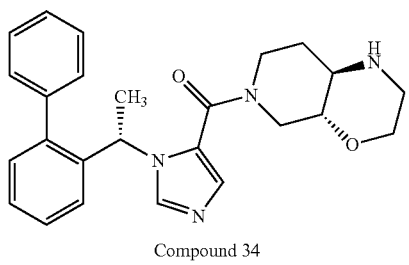

Compound 34

A mixture of compound Int 7-2 (150 mg, 0.29 mmol), phenylboronic acid (53 mg, 0.435 mmol), Pd(dppf)Cl$_2$ (22 mg, 0.029 mmol) and potassium carbonate (100 mg, 0.72 mmol) in dimethoxyethane (3 mL) and water (1 mL) was degassed with nitrogen and stirred at 100° C. overnight. After cooling to room temperature, the mixture was filtered, diluted with water (5 mL) and extracted with ethyl acetate (10 mL×2). The combined organic extracts were dried over anhydrous sodium sulfate, filtered and concentrated in vacuo to provide crude product (100 mg) as yellow oil which was dissolved in ethyl acetate (2 mL) and treated with HCl/EtOAc (3 mL). The solution was allowed to stir at room temperature for 30 min, concentrated and purified using preparative HPLC to provide compound 34 (30 mg, 37%) as a white solid. ¹H NMR (CD₃OD) δ 7.94 (s, 1H), 7.39-7.09 (m, 6H), 6.98 (d, J=8.2 Hz, 2H), 6.79-6.57 (m, 1H), 5.92 (d, J=7.0 Hz, 1H), 4.66-4.24 (m, 2H), 3.96-3.62 (m, 5H), 3.46 (s, 1H), 2.95-2.59 (m, 4H), 2.43 (s, 1H), 2.02-1.61 (m, 5H). MS-ESI (m/z): 417.3 (M+H)⁺.

The following compounds 35-44, of the present invention, were prepared starting from Int 7-2 and an appropriately substituted arylboronic acid using a standard Suzuki coupling reaction similar to that described in Example 7 above.

| Cmpd | Structure | M + H | 1H NMR |
|---|---|---|---|
| 35 | 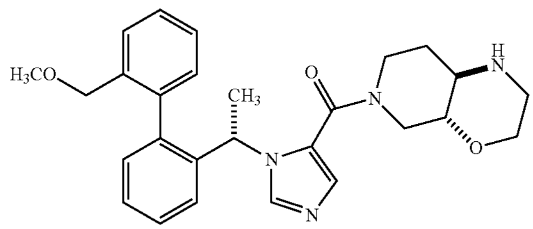 | 461 | (CD₃OD) δ: 7.73-7.10 (m, 10H), 5.71 (br, 1H), 4.29-3.82 (m, 5H), 3.63-3.60 (m, 2H), 3.21 (s, 3H), 2.91-2.48 (m, 5H), 1.83-1.65 (m, 4H), 1.30- 1.17 (m, 1H). |
| 36 | 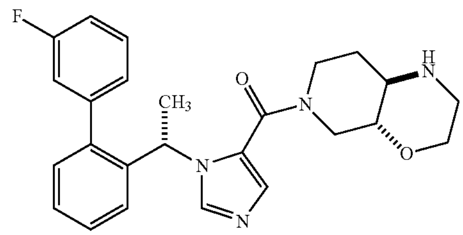 | 435.2 | (CD₃OD) δ: 7.99 (s, 1H), 7.49-7.31 (m, 3H), 7.25-6.79 (m, 6H), 5.89 (q, J = 6.7 Hz, 1H), 4.63-4.23 (m, 2H), 3.78 (br, 2H), 3.51 (br, 1H), 2.98-2.60 (m, 4H), 2.49 (br, 2H), 1.73 (d, J = 6.7 Hz, 3H), 1.32-0.97 (m, 2H). |
| 37 | 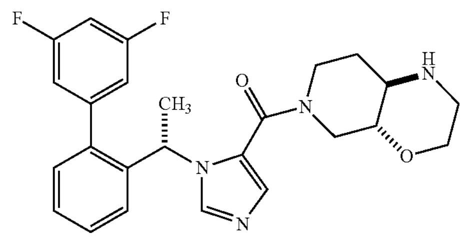 | 453.2 | (CD₃OD) δ: 8.06 (s, 1H), 7.42-7.41 (m, 2H), 7.30-7.19 (m, 2H), 7.11-6.67 (m, 4H), 5.94 (q, J = 7.0 Hz, 1H), 4.62-4.18 (m, 1H), 3.82-3.81 (m, 2H), 3.53 (br, 1H), 3.17-2.32 (m, 6H), 1.92-1.67 (m, 4H), 1.40-0.97 (m, 1H). |
| 38 | 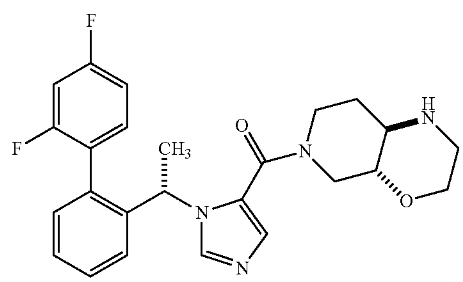 | 453.2 | (CD₃OD) δ: 7.99-7.87 (m, 1H), 7.40 (d, J = 3.5 Hz, 2H), 7.34-6.70 (m, 6H), 5.71 (q, J = 6.3 Hz, 1H), 4.63-4.14 (m, 2H), 3.97-3.69 (m, 2H), 3.52 (br, 1H), 3.00-2.57 (m, 4H), 2.48 (s, 1H), 1.90-1.58 (m, 4H), 1.27-1.20 (m, 1H). |
| 39 | 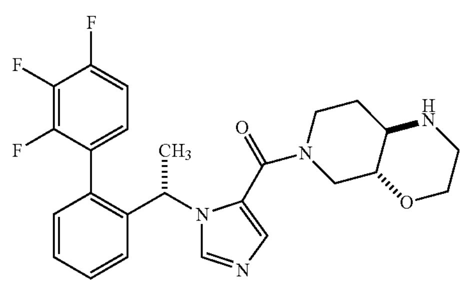 | 471.1 | (CD₃OD) δ: 8.09-7.97 (m, 1H), 7.89-7.55 (m, 1H), 7.47 (s, 2H), 7.33-7.08 (m, 4H), 5.84-5.69 (m, 1H), 4.66 (m, 1H), 4.20 (s, 3H), 3.68 (br, 1H), 3.11 (s, 2H), 2.92-2.55 (m, 3H), 2.04-1.63 (m, 4H), 1.52-1.28 (m, 1H). |

-continued

| Cmpd | Structure | M + H | 1H NMR |
|---|---|---|---|
| 40 | 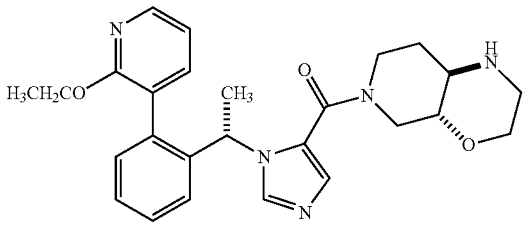 | 462.2 | (CD₃OD) δ: 8.16 (d, J = 3.5 Hz, 1H), 7.83 (s, 1H), 7.59 (s, 1H), 7.51-7.32 (m, 3H), 7.23-7.06 (m, 2H), 7.03-6.96 (m, 1H), 5.77 (q, J = 6.8 Hz, 1H), 4.46-4.03 (m, 4H), 3.84 (d, J = 9.4 Hz, 2H), 3.65-3.53 (m, 1H), 3.02-2.82 (m, 3H), 2.73 (t, J = 12.5 Hz, 1H), 2.54 (s, 1H), 1.85-1.72 (m, 4H), 1.33-1.04 (m, 4H). |
| 41 | 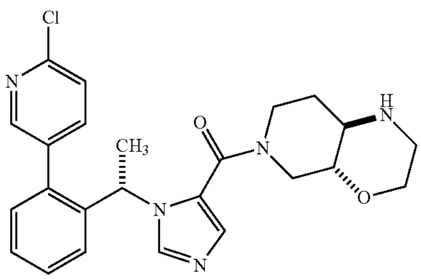 | 452.2 | (CD₃OD) δ: 8.64 (s, 1H), 8.14 (br, 1H), 7.94 (dd, J = 8.0 Hz, J2 = 2.0 Hz, 1H), 7.65-6.60 (m, 6H), 6.09 (q, J = 6.8 Hz, 1H), 4.49-4.05 (m, 2H), 3.80-3.46 (m, 3H), 2.92 (br, 2H), 2.53 (br, 2H), 1.99 (d, J = 6.8 Hz, 3H), 1.56-1.51 (m, 1H), 1.43-1.05 (m, 2H). |
| 42 | 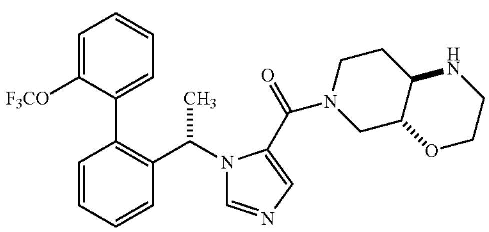 | 501.2 | (CD₃OD) δ: 7.86 (s, 1H), 7.65-7.35 (m, 5H), 7.35-7.01 (m, 4H), 5.67 (q, J = 7.2 Hz, 1H), 4.50-3.85 (m, 3H), 3.81 (t, J = 12 Hz, 1H), 3.64-3.45 (m, 1H), 3.01-2.65 (m, 4H), 2.53-2.42 (m, 1H), 1.88-1.61 (m, 4H), 1.30-1.09 (m, 1H). |
| 43 | 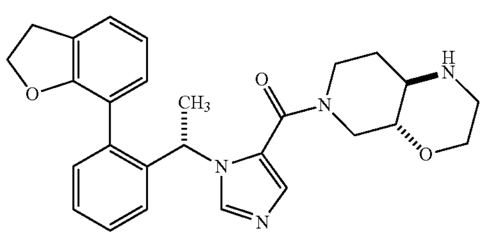 | 459.2 | (CD₃OD) δ: 7.67 (s, 1H), 7.43-7.31 (m, 2H), 7.26-7.11 (m, 2H), 7.04 (s, 1H), 6.95-6.74 (m, 3H), 5.86 (br, 1H), 4.45 (br, 2H), 3.90-3.67 (m, 2H), 3.59-3.43 (m, 1H), 3.23 (t, J = 8.0 Hz, 2H), 2.95-2.72 (m, 3H), 2.71-2.32 (m, 4H), 1.81 (br, 3H), 1.70-1.57 (m, 1H), 1.30-1.09 (m, 1H). |
| 44 | 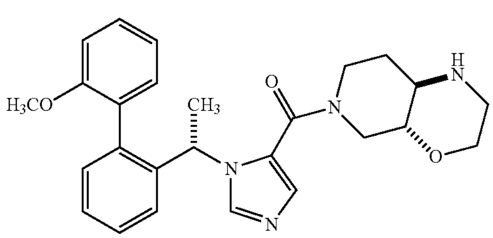 | 447.2 | (CD₃OD) δ: 7.73 (s, 1H), 7.41-7.30 (m, 3H), 7.20-6.76 (m, 6H), 5.73 (td, J1 = 12.7 Hz, J2 = 6.6 Hz, 1H), 4.44-3.99 (m, 2H), 3.85-3.68 (m, 3H), 3.62-3.41 (m, 2H), 3.00-2.63 (m, 4H), 2.56-2.28 (m, 2H), 1.84-1.64 (m, 4H), 1.30-1.13 (m, 1H) |

Example 8

Preparation of Compound 45

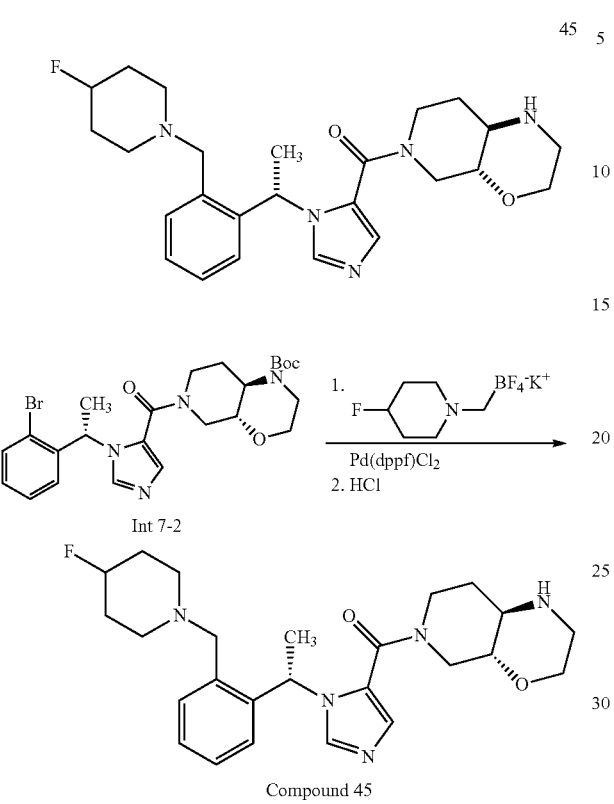

To a stirred solution of compound Int 7-2 (150 mg, 0.29 mmol) in toluene (1 mL), ethanol (0.5 mL) and water (0.5 mL) was added the tetrafluoroborate salt (165 mg, 0.68 mmol), $K_2CO_3$ (95.2 mg, 0.68 mmol) and Pd(dppf)Cl$_2$ (33.6 mg, 0.046 mmol) sequentially under nitrogen. The reaction mixture was allowed to stir at 100° C. overnight then cooled to room temperature. The mixture was filtered and the filtrate was concentrated in vacuo. The residue was then dissolved in ethyl acetate (2 mL) and treated with HCl/EtOAc (3 mL). The solution was allowed to stir at room temperature for 30 min, concentrated and purified using preparative HPLC to provide Compound 45 (66 mg) as a white solid. $^1$H NMR (CDCl$_3$) δ: 7.87 (s, 1H), 7.23-7.10 (m, 4H), 6.81 (m, 1H), 6.19-6.18 (m, 1H), 4.73-2.33 (m, 17H), 1.89-1.80 (m, 8H), 1.57-1.26 (m, 2H). MS-ESI (m/z): 456.2 (M+H)$^+$.

Example 9

Preparation of Compound 46

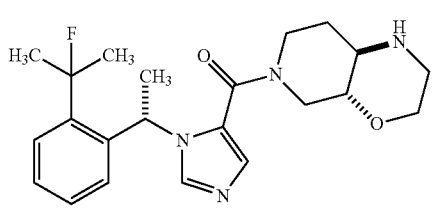

Step A—Preparation of Int 9-1

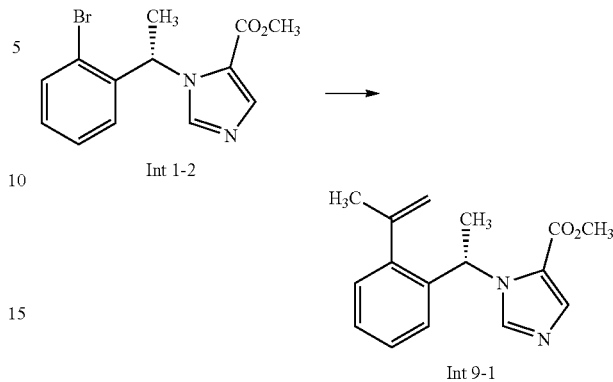

A mixture of compound Int 1-2 (5 g, 16.2 mmol), 2-isopropenyl tetrafluoroborate potassium salt (4.8 g, 32.4 mmol), potassium carbonate (6.7 mg, 48.5 mmol) and Pd(dppf)Cl$_2$ (591 mg, 1.62 mmol) toluene (50 mL), ethanol (50 mL) and water (25 mL) was allowed to stir at 100° C. under nitrogen overnight. The mixture was cooled to room temperature and then filtered. The filtrate was concentrated under vacuum and the crude product was purified using column chromatography on silica gel (petroleum: ethyl acetate=1:1) to provide the compound Int 9-1 (3.8 g, yield: 86%) as yellow oil.

Step B—Preparation of Int 9-2

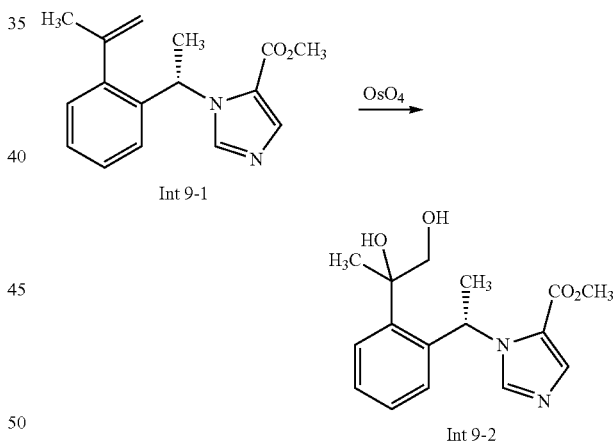

To solution of compound Int 9-1 (2.8 g, 10.4 mmol) in tetrahydrofuran (80 mL) and H$_2$O (10 mL) was added 4-methylmorpholine 4-oxide (3.6 g, 31.1 mmol) and OsO$_4$ (0.5 g). The mixture was allowed to stir at 80° C. under N$_2$ overnight. TLC (petroleum ether: ethyl acetate=1:1) showed the reaction was complete and the reaction mixture was quenched by the addition of aqueous sodium sulfite (500 mL), and then the mixture was allowed to stir at room temperature for 2 hours. The mixture was filtered through a Celite pad, and the filtrate was extracted with ethyl acetate (100 mL×3). The combined organic layers were dried over Na$_2$SO$_4$, filtered and concentrated under vacuum to provide the crude product Int 9-2 (3 g, 95%), which was used directly in next step.

Step C—Preparation of Int 9-3

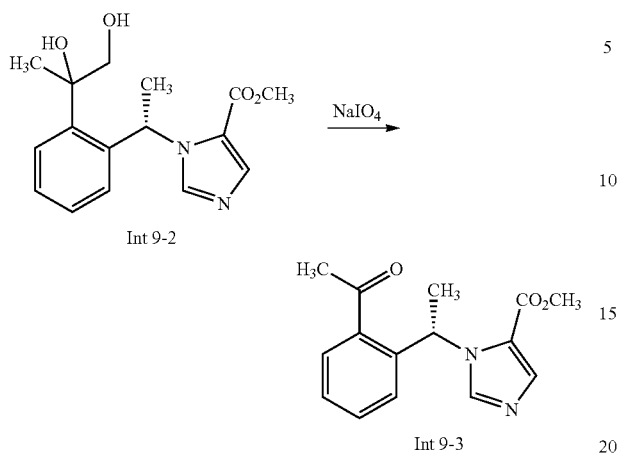

To a solution of compound Int 9-2 (3 g, 3.28 mmol) in tetrahydrofuran (80 mL) and H$_2$O (10 mL) was added NaIO$_4$ (6.6 g, 31.1 mmol). The mixture was allowed to stir at 80° C. under N$_2$ for 2 hours. The resulting mixture was concentrated and water (100 mL) and acetate (100 mL) was added. The aqueous layer was extracted with ethyl acetate (3×100 mL) and the combined organic layers was washed with brine, dried over sodium sulfate then filtered. The filtrate was concentrated under vacuum, and crude product was purified using column chromatography on silica gel (petroleum: ethyl acetate=1:1) to provide the compound Int 9-3 (1.8 g, 64.3%).

Step D—Preparation of Int 9-4

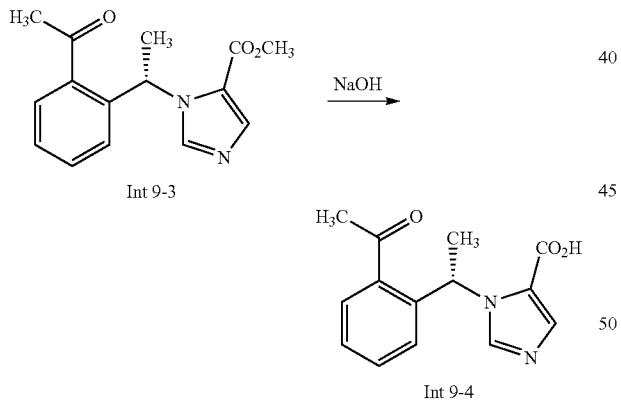

To a stirred solution of compound Int 9-3 (0.8 g, 2.94 mmol) in 20 mL of methanol was added a solution of sodium hydroxide (0.117 g, 2.94 mmol) in 5 mL of H$_2$O at room temperature. The mixture was allowed to stir at room temperature for 24 hours. The resulting mixture was then added carefully 3N HCl solution till pH=5-6. The aqueous layer was extracted with ethyl acetate (3×10 mL) and the combined organic layer was washed with brine, dried over sodium sulfate then filtered. The filtrate was concentrated under vacuum to provide the compound Int 9-4 which was used in next step without further purification (600 mg, 79.4%). MS-ESI (m/z): 259.2 (M+H)$^+$.

Step E—Preparation of Int 9-5

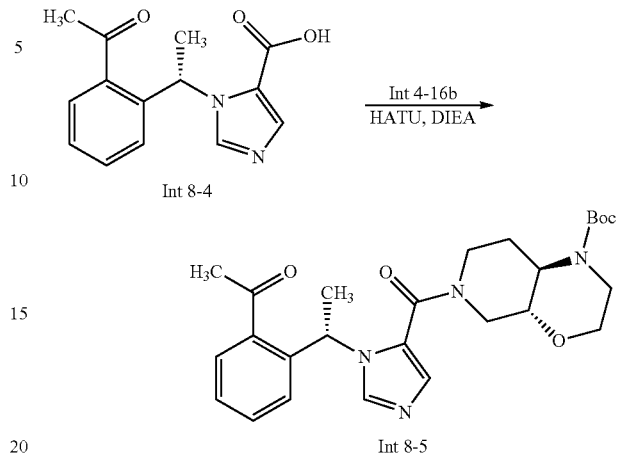

To a stirred solution of compound 9-4 (319.9 mg, 1.24 mmol), Int 4-16b (300 mg, 1.24 mmol), DIEA (240 mg, 1.85 mmol) in 5 mL of N,N-dimethylformamide was added HATU (706.6 mg, 1.85 mmol) at 25° C. The reaction was allowed to stir at room temperature for 2.5 hour. The resulting mixture was extracted with dichlomethane (3×10 mL). The combined organic layer was washed dried over sodium sulfate then filtered. The filtrate was concentrated in vacuo to dryness, the residue was purified using silica gel chromatography (petroleum ether: ethyl acetate=1:1) to provide compound Int 9-5 (0.5 g, 83.3%). MS-ESI (m/z): 483.2 (M+H)$^+$.

Step F—Preparation of Int 9-6

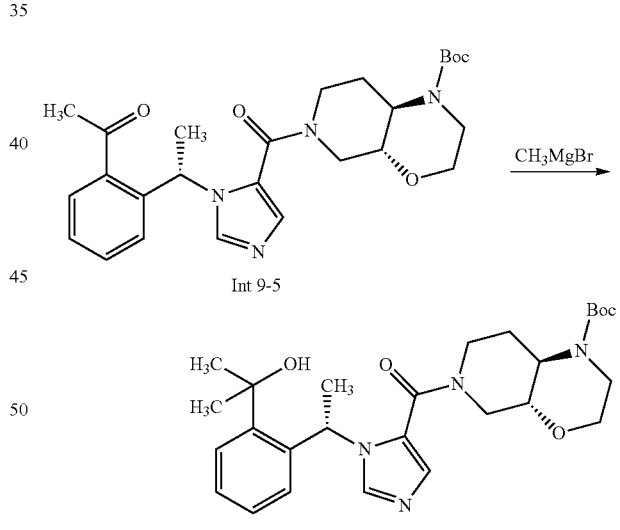

To a stirred solution of compound Int 9-5 (500 mg, 1.03 mmol) in anhydrous tetrahydrofuran (10 mL) was added methylmagnesium bromide (3 M, 0.69 mL, 2.06 mmol) at 0° C. under nitrogen. The mixture was allowed to stir at 25° C. for 1 hour. TLC (petroleum ether: ethyl acetate=3:1) showed the starting material was consumed completely. The reaction was quenched with saturate ammonia chloride solution (5 mL) and the aqueous was extracted with ethyl acetate (5 mL×3). The combined organic layer was dried over anhydrous sodium sulfate then filtered. The filtrate was concentrated in vacuo to provide the crude product, which was purified using preparative-TLC (petroleum ether: ethyl acetate=1:1) to provide compound Int 9-6 (450 mg, 87.7%) as oil. MS-ESI (m/z): 499.2 (M+H)⁺.

Step G—Preparation of Int 9-7

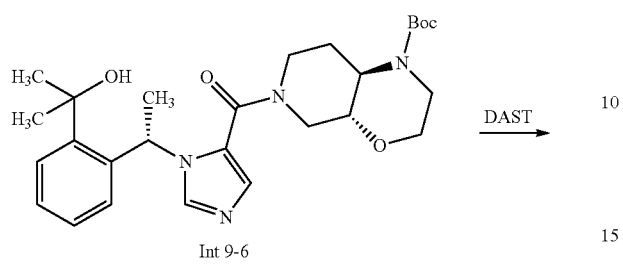

Int 9-6

Int 9-7

To a solution of compound Int 9-6 (160 mg, 0.32 mmol) in DCM (20 mL) was added DAST (diethylaminosulfur trifluoride, 103.0 mg, 0.64 mmol) at 0° C. The solution was allowed to stir at 25° C. for 3 h. The result solution was quenched with water and the aqueous was extracted with DCM (3×10 mL). The combined organic layer was washed with brine, dried over anhydrous sodium sulfate then filtered. The filtrate was concentrated in vacuo to provide 160 mg of compound Int 9-7 which was used directly in next step without further purification (yield 75.0%). MS-ESI (m/z): 501.2 (M+H)⁺.

Step H—Preparation of Compound 46

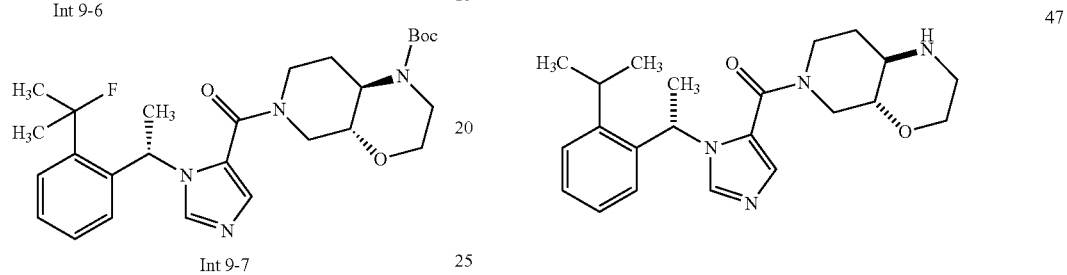

Int 9-7

Compound 46

To a stirred solution of compound Int 9-7 (160 mg, 0.32 mmol) in ethyl acetate (2 mL) was added HCl/EtOAc (3 mL). The solution was allowed to stir at room temperature for 20 min then concentrated in vacuo. The residue was purified using preparative-HPLC to provide Compound 46 (100 mg, 78.1%) as white solid. ¹H NMR (CD₃OD) δ: 8.09 (s, 1H), 7.43-7.10 (m, 4H), 6.79-6.61 (br, 1H), 6.43 (s., 1H), 4.74-4.24 (br, 2H), 3.84-3.64 (m, 2H), 3.37 (d, J=18.4 Hz, 1H), 3.22-2.82 (m, 3H), 2.78 (s., 2H), 2.40 (s., 1H), 1.90 (d, J=6.7 Hz, 3H), 1.84-1.72 (m, 5H), 1.69-1.60 (m, 1H), 1.69-1.60 (m, 1H), 1.35 (d, J=6.3 Hz, 1H), 1.11-0.88 (br, 1H). MS-ESI (m/z): 401.2 (M+H)⁺.

Example 10

Preparation of Compound 47

47

Step A—Preparation of Int 10-1

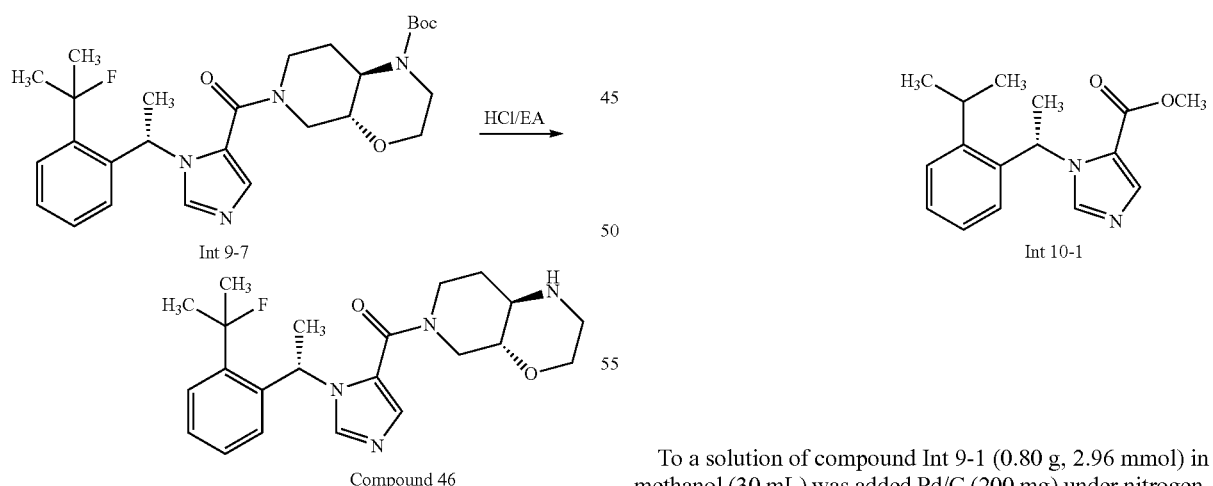

Int 8-1

Int 10-1

To a solution of compound Int 9-1 (0.80 g, 2.96 mmol) in methanol (30 mL) was added Pd/C (200 mg) under nitrogen. The suspension was degassed under reduced pressure and purged with hydrogen three times. The mixture was stirred under hydrogen (50 psi) at room temperature for 3 h before the mixture was filtered through a Celite pad and concentrated in vacuo to provide compound Int 10-1 (0.8 g, 99.4%), which was used for the next step without further purification. MS-ESI (m/z): 273.0 (M+H)⁺.

Step B—Preparation of Int 10-2

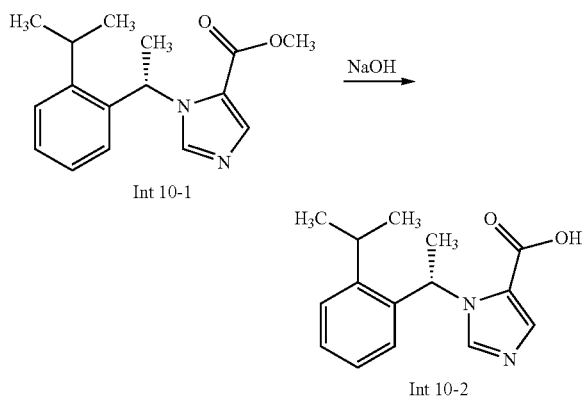

To a solution of compound Int 10-1 (0.8 g, 2.94 mmol) in methanol (15 mL) was added a solution of NaOH (0.47 g, 11.76 mmol) in H$_2$O (3 mL) and the reaction mixture was allowed to stir at room temperature overnight. The organic solvent was removed under reduced pressure and the aqueous phase was acidified with 6 N HCl to pH-5, and then concentrated to provide crude product, which was washed with ethyl acetate. The organic phase was concentrated in vacuo to dryness to provide desired compound Int 10-2 (0.7 g, 92.3%) as yellow solid. MS-ESI (m/z): 259.3 (M+H)$^+$.

Step C—Preparation of Compound 47

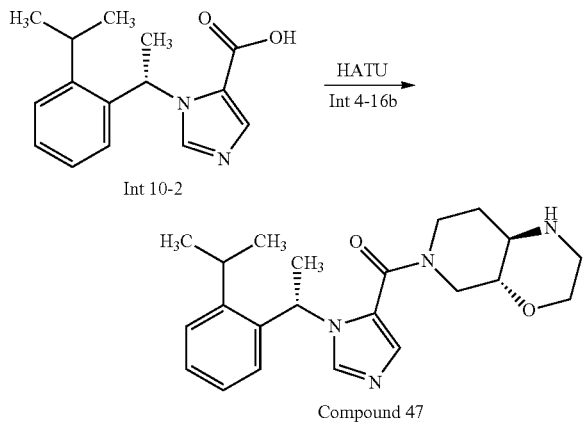

A mixture of compound Int 10-2 (100 mg, 0.39 mmol), HATU (176.6 mg, 0.46 mmol) and disopropylethylamine (150 mg, 1.16 mmol) in 2 mL of dichloromethane was allowed to stir at room temperature for 30 mins, then compound Int 4-16b (93.8 mg, 0.39 mmol) was added into above reaction solution. The mixture was allowed to stir at room temperature for 2 hrs, and then poured into water. The aqueous was extracted with dichloromethane (3×10 mL). The combined organic layer was dried over anhydrous sodium sulfate, concentrated in vacuo to provide the crude product. The crude product was dissolved in HCl/EtOAc (5 mL, 4N) and stirred at room temperature for 2 hours. The reaction mixture was concentrated in vacuo and the residue was purified using preparative HPLC to provide Compound 47 (55 mg, 37% in two steps). $^1$H NMR (CD$_3$OD) δ: 8.05 (s, 1H), 7.36-7.29 (m, 2H), 7.22-7.14 (m, 2H), 6.63 (br, 1H), 6.18 (q, J=6.0 Hz, 1H), 4.55-4.25 (m, 1H), 3.75 (br, 2H), 3.65-3.40 (m, 2H), 3.27-3.15 (m, 1H), 2.97-2.28 (m, 6H), 1.85 (d, J=6.8 Hz, 3H), 1.70-1.55 (m, 1H), 1.23 (d, J=6.0 Hz, 6H). MS-ESI (m/z): 383.2 (M+H)$^+$.

Compound 48 was prepared starting from Int 6-2 and an alkenylboronic acid using a standard Suzuki coupling reaction similar to that described in Example 10 above.

| Cmpd | Structure | M + H | 1H NMR |
|---|---|---|---|
| 48 | 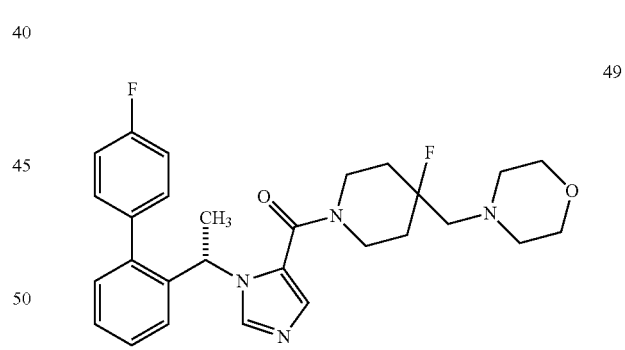 | 409.3 | (CD$_3$OD) δ: 8.09 (br, 1H), 7.44-7.26 (m, 2H), 7.23-7.09 (m, 2H), 6.66 (br, 1H), 6.19 (q, J = 6.3 Hz, 1H), 4.46 (br, 1H), 3.75-3.43 (m, 4H), 3.08-2.33 (m, 6H), 2.14-1.41 (m, 13H). |

Example 11

Preparation of Compound 49

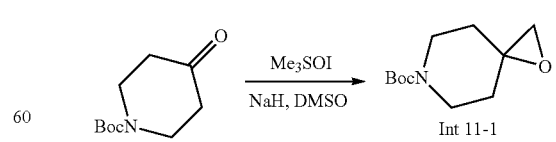

Step A—Preparation of Int 11-1

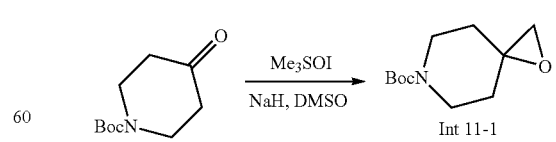

Me$_3$SOI (233 mg, 1.06 mmol) was added to a suspension of NaH (25 mg, 1.06 mmol) in DMSO (10 mL) cooled to 0° C. The reaction mixture was then allowed to warm to room temperature and stirred for 40 min before compound 1 (200 mg, 1.0 mmol) was added to the reaction mixture. The reaction was allowed to stir at room temperature for 1 hour and then warmed up to 55° C. and stirred for 2 hours. The reaction mixture was then poured into NaHSO₃ aq. and extracted with ethyl acetate (3×20 mL). The combined organic extracts were washed with water, dried over anhydrous sodium sulfate then filtered. The filtrate was concentrated in vacuo to provide the product Int 11-1. ¹H NMR (Methanol-d₄) δ: 3.84-3.61 (m, 2H), 3.56-3.33 (m, 2H), 2.69 (s, 2H), 1.75 (dd, J₁=13.2 Hz, J₂=9.2 Hz, 2H), 1.47-1.42 (m, 11H).

Step B—Preparation of Int 11-2

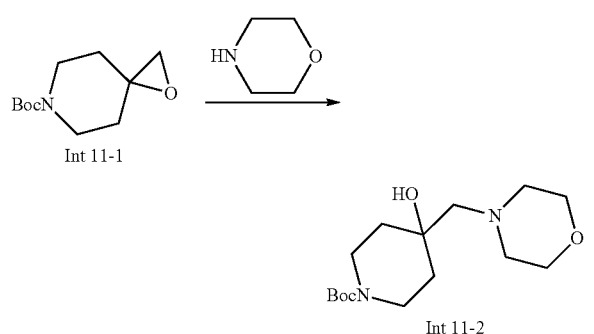

To a solution of compound Int 11-1 (100 mg, 0.47 mmol) in 5 mL of ethanol was added morpholine (0.1 mL, 0.96 mmol). The mixture was allowed to stir at 60° C. for 2 hours. The reaction was concentrated in reduced pressure to provide the crude product which was purified using preparative TLC (ethyl acetate: methanol=7:1) to provide the product Int 11-2. ¹H NMR (Methanol-d₄) δ: 3.75 (d, J=12.8 Hz, 2H), 3.71-3.60 (m, 4H), 3.14 (br, 2H), 2.56 (br, 4H), 2.30 (s, 2H), 1.57-1.48 (m, 4H), 1.43 (s, 9H). MS-ESI (m/z): 301.1 (M+H)⁺

Step C—Preparation of Int 11-3

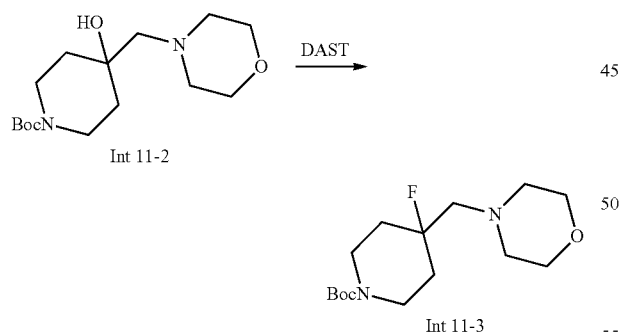

To a stirred solution of compound Int 11-2 (250 mg, 0.83 mmol) in anhydrous dichloromethane (10 mL) was added DAST (268 mg, 1.67 mmol) at 0° C. After the mixture was allowed to stir at 0° C. for 1.5 hours under N₂ atmosphere the reaction was quenched by ice water and the organic layer was separated and dried over sodium sulfate then filtered. The filtrate was concentrated in vacuo to provide the crude product, which was purified using preparative TLC (petroleum ether: ethyl acetate=1:1) to provide the product 4. MS-ESI (m/z): 303.3 (M+H)⁺.

Step D—Preparation of Int 11-4

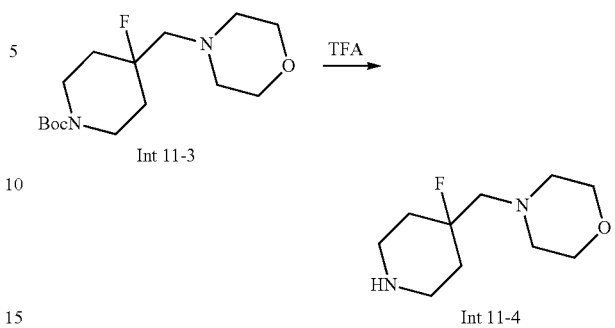

To a mixture of compound Int 11-3 (170 mg, 0.56 mmol) in dichloromethane (5 mL), was added trifluoroacetic acid (5 mL). The mixture was allowed to stir at room temperature for 1 h and the reaction mixture was basified by triethylamine and then concentrated in vacuo to provide 120 mg of the crude product Int 11-4. MS-ESI (m/z): 203.3 (M+H)⁺.

Step E—Preparation of Compound 49

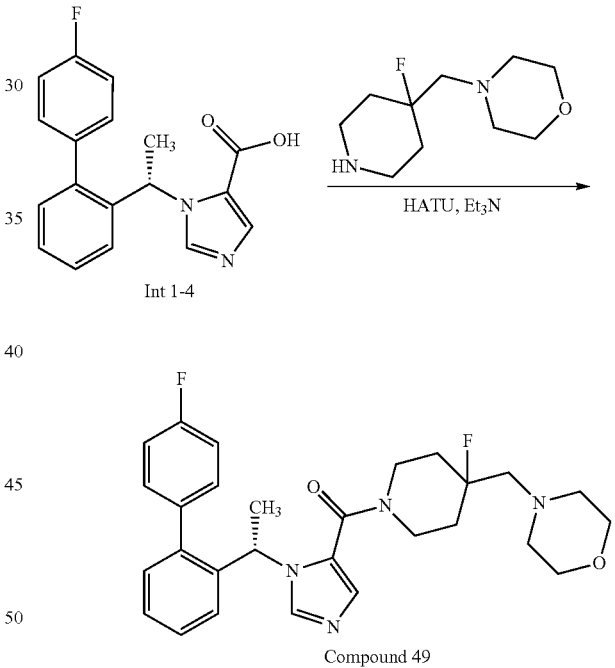

A mixture of compound Int 1-4 (100 mg, 0.32 mmol), HATU (184 mg, 0.48 mmol) and triethylamine (0.1 mL, 0.72 mmol) in N,N-dimethylformamide (4 mL) was allowed to stir at room temperature for 30 minutes then compound Int 11-4 (120 mg, 0.59 mmol) was added. The mixture was allowed to stir at room temperature for 2 hours. The reaction mixture was concentrated in vacuo to provide the crude product, which was purified using preparative HPLC to provide the compound 49. ¹H NMR (Methanol-d₄) δ: 7.95 (s, 1H), 7.47-7.24 (m, 4H), 7.23-7.02 (m, 4H), 6.78 (s, 1H), 5.89 (s, 1H), 4.41-4.06 (m, 2H), 4.02-3.72 (m, 2H), 3.63 (br, 4H), 2.94 (br, 2H), 2.48 (br, 4H), 2.31 (br, 2H), 1.72 (br, 5H). MS-ESI (m/z): 495.2 (M+H)⁺.

Example 12

Preparation of Compound 50

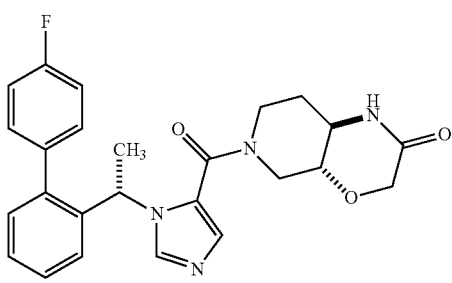

50

Step A—Preparation of Int 12-1

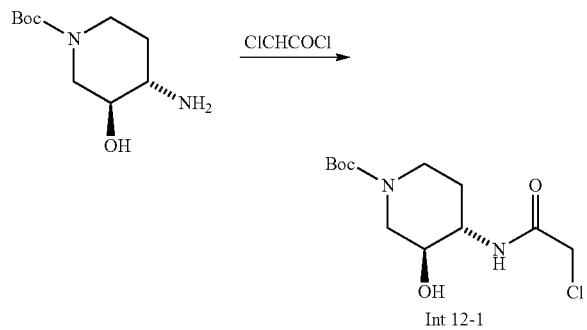

To a stirred solution of trans-rac-N-Boc-4-amino-3-hydroxypiperidine (400 mg, 1.85 mmol) and triethylamine (561 mg, 5.55 mmol) in dichloromethane (5 mL) was added chloroacetyl chloride (230 mg, 2.035 mmol) dropwise at 0° C. The reaction mixture was allowed to stir at 0° C. for 20 min then poured into water and the aqueous was extracted with ethyl acetate (3×10 mL). The combined organic washings were dried over sodium sulfate and filtered. The filtrate was concentrated in vacuo to provide 380 mg of crude compound Int 12-1, which was used in the next step without further purification. MS-ESI (m/z): 237, 293 (M+H−56, M+H)$^+$.

Step B—Preparation of Int 12-2

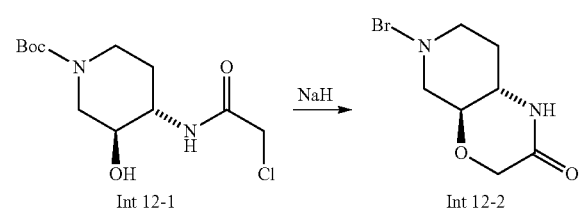

To a stirred solution of compound Int 12-1 (380 mg, 1.33 mmol) in tetrahydrofuran (20 mL) was added sodium hydride (83 mg, 4 mmol) in portion at 0° C. The mixture was allowed to stir at room temperature overnight. The reaction was quenched with saturated ammonium chloride at 0° C. and the mixture was allowed to stir at room temperature for 10 mins. The aqueous was extracted with ethyl acetate (3×10 mL) and the combined organic extracts were dried over sodium sulfate and filtered. The filtrate was concentrated in vacuo and purified using preparative TLC (petroleum ether:ethyl acetate=5:1) to provide 280 mg of compound Int 12-2. MS-ESI (m/z): 201, 257 (M+H−56, M+H)$^+$.

Step C—Preparation of Int 12-3

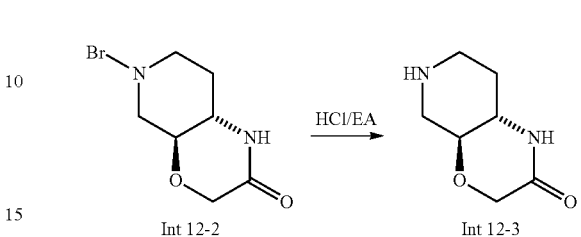

A mixture of compound Int 12-2 (280 mg, 1.71 mmol) in hydrochloric acid/ethyl acetate (10 ml) was allowed to stir at 40° C. for 30 minutes. The reaction mixture was concentrated in vacuo to provide the compound Int 12-3 which was used in next step without further purification. MS-ESI (m/z): 156 (M+H)$^+$.

Step D—Preparation of Compound 50

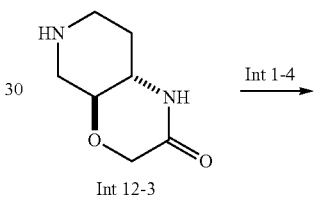

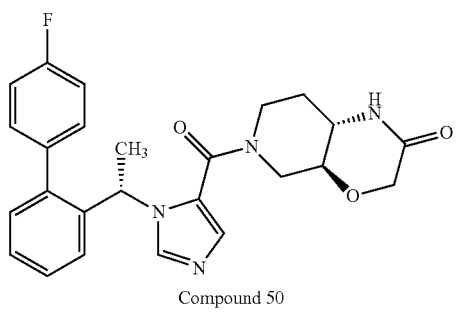

A mixture of compound Int 1-4 (280 mg, 0.9 mmol), HATU (513 mg, 1.35 mmol), and DIEA (348 mg, 2.70 mmol) in dichloromethane (6 mL) was allowed to stir at room temperature for 15 mins, then compound Int 12-3 (124 mg, 0.645 mmol) in DMF (1 mL) was added. The mixture was allowed to stir at room temperature for another 3 hours. The reaction mixture was purified using preparative-HPLC to provide compound 50. $^1$H NMR (CDCl$_3$) δ: 7.40 (s, 1H), 7.30-7.09 (m, 7H), 6.76 (s, 1H), 6.21 (s, 1H), 6.00-5.98 (s, 1H), 4.36-3.89 (m, 4H), 3.29 (s, 1H), 2.75-2.60 (m, 2H), 2.17 (s, 1H), 1.83-1.80 (m, 1H), 1.67-1.65 (m, 3H), 1.25-1.19 (m, 2H). MS-ESI (m/z): 449 (M+H)$^+$.

Example 13

Preparation of Compound 51

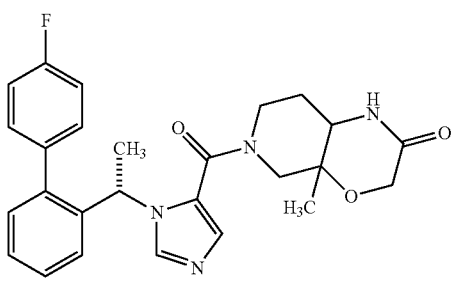

Step A—Preparation of Int 13-1

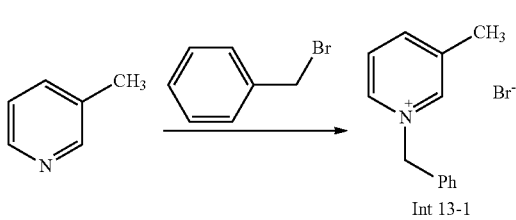

To a solution of 3-methylpyridine (10 g, 0.11 mol) in acetone (30 mL) was added benzylbromide (18.36 g, 0.11 mol) in one portion and the solution was refluxed for 5 h, cooled to ambient temperature and concentrated in vacuo to provide 27 g of compound Int 13-1 as brown oil which was used directly in next step without further purification.

Step B—Preparation of Int 13-2

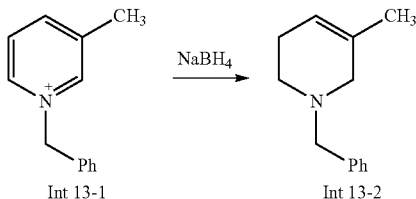

To a solution of compound Int 13-1 (27 g, 0.11 mol) in ethanol (500 mL) was added NaBH$_4$ (8 g, 0.21 mol) in portions in an ice bath. The mixture was warmed to room temperature and stirred at room temperature for 6 hours. The reaction was quenched with water (300 mL) and the aqueous was extracted with ethyl acetate (3×200 mL). The combined organic layers were washed with brine, dried over sodium sulfate then filtered. The filtrate was concentrated in vacuo to provide 20 g of compound Int 13-2 as yellow oil which was used in next step directly without further purification. $^1$H NMR (CDCl$_3$) δ: 7.53-7.51 (m, 2H), 7.38-7.33 (m, 3H), 5.54 (s, 1H), 3.92 (s, 2H), 314 (s, 2H), 2.84 (t, J=5.2 Hz, 2H), 2.32 (s, 2H), 1.64 (s, 3H). MS-ESI (m/z): 188.1 (M+H)$^+$.

Step C—Preparation of Int 13-3

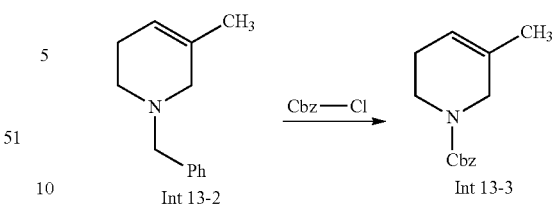

To a solution of compound Int 13-2 (13 g, 69.4 mmol) in toluene (250 mL) was added benzyl chloroformate (35.52 g, 208.2 mmol). The mixture was heated at 90° C. for 8 h then cooled to ambient temperature. The reaction solution was concentrated and the residue was purified using column chromatography (petroleum: ethyl acetate=50:1, 40:1, 30:1) to provide compound Int 13-3. MS-ESI (m/z): 232.2 (M+H)$^+$.

Step D—Preparation of Int 13-4

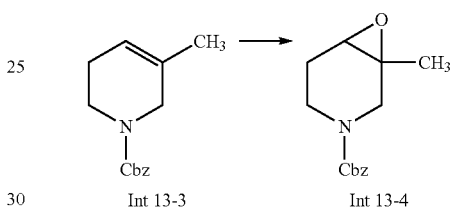

To a stirred solution of compound Int 13-3 (3.5 g, 15.1 mmol) in dichloromethane (50 mL) was added 3-chloroperoxybenzoic acid (3.9 g, 22.7 mmol) in portions at 0° C. The reaction mixture was allowed to stir at 0° C. for 1 h then allowed to warm to room temperature and stirred for another 5 hours. The reaction was quenched with 10% sodium sulfite and the aqueous layer was extracted with dichloromethane (3×20 mL). The combined organic layers were washed with 10% sodium hydroxide and dried over sodium sulfate then filtered. The filtrate was concentrated in vacuo and the residue was purified using column chromatography eluted with petroleum ether: ethyl acetate=30:1, 15:1, 10:1 to provide 3.1 g of compound Int 13-4 as yellow oil. $^1$H NMR (CDCl$_3$) δ 7.36-7.27 (m, 5H), 5.13 (s, 2H), 3.80-3.60 (m, 2H), 3.41-3.31 (m, 2H), 2.25-1.80 (m, 3H), 1.37-1.35 (m, 3H).

Step E—Preparation of Int 13-5

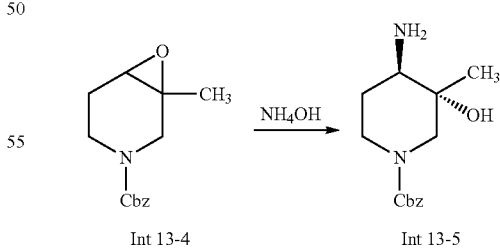

A mixture of compound Int 13-4 (8.8 g, 35.6 mmol) and ammonium chloride (20 g, 37.4 mmol) in ethanol (80 mL) and aqueous ammonia (200 mL) was refluxed for 5 hours. The reaction was cooled to room temperature and basified to pH=10. The solvent was concentrated in vacuo and the residue was purified using column chromatography (100% ethyl acetate, ethyl acetate:methanol=30:1, 15:1 to provide 5.6 g of compound Int 13-5 as yellow oil. $^1$H NMR (CDCl$_3$) δ 7.29 (br, 5H), 5.51 (br, 5H), 5.07 (br, 2H), 4.16-4.05 (m, 2H), 3.17-3.14 (m, 1H), 2.80-2.67 (m, 2H), 2.02-1.95 (m, 1H), 1.60-1.58 (m, 1H), 1.22-1.17 (m, 3H). MS-ESI (m/z): 265.1 (M+H)$^+$.

Step F—Preparation of Int 13-6

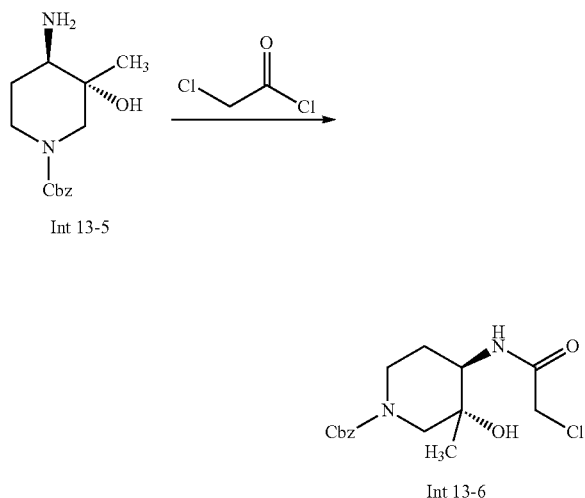

Int 13-6

To a stirred solution of the compound Int 13-5 (0.5 g, 1.89 mmol) and triethylamine (573 mg, 5.67 mmol) in dichloromethane (5 mL) was added dropwise chloroacetyl chloride (235 mg, 2.08 mmol) at 0° C. The mixture was allowed to stir at 0° C. for 30 min then poured into water (5 mL) and the aqueous was extracted with dichloromethane (3×10 mL). The combined organic layers were dried over sodium sulfate and filtered. The filtrate was concentrated in vacuo to provide 700 mg of compound Int 13-6 as black oil which was used in the next step without further purification. MS-ESI (m/z): 341.1 (M+H)$^+$.

Step G—Preparation of Int 13-7

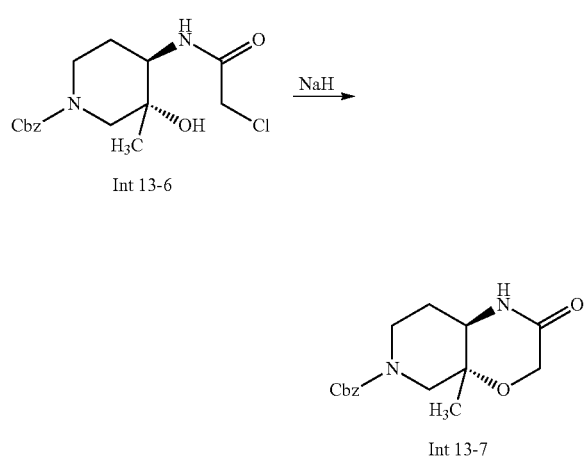

To a stirred solution of compound Int 13-6 (700 mg, 1.89 mmol) in anhydrous tetrahydrofuran (5 mL) was added sodium hydride (227 mg, 5.67 mol, 60% in oil) in portions at 0° C. and the mixture was allowed to stir at room temperature for 2 hours. The reaction was quenched with saturated ammonium chloride (10 mL), and the aqueous was extracted with ethyl acetate (10 mL×3). The combined organic extracts were dried over sodium sulfate and filtered. The filtrate was concentrated in vacuo and purified using preparative TLC (100% ethyl acetate) to provide 360 mg of compound Int 13-7 as colorless oil. $^1$H NMR (CDCl$_3$) δ: δ 7.35-7.23 (m, 5H), 5.19-5.10 (m, 2H), 4.41-4.11 (m, 4H), 3.47 (dd, J=8.4 Hz, J=4.0 Hz, 1H), 2.85-2.69 (m, 2H), 1.87-1.71 (m, 2H), 1.51-1.47 (m, 1H), 1.47-1.01 (m, 3H). MS-ESI (m/z): 305.1 (M+H)$^+$.

Step H—Preparation of Int 13-8

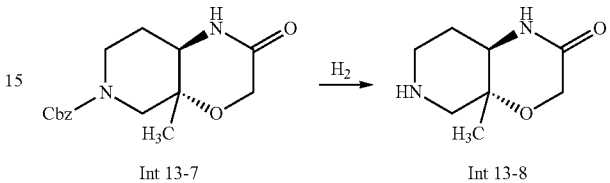

To a solution of compound Int 13-7 (360 mg, 1.18 mmol) in methanol (10 mL) was added Pd(OH)$_2$/C (100 mg). The mixture was stirred under hydrogen (50 psi) atmosphere at room temperature for 5 hours. The mixture was filtered and the filtrate was concentrated in vacuo to provide compound Int 13-8 as colorless oil which was used directly in next step without further purification. MS-ESI (m/z): 171.1 (M+1)

Step I—Preparation of Compound 51

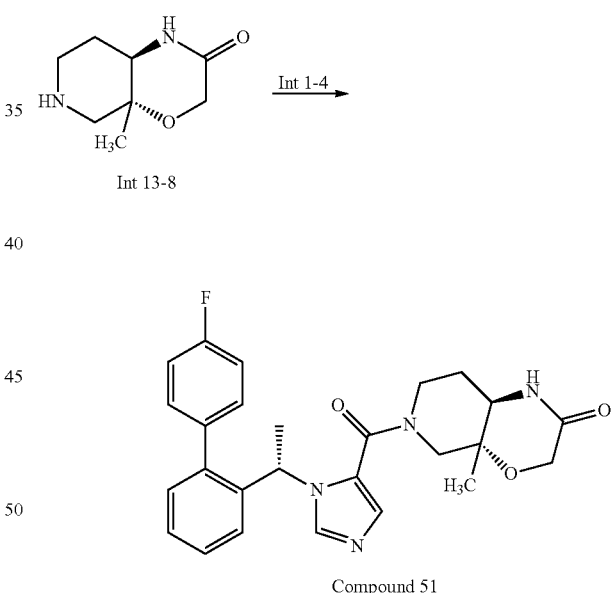

Compound 51

A mixture of Int 1-4 (274 mg, 0.88 mmol), HATU (502 mg, 1.32 mmol) and DIPEA (341 mg, 2.64 mmol) in dichloromethane (6 mL) was allowed to stir at room temperature for 10 mins then compound Int 13-8 (150 mg, 0.88 mmol) was added. The mixture was allowed to stir at room temperature for 2 h. The reaction mixture was filtered and the filtrate was purified using preparative HPLC to provide 50 mg of the desired compound 51. $^1$H NMR (CDCl$_3$) δ 7.63 (s, 1H), 7.21-7.02 (m, 8H), 6.80 (br, 1H), 6.02 (br, 1H), 4.24-4.04 (m, 4H), 3.43-3.40 (m, 1H), 2.62-2.56 (m, 2H), 1.98-1.94 (m, 2H), 1.63-1.62 (m, 3H), 1.34-1.31 (m, 1H), 0.97-0.78 (m, 3H). MS-ESI (m/z): 463.2 (M+H)$^+$.

Example 14

Preparation of Compounds 52 and 53

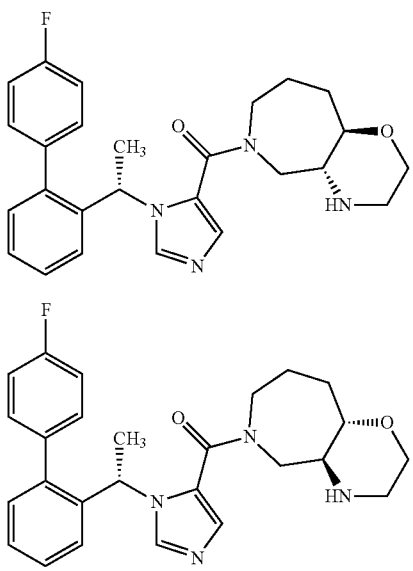

Step A—Preparation of Int 14-1

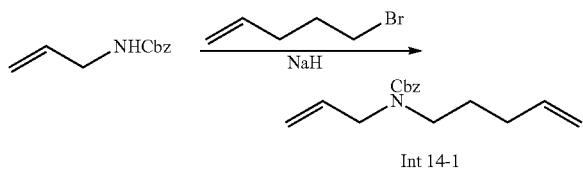

To a suspension of sodium hydride (2.24 g, 56 mmol, 60% in oil) in N, N-dimethylformamide (50 mL) was added N-Cbz allylamine (5.0 g, 26 mmol). The mixture was allowed to stir at room temperature for 30 min before 5-bromopentene (3.87 g, 26 mmol) was added. The mixture was allowed to stir at 40° C. for 3 h, cooled to room temperature and poured into water (50 mL). The aqueous phase was extracted with ether acetate (3×30 mL) and the combined organic extracts were dried over sodium sulfate then filtered. The filtrate was concentrated in vacuo and the residue was purified using column chromatography eluted with petroleum ether: ethyl acetate=50:1 to provide 4.1 g of compound Int 14-1 as yellow oil. MS-ESI (m/z): 260.2 (M+H)$^+$.

Step B—Preparation of Int 14-2

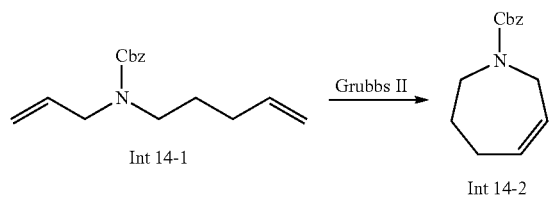 [SMILES: C=CCCCN(CC=C)C(=O)OCc1ccccc1 ; "Grubbs II" ; O=C(OCc1ccccc1)N1CC=CCCC1]

To a solution of compound Int 14-1 (30.0 g, 0.12 mol) in dichloromethane (500 mL) was added Grubbs II (0.8 g, 0.94 mmol). The mixture was refluxed for 16 h under N$_2$ atmosphere then cooled to room temperature. The organic solution was concentrated in vacuo and the residue was purified using column chromatography eluted with petroleum ether: ethyl acetate=50:1, 30:1, 10:1 to provide 14 g of compound Int 14-2 as brown oil. $^1$H NMR (CDCl$_3$) δ: 7.35-7.26 (m, 5H), 5.80-5.74 (m, 2H), 5.15-5.14 (m, 2H), 4.00-3.95 (m, 1H), 3.65-3.53 (m, 3H), 2.34-2.29 (m, 3H), 1.85-1.79 (m, 1H). MS-ESI (m/z): 232.2 (M+H)$^+$.

Step C—Preparation of Int 14-3

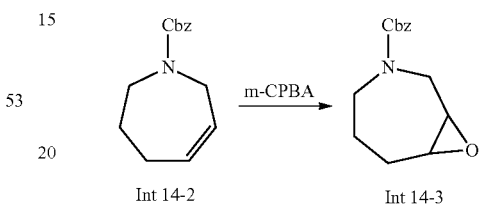

To a solution of compound Int 14-2 (10.0 g, 43.3 mmol) in dichloromethane (200 mL) was added 3-chloroperoxybenzoic acid (22.4 g, 130 mmol) in portions at 0° C. The reaction mixture was allowed to warm to room temperature and stirred for another 16 hours. The reaction was quenched with 10% sodium sulfite and the aqueous layer was extracted with dichloromethane (3×100 mL). The combined organic layer was washed with 30% sodium hydroxide (aq.) and dried over sodium sulfate then filtered. The filtrate was concentrated in vacuo and the residue was purified using column chromatography eluted with petroleum ether: ethyl acetate=10:1, 5:1, 3:1 to provide 3.3 g of compound Int 14-3 as yellow oil. MS-ESI (m/z): 248.2 (M+H)$^+$.

Step D—Preparation of Int 14-4

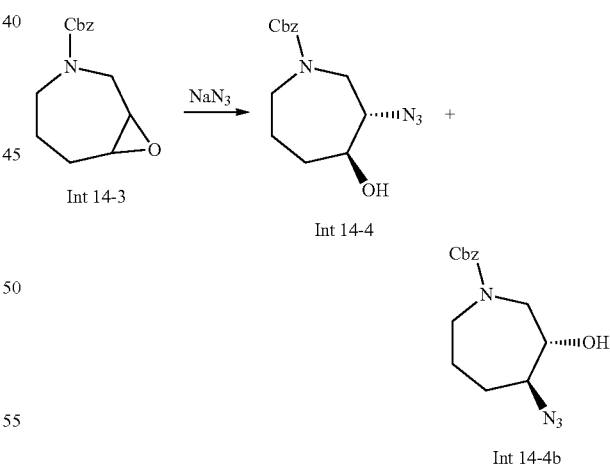

A mixture of compound Int 14-3 (5.0 g, 20.2 mol) in methanol (140 mL) was added ammonium chloride (2.7 g, 50.5 mmol) and sodium azide (5.25 g, 80.8 mmol). The reaction mixture was refluxed for 16 hours. The reaction was cooled to room temperature and quenched by addition of NaClO (5~7%, 50 mL) dropwise. After gas evolution ceased, the mixture was brought to pH 9-10 with saturated sodium dicarbonate (80 mL) and then extracted with ethyl acetate (3×50 mL). The combined organic layers were dried over anhydrous sodium sulfate then filtered. The filtrate was concentrated in vacuo to provide the crude product which was purified using column chromatography eluted with petroleum ether: ethyl acetate=5:1, 3:1 to provide 2.6 g of compound Int 14-4 $^1$H NMR (MeOD) δ: 7.39-7.30 (m, 5H), 5.18-5.11 (m, 2H), 3.83-3.52 (m, 3H), 3.28-3.06 (m, 3H), 1.93-1.74 (m, 2H), 1.72-1.68 (m, 1H), 1.44-1.36 (m, 1H) and 1.1 g of compound Int 14-4b as yellow oil $^1$H NMR (CDCl$_3$) δ: 7.35-7.26 (m, 5H), 5.14 (s, 2H), 3.75-3.60 (m, 3H), 3.45-3.34 (m, 3H), 2.51-2.48 (m, 1H), 2.14-2.06 (m, 2H), 1.79-1.74 (m, 2H). MS-ESI (m/z): 291.2 (M+H)$^+$.

Step E—Preparation of Int 14-5

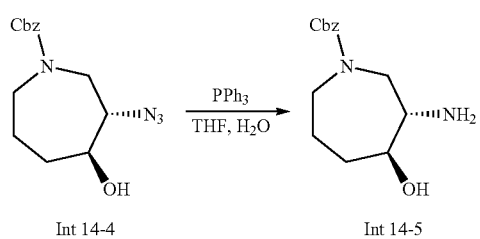

To a solution of compound Int 14-4 (2.6 g, 8.97 mmol) in tetrahydrofuran (65 mL) and water (4.5 mL) was added triphenylphosphine (2.82 g, 10.76 mmol). The reaction mixture was allowed to stir at room temperature for 24 hours. The organic solvent was removed under reduced pressure and the aqueous was acidified to pH 2-3 and extracted with ethyl acetate (3×20 mL). The aqueous was basified to pH 9-10 then concentrated in vacuo. The residue was purified using column chromatography eluted with ethyl acetate: methanol=10:1, 5:1, 3:1 to provide 1.32 g of compound Int 14-5 as yellow oil. MS-ESI (m/z): 265.2 (M+H)$^+$.

Step F—Preparation of Int 14-6

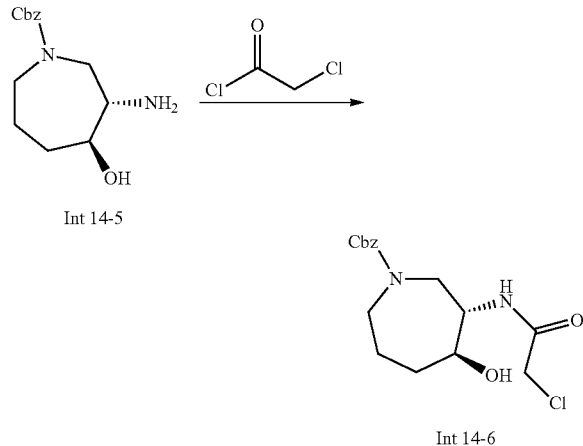

To a stirred solution of the compound Int 14-5 (0.5 g, 1.89 mmol) and triethylamine (573 mg, 5.67 mmol) in dichloromethane (15 mL) was added dropwise chloroacetyl chloride (235 mg, 2.08 mmol) at 0° C. then the mixture was stirred for 30 mins. The reaction mixture was poured into water (10 mL) and the aqueous was extracted with dichloromethane (3×10 mL). The combined organic extracts were dried over sodium sulfate then filtered. The filtrate was concentrated in vacuo to provide 715 mg of compound Int 14-6 as brown oil, which was used in the next step without further purification. MS-ESI (m/z): 341.1 (M+H)$^+$.

Step G—Preparation of Int 14-7

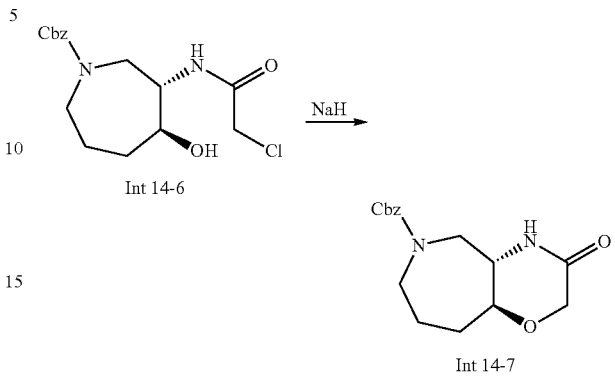

To a stirred solution of compound Int 14-6 (715 mg, 1.89 mmol) in anhydrous tetrahydrofuran (15 mL) was added sodium hydride (227 mg, 5.67 mol, 60% in oil) in portions at 0° C. and the mixture was allowed to stir at room temperature for 16 hours. The reaction was quenched with saturated ammonium chloride (10 mL) and the aqueous was extracted with ether acetate (3×10 mL). The combined organic extracts were dried over sodium sulfate then filtered. The filtrate was concentrated in vacuo and purified using preparative TLC (100% ethyl acetate) to provide compound 9 as white solid. $^1$H NMR (MeOD) δ: 7.37-7.32 (m, 5H), 5.13 (s, 2H), 4.10-4.07 (m, 2H), 3.64-3.36 (m, 6H), 2.15-1.68 (m, 5H). MS-ESI (m/z): 305.1 (M+H)$^+$.

Step H—Preparation of Int 14-8

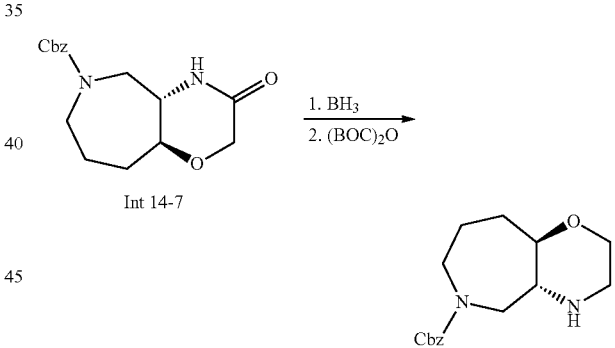

To a stirred solution of compound Int 14-7 (0.2 g, 0.66 mmol) in anhydrous tetrahydrofuran (2 mL) was added borane-tetrahydrofuran complex (4 mL, 3.93 mmol) dropwise at 0° C. and the mixture was allowed to stir at 40° C. for 30 minutes. The reaction was quenched with methanol and the solvent was concentrated in vacuo to provide a colorless liquid which was dissolved in ethyl acetate (4 mL) and water (2 mL). Potassium carbonate (273 mg, 1.98 mmol) was added followed by (Boc)$_2$O (431 mg, 1.98 mmol) and the reaction solution was allowed to stir at room temperature for 16 hours. The aqueous was extracted with ether acetate three times then the organic washings were dried over sodium sulfate then filtered. The filtrate was concentrated in vacuo and the residue was purified using preparative TLC (petroleum: ethyl acetate=1:1) to provide 100 mg of compound Int 14-8 as yellow oil. MS-ESI (m/z): 391.1 (M+H)$^+$.

Step I—Preparation of Int 14-9

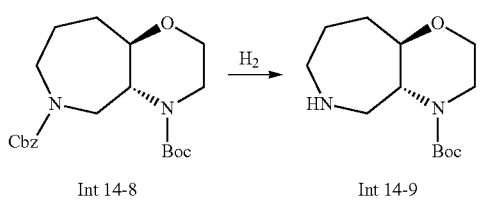

Int 14-8     Int 14-9

To a solution of compound Int 14-8 (450 mg, 1.15 mmol) in methanol (15 mL) was added wet Pd/C (100 mg). The mixture was stirred under hydrogen (50 psi) atmosphere at room temperature for 2 hours. The mixture was filtered and the filtrate was concentrated in vacuo to provide compound Int 14-9 as colorless solid which was used directly in next step without further purification. MS-ESI (m/z): 257.2 (M+1)$^+$.

Step J—Preparation of Compounds 52 and 53

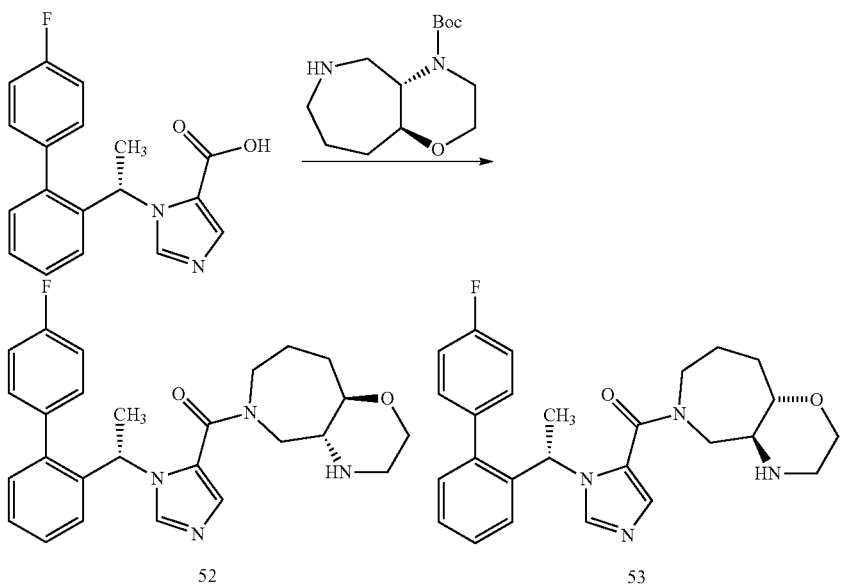

52     53

A mixture of acid Int 1-4 (182 mg, 0.59 mmol), HATU (333 mg, 0.87 mmol) and N-ethyl-N-isopropylpropan-2-amine (226 mg, 1.75 mmol) in dichloromethane (4 mL) was allowed to stir at room temperature for 10 min before compound Int 14-9 (150 mg, 0.59 mmol) was added. The mixture was allowed to stir at room temperature for 4 h, water (5 mL) was added and the aqueous was extracted with dichloromethane (5 mL×3). The combined organic extracts were dried over sodium sulfate then filtered. The filtrate was concentrated in vacuo. The resulting residue was treated with 4N HCl/ethyl acetate (20 mL) at room temperature for 30 minutes. The reaction solution was concentrated in vacuo and the residue was purified using SFC and then preparative HPLC to provide 33 mg of Compound 52 (CDCl$_3$) δ: 7.61 (s, 1H), 7.31-6.93 (m, 8H), 6.63 (s, 1H), 6.11 (m, 1H), 3.71-3.69 (m, 2H), 3.49-3.26 (m, 3H), 3.08-2.69 (m, 4H), 2.35 (m, 1H), 1.81-1.44 (m, 8H). MS-ESI (m/z): 449.3 (M+H)$^+$ and 35 mg of Compound 53 as white solid (CDCl$_3$) δ: 7.47 (s, 1H), 7.27-7.03 (m, 8H), 6.91 (s, 1H), 5.95 (q, J=6.4 Hz, 1H), 3.79-2.78 (m, 10H), 2.38 (br, 1H), 1.94-1.58 (m, 7H). MS-ESI (m/z): 449.3 (M+H)$^+$.

Example 15

Determination of IC$_{50}$ in a Cocktail Assay for CYPs 1A2, 2C9, 2C19, 2D6 and 3A4

This assay was performed in a standard 96-well plate design. IC$_{50}$ values were calculated from the percent inhibition observed for each test compound at 6 concentrations (for example, 0.0032, 0.016, 0.08, 0.4, 2 and 10 µM). The incubation substrate mix contains 10 µM phenacetin (1A2), 5 µM diclofenac (2C9), 30 µM mephenytoin (2C19), 5 µM dextromethorphan (2D6) and 2 µM midazolam (3A4), 0.1 mg/mL protein human liver microsomes (BD Gentest), 1 mM NAPDH, 3.3 mM MgCl$_2$ and 100 mM potassium phosphate buffer (pH 7.4). The production of the metabolite of each probe substrate was determined after incubation for 10 min at 37° C. Quantitation of the metabolite peak area ratio against an internal standard (tolbutamide) was determined by LC/MS/MS analysis following acetonitrile treatment of the incubations.

| Probe Substrate | Reaction (isoform) | Metabolite Detected |
|---|---|---|
| Phenacetin | O-deethylation (CYP1A2) | Acetaminophen |
| Diclofenac | 4'-hydroxylation (CYP2C9) | 4'-Hydroxydiclofenac |
| Mephenytoin | 4'-hydroxylation (CYP2C19) | 4'-Hydroxymephenytoin |
| Dextromethorphan | O-demethylation (CYP2D6) | Dextrorphan |
| Midazolam | 1'-hydroxylation (CYP3A4) | 1'-Hydroxymidazolam |

Samples were analyzed in the MRM mode with a SCIEX API-4000 mass spectrometer (Applied Biosystems, Foster City, Calif.), with a Shimadzu LC-20 AD pump (Shimadzu corporation, Kyoto, JP) and a CTC PAL autosampler (Agilent Technologies, Switzerland). A Phenomenex, Luna, 5

μm, 100A, 2.00×30 mm HPLC column was used for the separation. The mobile phases were: (A) 0.1% formic acid in water and (B) 0.1% formic acid in acetonitrile. The binary gradient was as follows.
AutoSampler: CTC PAL

| | |
|---|---|
| Loop Volume 1 (user entered) | 100 μL |
| Loop Volume 2 (user entered) | 100 μL |
| Actual Injection Volume | 10.0 μL |

Binary Gradient
Total Flow: 700 μL/min

| Time (min) | A (%) | B (%) |
|---|---|---|
| 0.01 | 98 | 2 |
| 0.40 | 30 | 70 |
| 0.80 | 2 | 98 |
| 1.00 | System Controller | Stop |

The mass spectrum parameters were as follows:
MS Parameters:

| | |
|---|---|
| CUR Curtain gas (psi): | 20 |
| GS1 Ion source gas1 (psi): | 50 |
| GS2 Ion source gas2 (psi): | 60 |
| IS IonSpray voltage (V): | 5500 |
| TEM Temperature (° C.): | 600 |
| ihe Interface heater (on/off): | ON |
| CAD Collision Activated Dissociation (psi): | 10 |
| EP Entrance Potential (V): | 10 |
| CXP Collision Cell Exit Potential (V): | 12 |

The LC/MS/MS parameters for the analytes were as follows.
LC/MS/MS Analysis

| | Ion Transition | | DP | CE | RT |
|---|---|---|---|---|---|
| Compound | Q1 Mass (m/z) | Q3 Mass (m/z) | Declustering Potential (V) | Collision Energy (V) | Retention Time (min) |
| Acetominophen | 152.2 | 110 | 40 | 23 | 0.36 |
| 4'-Hydroxydiclofenac | 312 | 231 | 32 | 29 | 0.72 |
| 4'-Hydroxymephenytoin | 235.3 | 150.3 | 45 | 25 | 0.49 |
| Dextrorphan | 258.2 | 157.2 | 40 | 55 | 0.42 |
| 1'-hydroxymidazolam | 342.2 | 203.2 | 40 | 30 | 0.53 |
| IS | 271.1 | 155.3 | 69 | 25 | 0.71 |

The peak area ratio of the analyte to the internal standard was used to quantify the metabolite. The values of peak area ratios in the presence of test compound were compared to those of maximum or minimum controls and were expressed as % inhibition by interpolating between the maximum and minimum peak area ratios. Incubations with no inhibitor were defined as the maxima.
The following equation was used to calculate the % inhibition:

[1−[(X−Low control)/(High control−Low control)]]*100

For the $IC_{50}$ calculation, SigmaPlot was used to plot the mean % inhibition versus the test compound concentrations and for non-linear regression analysis of the data. Depending on the range of data points defining the inhibition curve, the data may have been fit to the 4-parameter logistic equation.

Example 16

Determination of $IC_{50}$ vs CYP11B1/CYP11B2 by Measurement of Cortisol/Aldosterone Synthesis This assay was performed in a standard 384-well plate design using cultured V79 cells stably expressing human CYP11B1 or human CYP11B2. Test compounds at 10 concentrations (for example, 10000, 3333.3, 1111.1, 370.4, 123.5, 41.2, 13.7, 4.6, 1.5 and 0.5 nM) were added in 384-well plate after the cell-seeding procedure. The incubation substrate contains 1500 nM RSS for CYP11B1 assay/ 750 nM DOC for CYP11B2 assay. The Cortisol/Aldosterone production of cell culture supernatant was determined by Cortisol/Aldosterone HTRF kit after for about 15 hours incubation at RT (protect from light). $IC_{50}$ (nM) values were calculated from the percent inhibition observed for each test compound at 10 concentrations.

The assay plate was read using Envision (Perkin Elmer, Waltham, Mass.) at 665 nm and 590 nm (using Filter Barcode of 217#, 205#; Mirror Barcode of 446#).
The Envision setting parameters were as follows:
Envision Parameters:

| | |
|---|---|
| Light source: | Laser |
| Top mirror (Barcode): | 446# |
| Bottom mirror (Barcode): | None |
| Emission Filter (Barcode): | 217# |
| $2^{nd}$ emission Filter (Barcode): | 205# |
| Measurement height (mm): | 6.5 |
| Delay (μs): | 50 |
| Window time (μs): | 400 |
| Number of sequential windows: | 1 |
| Time between flashes | 16600 |
| Number of flashes | 10 |
| Number of flashes for $2^{nd}$ detector | 10 |

Data are analyzed using Assay Data Analyzer. All ratio data (665 nm/590 nm) are back calculated according to the standard curve, resulting in Cortisol/Aldosterone concentrations. $IC_{50}$ (nM) values are reported as the Inflection Point (IP) of a four parameter fit of the titration data.
The following equation was used to calculate the % inhibition:

% Activity=100×{1−(Sample_back calculated Cortisol/Aldosterone concentration−LC_back calculated Cortisol/Aldosterone concentration)/ (HC_back calculated Cortisol/Aldosterone concentration−LC_back calculated Cortisol/Aldosterone concentration)}

Curve Fitting: Four Parameter Logistic:

$$y = n + \frac{m-n}{1+\left(\frac{i}{x}\right)^p}$$

Example 17

The table below provides IC$_{50}$ (nM) data for compounds of Formula (I) obtained using the assays described in Examples 15 and 16, above.

| Cmpd | CYP3A4 | CYP1A2 | CYP2C9 | CYP2C19 | CYP2D6 | CYP11B1 | CYP11B2 |
|---|---|---|---|---|---|---|---|
| 1 | 6.8 | >10000 | >10000 | >10000 | 6546 | 33460 | >50000 |
| 2 | 5.0 | >10000 | >10000 | >10000 | >10000 | 24250 | 30960 |
| 3a | 7.3 | >10000 | >10000 | >10000 | 4055 | 37440 | >50000 |
| 3b | 6.6 | >10000 | >10000 | >10000 | 2395 | 12560 | 42560 |
| 4 | 5.8 | >10000 | >10000 | >10000 | 4870 | 13870 | >50000 |
| 5 | 6.1 | >10000 | >10000 | 7569 | 10000 | 42640 | >50000 |
| 6 | 8.9 | >10000 | >10000 | >10000 | >10000 | 29680 | >50000 |
| 7 | 5.7 | >10000 | >10000 | >10000 | >10000 | 45500 | >50000 |
| 8 | 5.6 | >10000 | >10000 | >10000 | >10000 | 21030 | >50000 |
| 9 | 6.6 | >10000 | >10000 | >10000 | 6634 | 24890 | >50000 |
| 10 | 5.0 | >10000 | >10000 | >10000 | 5913 | >50000 | >50000 |
| 11 | 6.0 | >10000 | >10000 | >10000 | 7064 | 26690 | >50000 |
| 12 | 6.2 | >10000 | >10000 | >10000 | 5084 | 41910 | >50000 |
| 13 | 5.3 | >10000 | >10000 | >10000 | >10000 | 22830 | >50000 |
| 14 | 6.1 | >10000 | >10000 | >10000 | >10000 | 22030 | >50000 |
| 15 | 4.1 | >10000 | >10000 | >10000 | >10000 | 20200 | >50000 |
| 16 | 4.3 | >10000 | >10000 | >10000 | >10000 | 10170 | 24300 |
| 17 | 4.9 | >10000 | >10000 | >10000 | 8602 | 11510 | 31560 |
| 18 | 9.7 | >10000 | >10000 | >10000 | >10000 | >50000 | >50000 |
| 19 | 5.7 | >10000 | >10000 | >10000 | >10000 | 32530 | >50000 |
| 20 | 4.5 | >10000 | >10000 | >10000 | >10000 | 16850 | 31190 |
| 21 | 6.8 | >10000 | >10000 | >10000 | >10000 | >50000 | >50000 |
| 22 | 4.0 | >10000 | >10000 | >10000 | 9751 | 21380 | >50000 |
| 23 | 3.4 | >10000 | >10000 | >10000 | 9722 | 26280 | >50000 |
| 24 | 5.7 | >10000 | >10000 | >10000 | >10000 | >50000 | >50000 |
| 25 | 9.2 | >10000 | >10000 | >10000 | 5848 | >50000 | >50000 |
| 26 | 6.4 | >10000 | >10000 | 6292 | 10000 | 14620 | >50000 |
| 27 | 5.8 | >10000 | >10000 | >10000 | >10000 | 11150 | 23920 |
| 28 | 5.4 | >10000 | >10000 | >10000 | >10000 | 14870 | >50000 |
| 29 | 6.3 | >10000 | >10000 | >10000 | 6220 | 22030 | >50000 |
| 30 | 5.8 | >10000 | >10000 | >10000 | >10000 | >50000 | 41460 |
| 31 | 9.7 | >10000 | >10000 | >10000 | 9604 | 28100 | >50000 |
| 32 | 4.2 | >10000 | >10000 | >10000 | 8378 | 22540 | >50000 |
| 33 | 9.1 | >10000 | >10000 | >10000 | 7364 | >50000 | 23560 |
| 34 | 6.8 | >10000 | >10000 | >10000 | 8052 | 21190 | >50000 |
| 35 | 5.5 | >10000 | >10000 | >10000 | 9098 | 20430 | 25810 |
| 36 | 9.6 | >10000 | >10000 | >10000 | >10000 | 32690 | >50000 |
| 37 | 9.7 | >10000 | >10000 | >10000 | >10000 | 19740 | >50000 |
| 38 | 8.9 | >10000 | >10000 | >10000 | >10000 | 25300 | >50000 |
| 39 | 4.8 | >10000 | >10000 | >10000 | 9446 | 14620 | >50000 |
| 40 | 9.5 | >10000 | >10000 | >10000 | >10000 | 33300 | 25880 |
| 41 | 7.1 | >10000 | >10000 | >10000 | 7476 | 42230 | >50000 |
| 42 | 4.7 | >10000 | >10000 | >10000 | >10000 | 5620 | >50000 |
| 43 | 6.6 | >10000 | >10000 | >10000 | 7089 | 30280 | >50000 |
| 44 | 5.0 | >10000 | >10000 | >10000 | 5860 | 12210 | >50000 |
| 45 | 7.7 | >10000 | >10000 | >10000 | >10000 | >50000 | >50000 |
| 46 | 10.9 | >10000 | >10000 | >10000 | 5796 | >50000 | 23090 |
| 47 | 8.5 | >10000 | >10000 | >10000 | 9251 | 45320 | 9015 |
| 48 | 5.5 | >10000 | >10000 | >10000 | >10000 | 11310 | 15530 |
| 49 | 3.7 | >10000 | >10000 | 9545 | 10000 | 6029 | 36310 |
| 50 | 5.3 | >10000 | >10000 | >10000 | 8082 | 26890 | >50000 |
| 51 | 4.8 | >10000 | >10000 | >10000 | >10000 | 20760 | >50000 |
| 52 | 3.2 | >10000 | >10000 | >10000 | >10000 | 3932 | >50000 |
| 53 | 11.0 | >10000 | >10000 | >10000 | >10000 | 16360 | >50000 |

Example 18

In Vivo Effects of the Compounds of the Invention on the Pharmacokinetics of a Therapeutic Compound Metabolized by CYP3A4 in Han-Wistar Rats The ability of the compounds of the present invention to enhance the exposure of a known HIV protease inhibitor that is metabolized by CYP3A4, Atazanavir (ATV), was evaluated in rats. Fasted male Han-Wistar rats were co-dosed with 10 mg/kg PO dose of a compound of Formula (I) and 10 mg/kg of ATV as a homogeneous solution in 10% Tween (5 mL/kg). The mean Atazanavir AUC and eight-hour plasma concentration values are listed in the Table below and are compared to dosing with and without the PKE.

| Compound of Formula (I) | ATV AUC$_{0-inf}$ (uM * h) | AUC Ratio (+/−) PKE | ATV C$_{8\,h}$ (uM) | C8 h Ratio (+/−) PKE |
|---|---|---|---|---|
| None | 0.9 | 1 | 0.009 | 1 |
| 1 | 1.8 | 2.0 | 0.06 | 6.7 |
| 2 | 5.0 | 5.5 | 0.10 | 11.1 |
| 3 | 3.7 | 4.1 | 0.07 | 7.8 |
| 4 | 5.7 | 6.3 | 0.26 | 28.9 |
| 5 | 3.5 | 3.9 | 0.01 | 1.1 |

-continued

| Compound of Formula (I) | ATV AUC$_{0\text{-}inf}$ (uM * h) | AUC Ratio (+/−) PKE | ATV C$_{8\,h}$ (uM) | C8 h Ratio (+/−) PKE |
|---|---|---|---|---|
| 34 | 9.8 | 10.9 | 1.06 | 117.8 |
| 35 | 2.6 | 2.9 | 0.02 | 2.2 |
| 41 | 9.4 | 10.4 | 0.095 | 10.6 |
| 46 | 6.4 | 7.1 | 0.31 | 34.4 |
| 47 | 2.3 | 2.5 | 0.025 | 2.8 |

Co-administration of compounds in the table above resulted in an increase in mean ATV exposure of 1.5 to 8.2 fold and higher mean plasma drug concentrations at eight hours (1.1 to 117 fold). These results show that the compounds of the present invention are efficient and potent enhancer of the pharmacokinetics of Atazanavir in vivo.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. The compound, having the formula (Ic);

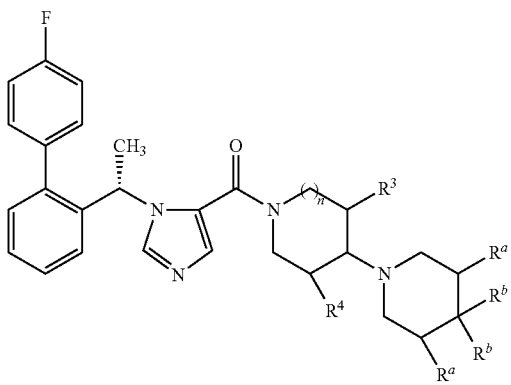

(Ic)

or a pharmaceutically acceptable salt thereof,
wherein:
n is 1 or 2;
R$^3$ is selected from H, halo and C$_1$-C$_6$ alkyl;
R$^4$ is selected from H, halo and C$_1$-C$_6$ alkyl;
each occurrence of R$^a$ is independently H, methoxy, halo or methyl; and
each occurrence of R$^b$ is independently H, methoxy, halo or methyl.

2. The compound of claim 1, wherein n is 1.
3. The compound of claim 1, wherein n is 2.
4. A compound having the structure:

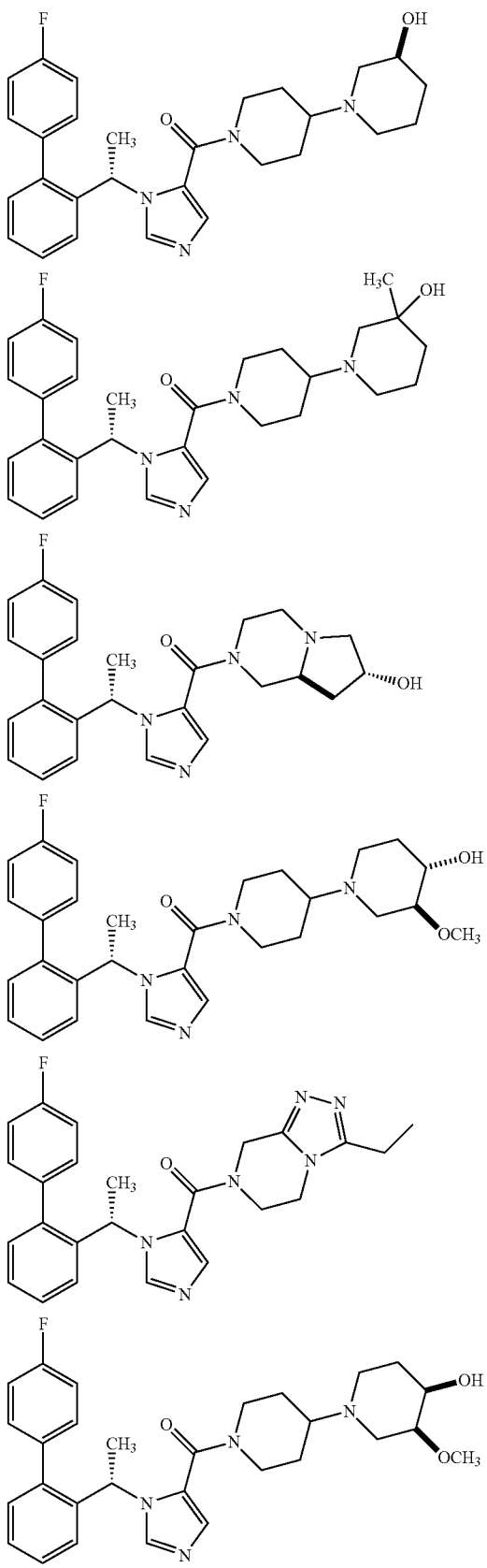

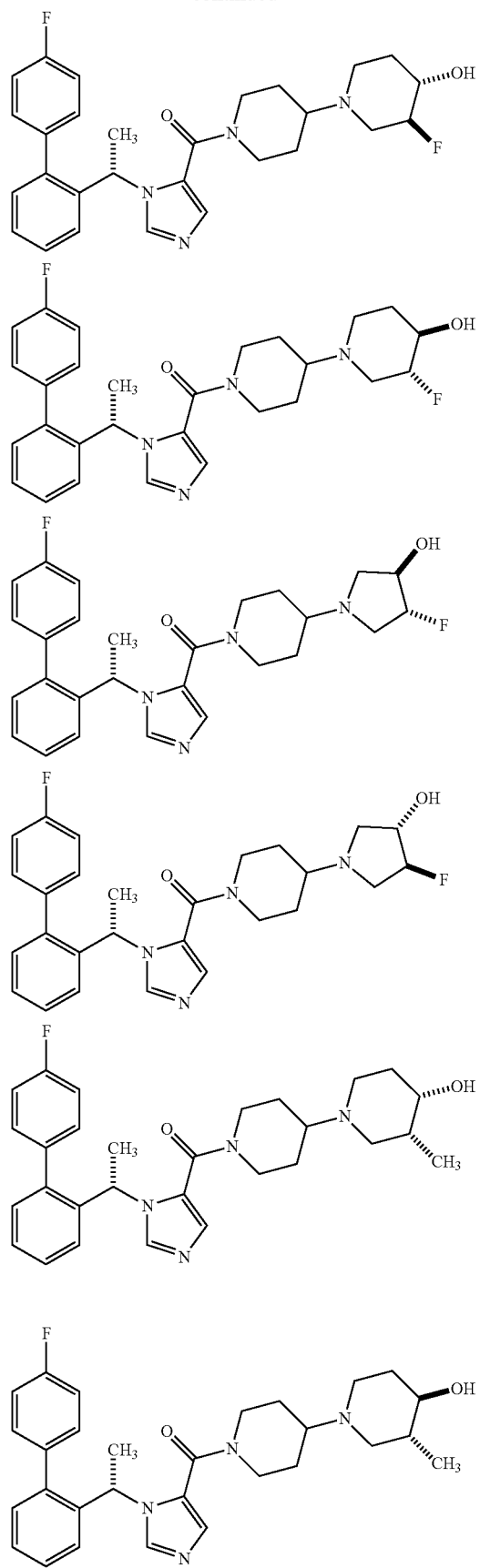
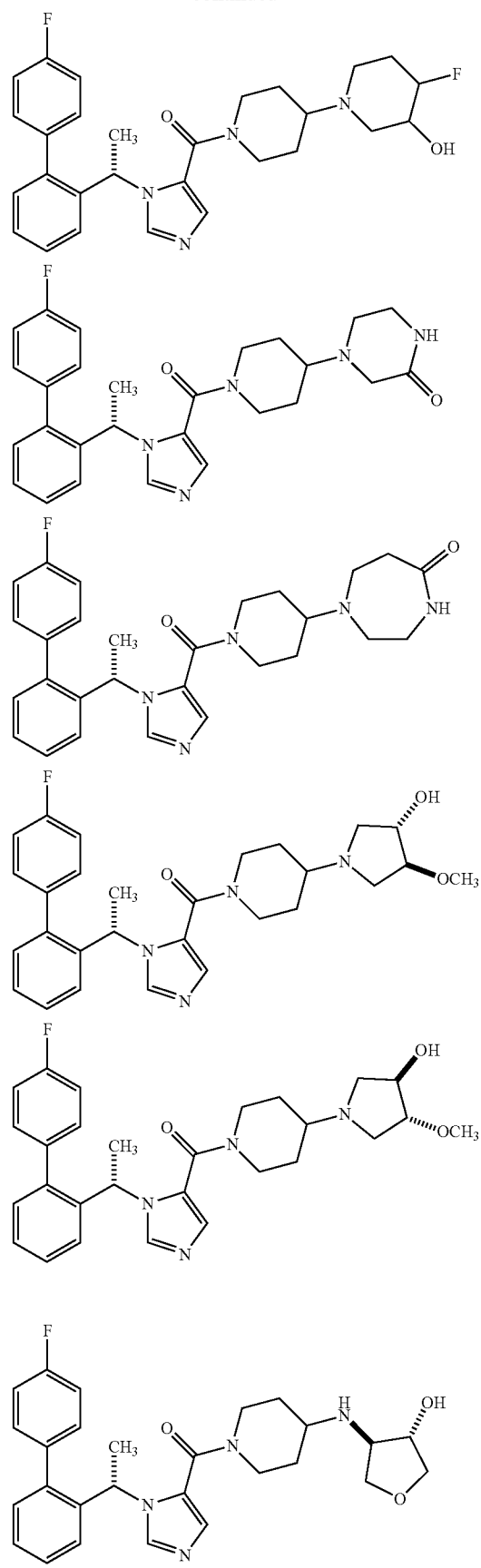

111
-continued
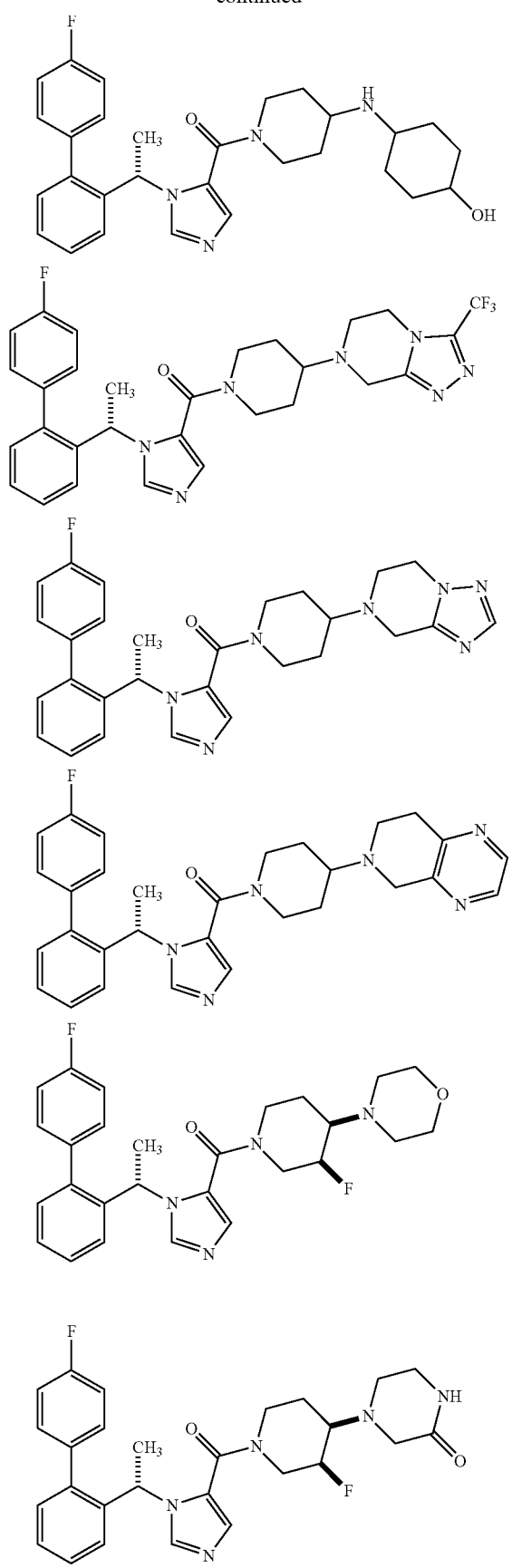
112
-continued
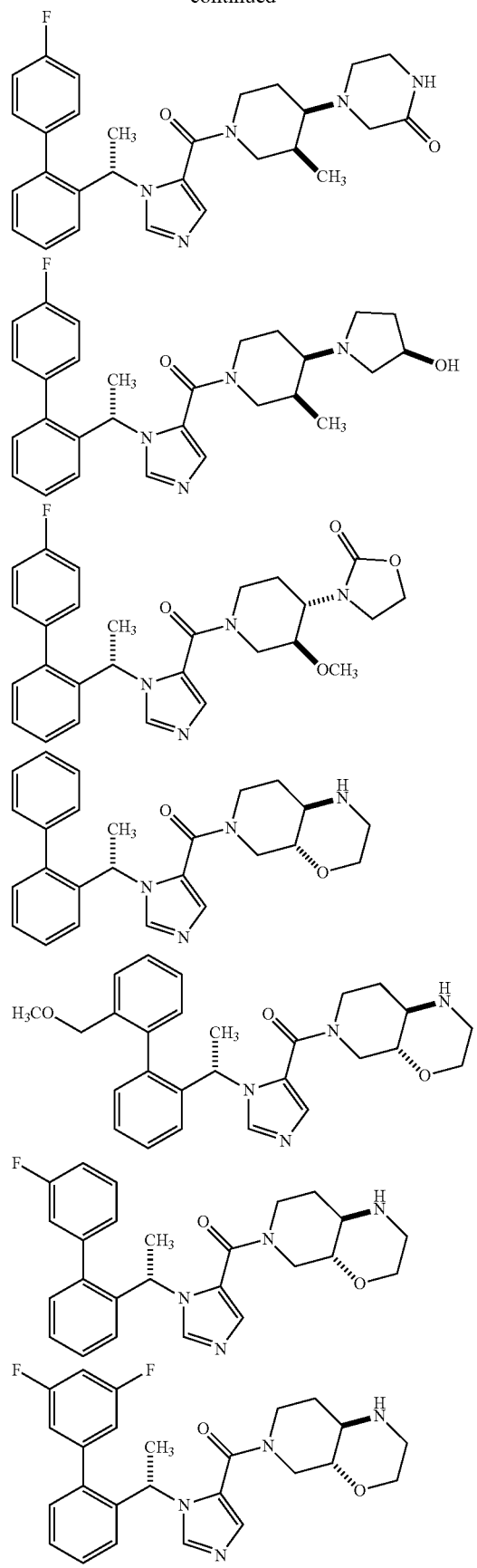

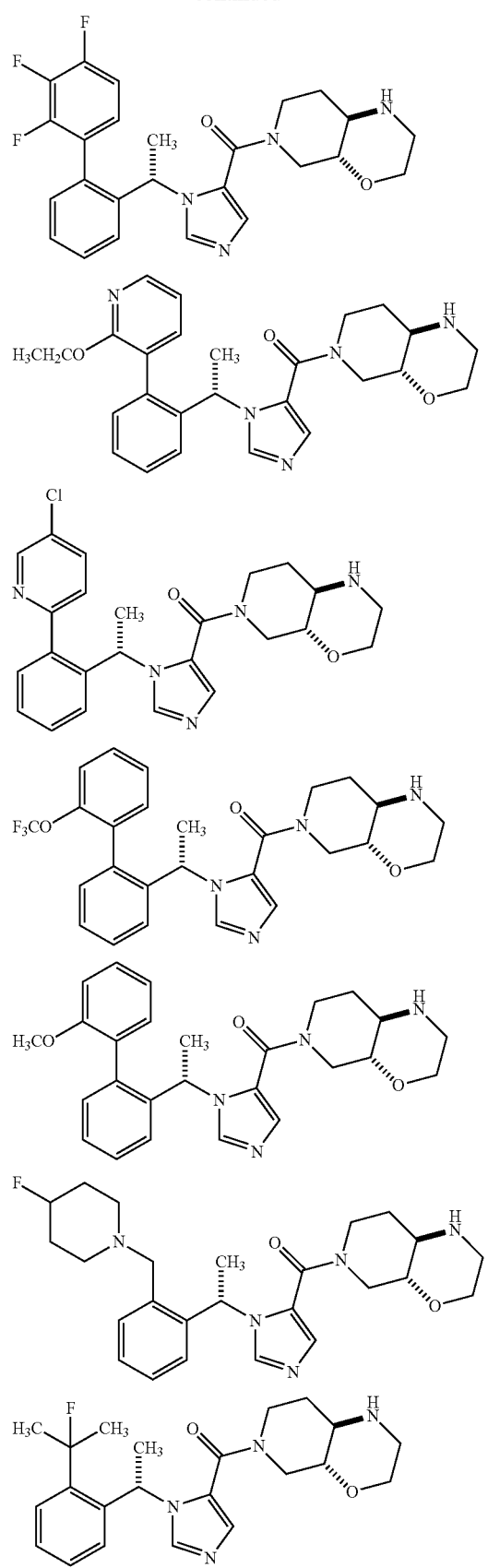
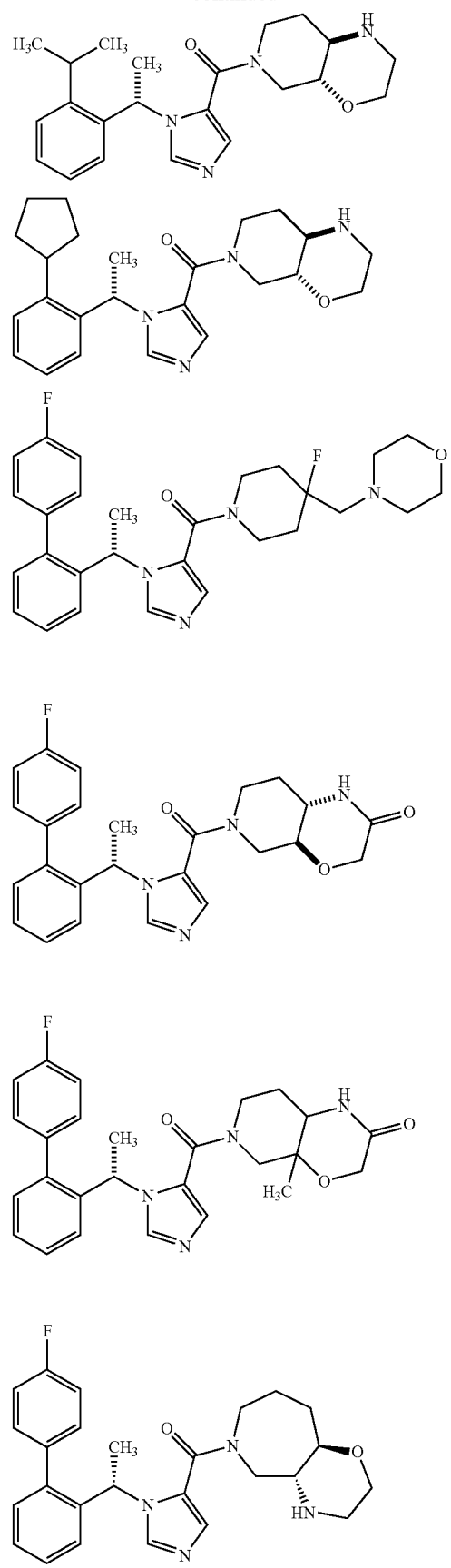

-continued
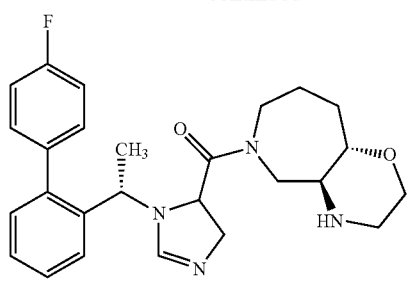
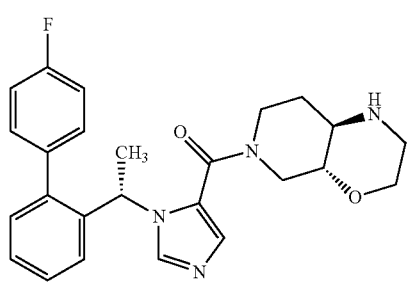
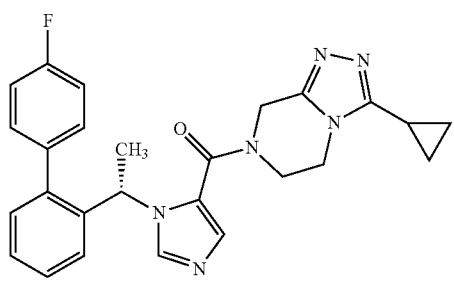
-continued
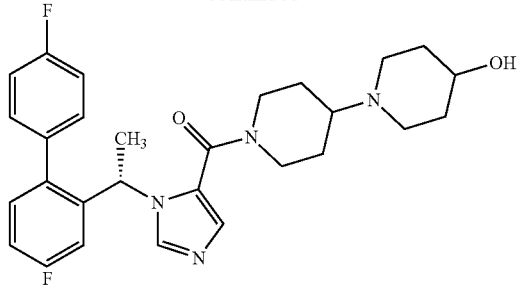
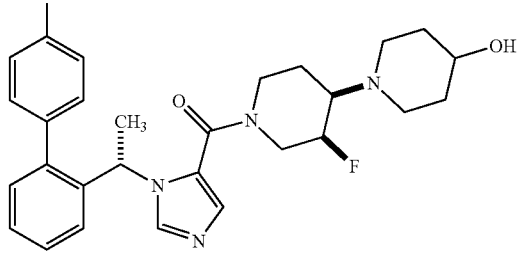
or
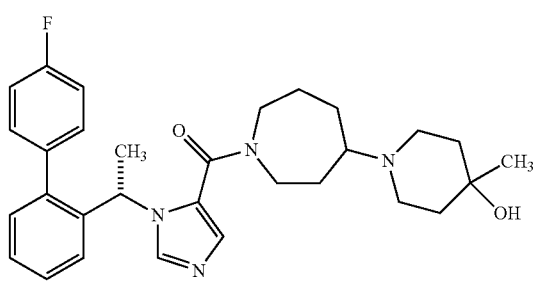
or a pharmaceutically acceptable salt thereof.
5. A pharmaceutical composition comprising an effective amount of a compound of claim 1 and a pharmaceutically acceptable carrier.
* * * * *